United States Patent [19]

Wissner

[11] Patent Number: 5,350,759
[45] Date of Patent: Sep. 27, 1994

[54] BIS-ARYL AMIDE ANTAGONISTS OF PLATELET ACTIVATING FACTOR

[76] Inventor: Allan Wissner, 31 Wood Ave., Ardsley, Westchester, N.Y. 10502

[21] Appl. No.: 43,054

[22] Filed: Apr. 5, 1993

Related U.S. Application Data

[62] Division of Ser. No. 868,169, Apr. 14, 1992, Pat. No. 5,225,425, which is a division of Ser. No. 519,525, May 4, 1990, Pat. No. 5,128,351.

[51] Int. Cl.$^5$ ............... A61K 31/425; C07D 277/30
[52] U.S. Cl. .................... 514/365; 514/369; 548/183; 548/187; 548/200; 548/205
[58] Field of Search ............ 548/183, 187, 200, 205; 514/365, 369

[56] References Cited

U.S. PATENT DOCUMENTS 4,692,450 9/1987 Cassal .................. 548/204

Primary Examiner—Bernard Dentz

[57] ABSTRACT

Bis-aryl amide and urea compounds of the general formula:

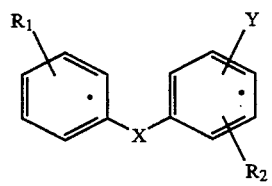

wherein X is a divalent amide or urea substituent and Y is a nitrogen containing heterocycle, which compounds are inhibitors of platelet activating factor. Pharmaceutical compositions containing the compounds and methods of treating platelet activating factor associated conditions are also included.

14 Claims, No Drawings

BIS-ARYL AMIDE ANTAGONISTS OF PLATELET ACTIVATING FACTOR

This is a divisional of co-pending application Ser. No. 07/868,169, filed on Apr. 14, 1992, now U.S. Pat. No. 5,225,425, which is a divisional of application Ser. No. 07/519,525 filed May 4, 1990, now U.S. Pat. No. 5,128,351.

BACKGROUND OF THE INVENTION

Platelet Activating Factor (PAF), 1-0-hexadecyl/octadecyl-2-acetyl-sn-glyceryl-3-phosphorylcholine, is an ether lipid produced by a variety of different cell types. Recent studies [Snyder, F., Ann. Rep. Med. Chem., 17, 243 (1982); Pinckard, R. N., et. al., J. Adv. Inflammation Res., 4, 147 (1982); O'Flaherty, J. T., et. al., Clin. Rev. Allergy, 1, 353 (1983); Vargaftig, B. B., et. al., J. Trends. Pharmacol. Sci., 4, 341 (1983)] have shown PAF to be an important mediator of allergic disease. When injected into mammals, PAF induces hemodynamic and hematological changes including hypotension, platelet aggregation, neutropenia, disseminated intravascular coagulation, increases in vascular permeability, bronchoconstriction, tissue injury (hypoxia and necrosis) and eventually death (reviewed by Cammussi, G. Kidney Int. 29, 469, 1986). In recent years, it has been postulated that PAF is the mediator of tissue injury in mammals undergoing endotoxic shock due to bacterial sepsis (Terashita, Z., Y. Imura, K. Nishikawa and S. Sumida 1985, Eur. J. Pharmacol. 109:257–261; Doebber, T. W., M. S. Wu, J. C. Robbins, B. M. Choy, M. N. Chang and T. Y. Shen 1985, Biochem. Biophys. Res. Comm. 127:799–808; Inarrea, P., Gomez-Cambronero, J. Pascual, M. del Carmen Ponte, L. Hernando and M. Sanchez-Crespo. 1985, Immunopharmacology, 9:45–52). These studies, in mammals, have shown that PAF is produced in large amounts when the said mammal has been treated with endotoxin. In addition, mammals undergoing endotoxic shock exhibit all of the clinical symptoms associated with the administration of PAF. In addition, PAF is implicated in asthma, respiratory distress syndrome, lung edema and other inflammatory and cardiovascular diseases.

The compounds of the present invention have proven to be specific inhibitors of the biological effects of PAF and are consequently useful for the treatment of asthma, anaphylactic and septic (endotoxic) shock, psoriasis, bowel necrosis, adult respiratory distress syndrome, transplant rejection, thrombosis, stroke, cardiac anaphylaxis and cancer.

Concurrently, with the realization that PAF is an important mediator of inflammatory diseases in mammals, a number of structurally different antagonists of PAF have been developed. References to some of these antagonists are listed hereinbelow.

Takatani, M., et al., J. Med. Chem., 32(1), 56–64 (1989)
Terashita, Z., et al., J. Pharmacol. Exp. Ther., 242(1), 263-8 (1987)
Wissner, A, et al., J. Med. Chem., 29(3), 328–33 (1986)
Tomesch, J., U.S. Pat. No. 4,820,718, Apr. 11, 1989
Guthrie, R. W., et al., J. Med. Chem. 32(8) 1820–35 (1989)
Guthrie, R. W., et al., U.S. Pat. No. 4,786,646, Nov. 22, 1988

BRIEF SUMMARY OF THE INVENTION

The compounds of the present invention are represented by the Formula I:

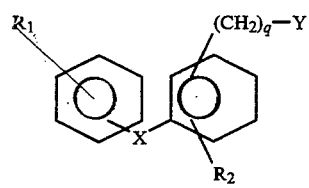

wherein: (A) X is a divalent radical selected from the group consisting of:

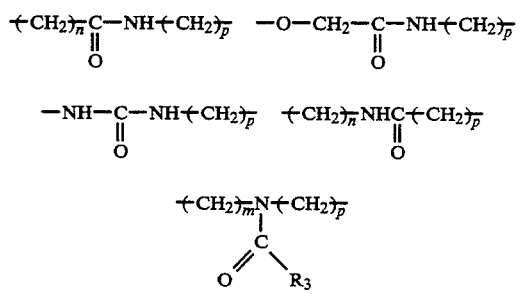

wherein p is the integer 0 or 1; n is the integer 0, 1, or 2; m is the integer 0, 1, 2 or 3; $R_3$ is selected from the group consisting of $C_1$-$C_4$ alkyl, $C_1$-$C_4$ alkoxy, and $C_1$-$C_4$ alkylamino; (B) $R_1$ represents one or more substituents of the aromatic ring which may be the same or different and is selected from the group consisting of: (i) $C_1$-$C_{25}$ alkyl, $C_1$-$C_{25}$ alkenyl, $C_1$-$C_{25}$ alkoxy, $C_1$-$C_{25}$ thioalkyl, $C_1$-$C_{25}$ alkenyloxy, phenyl, phenoxy, substituted phenyl and substituted phenoxy wherein the substituents are selected from the group consisting of $C_1$-$C_{20}$ alkyl, $C_1$-$C_{20}$ alkoxy, halogen and trifluoromethyl; (ii) hydrogen, halogen, trifluoromethyl, cyano and nitro; (iii) —$CO_2R_4$, —$CONHR_3$, —CHO, $OCONHR_4$, and —$NHCOR_4$ wherein $R_4$ is selected from the group consisting of $C_1$-$C_{25}$ alkyl, $C_1$-$C_{25}$ alkenyl, phenyl and substituted phenyl wherein the substituents are selected from the group consisting of $C_1$-$C_{20}$ alkyl, $C_1$-$C_{20}$ alkoxy, halogen and trifluoromethyl; (C) the moiety $R_2$ represents one or more substituents of the aromatic ring which may be in any position and are selected from the group consisting of hydrogen $C_1$-$C_5$ alkyl, $C_1$-$C_5$ alkoxy and halogen; (D) the moiety —$(CH_2)_q$—Y is a moiety wherein q is an integer from 0 to 1 and Y represents a single substituent of the aromatic ring which may occupy any position and is a stable, optionally substituted mono or bicyclic aromatic heterocycle with 5–6 membered rings containing at least one nitrogen atom and optionally one or more other nitrogen or sulfur atoms; the substituents of the heterocycle are selected from the group consisting of $C_1$-$C_6$ alkyl, $C_1$-$C_6$ acyl, or $C_1$-$C_6$ alkoxy. A preferred embodiment is compounds of Formula I wherein Y is:

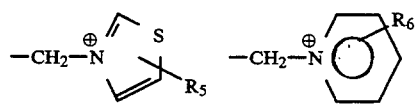

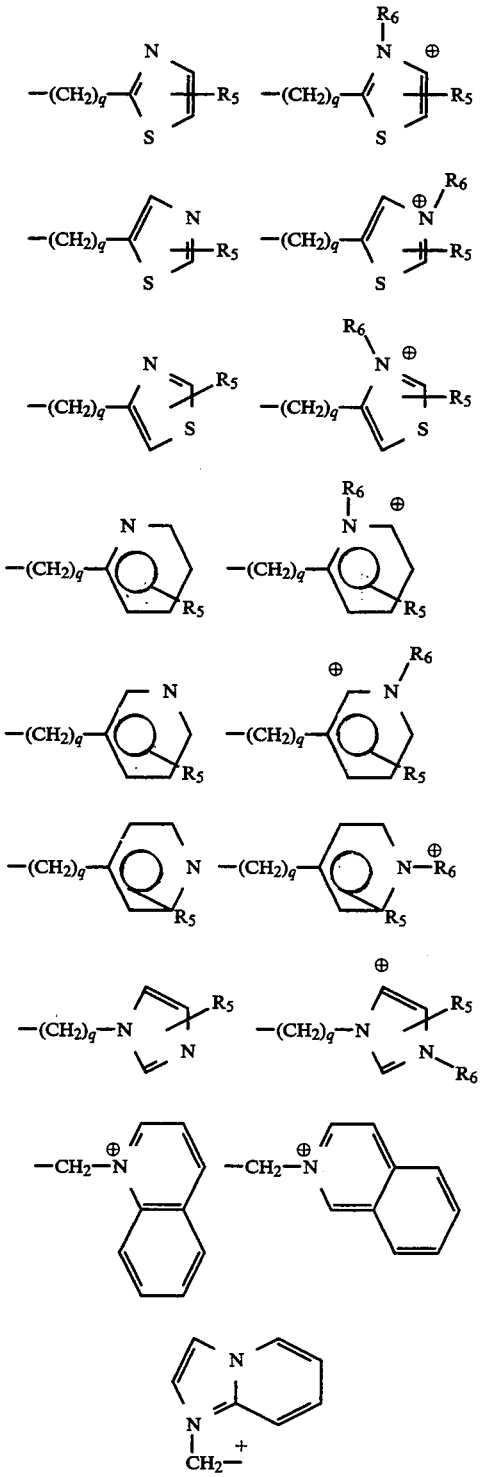

wherein the moiety $R_5$ is one or more substituents of the heterocyclic ring which may be the same or different and are selected from the group consisting of hydrogen, $C_1$–$C_6$ alkyl, $C_1$–$C_6$ acyl, or $C_1$–$C_6$ alkoxy; $R_6$ is $C_1$–$C_4$ alkyl; q is 0 or 1; and the pharmacologically acceptable salts thereof.

DETAILED DESCRIPTION OF THE INVENTION

The preparation of the compound of the present invention encompassed by Formula 8 is described hereinbelow in Flowsheet A wherein $R_1$, $R_2$ and n are described hereinabove. The moiety $R_7$ is a $C_1$ to $C_6$ alkyl group. $R_8$ is selected from the group consisting of —$CH_2OH$, and —$CO_2R_7$. Y' is an optionally substituted mono or bicyclic heterocycle with 5–6 membered rings containing at least one nitrogen atom (which is bonded directly to the methylene group) and optionally one or more nitrogen or sulfur atoms.

In a specific embodiment, Y' is selected from the group consisting of:

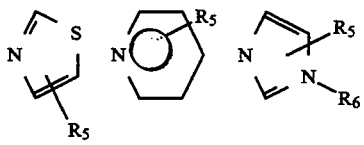

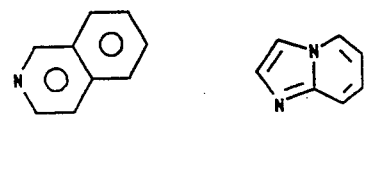

wherein $R_5$ and $R_6$ are as described hereinabove.

According to sequence of reactions outlined in flowchart A, the carboxylic acid ester 2 is hydrolyzed with sodium or potassium hydroxide in aqueous alcohol to give the carboxylic acid 3 which is converted to the acid chloride 4 using oxalyl chloride in the presence of a catalytic amount of dimethylformamide (DMF) in an inert solvent such as methylene chloride. The acid chloride is reacted with amine 5 in the presence of a base such as triethylamine or pyridine to give the amides represented by Formula 6. For those compounds wherein $R_8$ is —$CH_2OH$ (6a), the alcohol is converted to the mesylate using methanesulfonyl chloride and a base such as triethylamine in an inert solvent such as tetrahydrofuran (THF). This mesylate can, without isolation, be converted to the bromide 7, by treating the reaction mixture with an excess of lithium bromide. Alternatively, the bromide can be prepared directly by heating 6a in HBr in acetic acid. Alkylation of bromide 7 with a nitrogen containing heterocycle Y' in an inert solvent with heating gives the compounds of this invention represented by Formula 8.

In those cases wherein $R_8$ is —$CO_2R_7$ (6b), the ester group is first reduced with lithium borohydride in refluxing THF to give the alcohol 6a which is converted to the compounds of this invention 8 as described hereinabove.

Flowsheet A

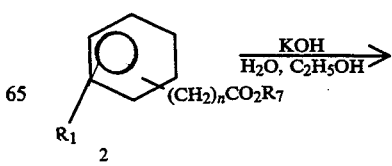

-continued
Flowsheet A

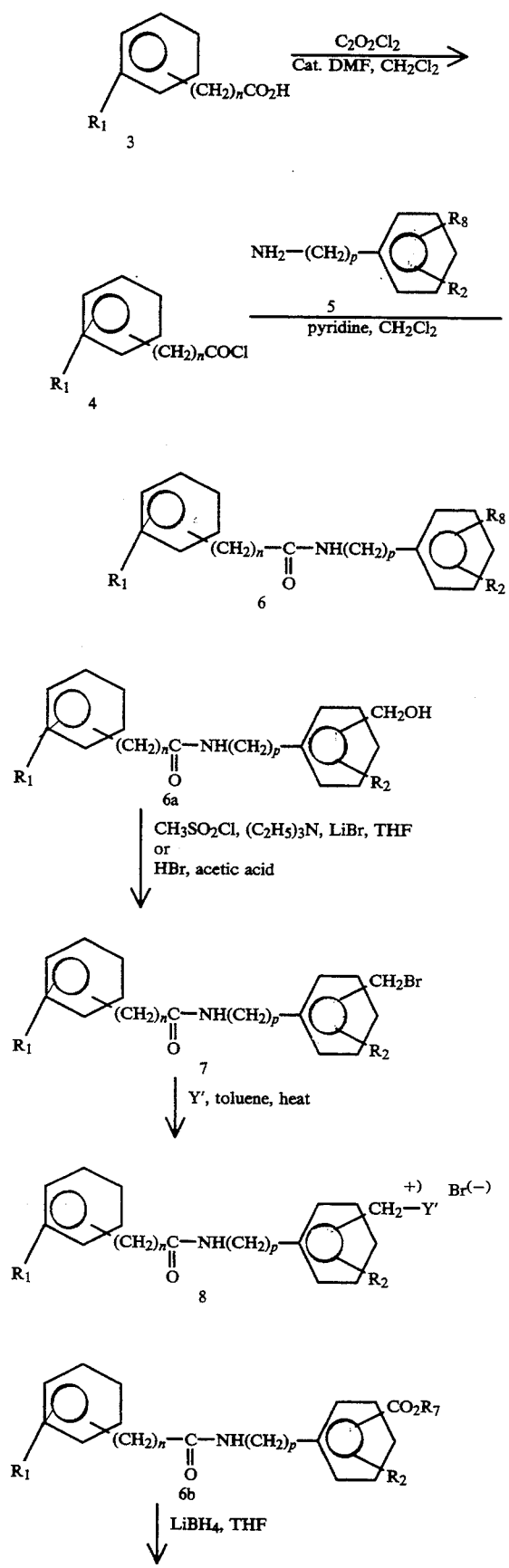

-continued
Flowsheet A

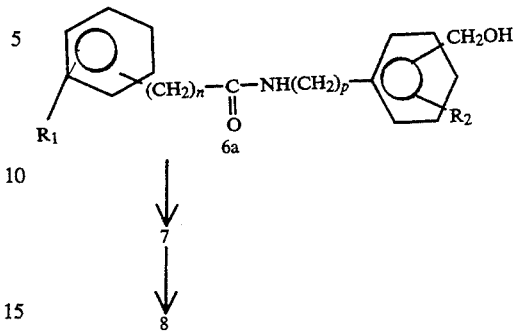

The preparations of compounds of this invention represented by Formulas 13–16 are described hereinbelow in Flowsheet B wherein $R_1$, $R_2$, $R_6$, p and n are described hereinabove. The moiety Y″ is an optionally substituted mono or bicyclic heterocycle with 5–6 membered rings containing at least one nitrogen atom; the heterocycle is bonded to the molecule through attachment of one of its carbon atoms. More specifically, Y″ is selected from the group consisting of:

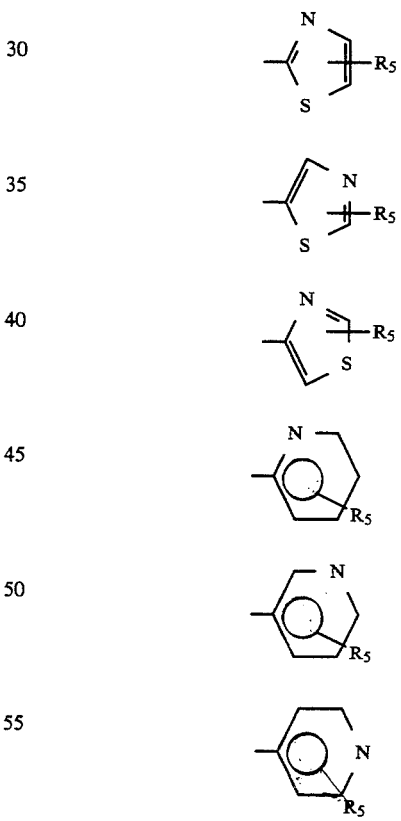

The moiety Y‴ is an optionally substituted mono or bicyclic heterocycle with 5–6 membered rings containing at least one alkylated nitrogen atom; the heterocycle is bonded to the molecule through attachment of one of its carbon atoms. More specifically, Y‴ is selected from the group consisting of those of the following formula wherein J is the halogen atoms I, or Br or is a trifluoromethyl sulfonyl group.:

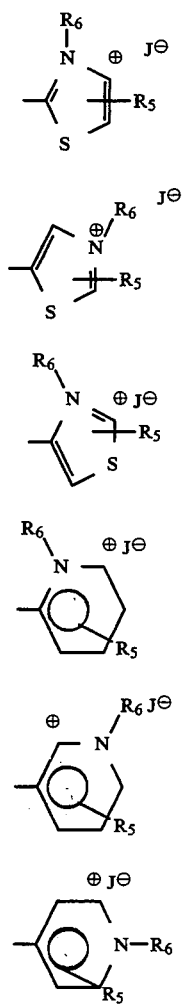

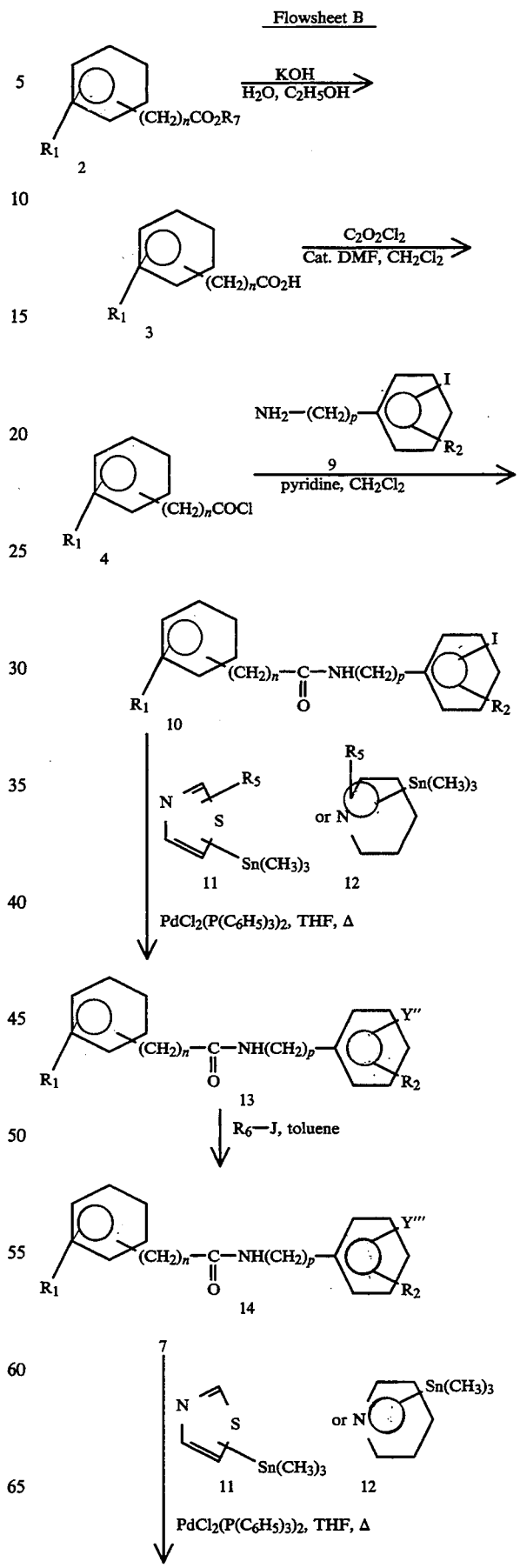

According to sequence of reactions outlined in Flowchart B, the carboxylic acid ester 2 is hydrolyzed with sodium or potassium hydroxide in aqueous alcohol to give carboxylic acid 3 which is converted to the acid chloride 4 using oxalyl chloride in the presence of a catalytic amount of dimethylformamide (DMF) in an inert solvent such as methylene chloride. The acid chloride is reacted with amine 9 in the presence of a base such as triethylamine/pyridine to give the amides represented by Formula 10. The aromatic iodides 10 or the benzyl bromides represented by Formula 7 (see Flowsheet A) are heated with a trimethyl tin substituted heterocycle such as 11 or 12 in an inert solvent such as THF in the presence of a catalytic amount of a palladium catalyst to give the compounds of this invention 13 or 15, respectively. Compounds 13 or 15 can be alkylated with an alkyl halide or alkyltrifluoromethanesulfonate to give the charged compounds of this invention 14 and 16, respectively.

The trimethyltin substituted heterocycles such as 11 or 12 needed to prepare some of the compounds of this invention can be prepared as described in the following references: Dondoni, P., Mastellari, A. R., Medici, A.; Negrini, E., Pedrini, P. *Synthesis* 757 (1986); Bailey, T. R., *Tet. Lett.* 27, 4407 (1986); Jutzi, P. and Gilge, U., *J. Organmet. Chem.*, 246, 163 (1983).

-continued
Flowsheet B

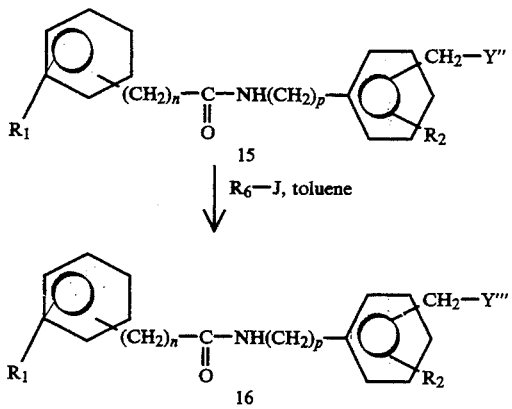

The preparation of the compounds of this invention encompassed by Formula 20 is described hereinbelow in Flowsheet C wherein $R_1$, $R_2$, $R_3$, $Y'$, $R_6$, m, n, and p are described hereinabove. The group $R_9$ is $C_1$-$C_4$ alkyl. According to the sequence of reactions outlined in Flowsheet C, the benzyl alcohol 6a (see Flowsheet A) is reduced with a reducing agent such as lithium aluminum hydride in an inert solvent such as THF at 0° to 65° to give the amine 17. The reaction of 17 with at least two equivalents of an anhydride, acid chloride, isocyanate, or chloroformate in the presence of a base such as pyridine in methylene chloride gives the bis-functionalized derivative 18. When $R_3$ is $C_1$-$C_4$ alkyl or $C_1$-$C_4$ alkoxy, the ester and carbonate groups, respectively, can be selectively hydrolyzed. Treating the resulting benzyl alcohol with methanesulfonyl chloride and a base such as triethylamine in THF gives a mesylate which can, without isolation, be converted to bromide 19 by reacting it with a large excess of lithium bromide. Alternatively, when $R_3$ is $C_1$-$C_4$ alkyl, $C_1$-$C_4$ alkoxy, or $C_1$-$C_4$ alkylamino, the bromide 19 can be prepared directly by heating 18 in HBr-acetic acid. Alkylation of 19 with a nitrogen-containing heterocycle $Y'$ in an inert solvent with heating gives the compounds of this invention represented by Formula 20.

Flowsheet C

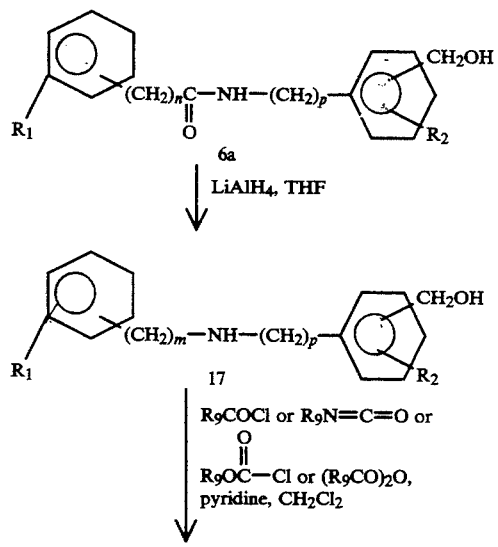

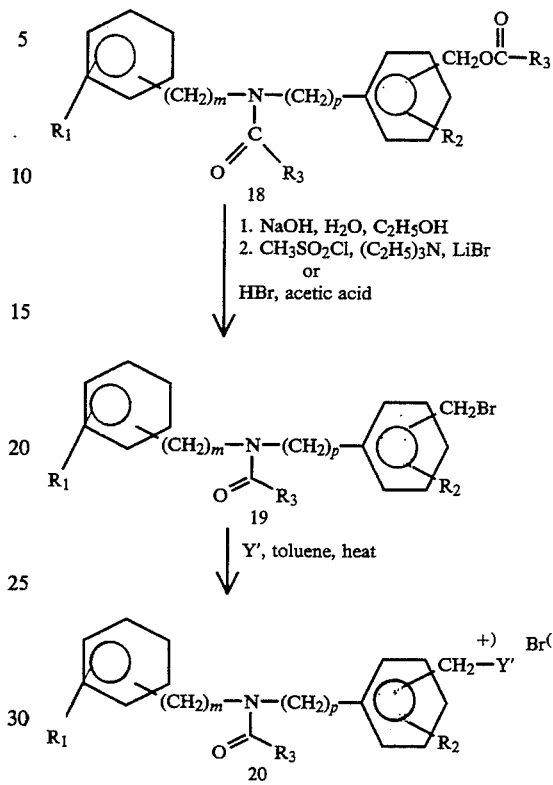

The preparations of compounds of this invention represented by Formulas 23, 24, 25 and 26 are described hereinbelow in Flowsheet D wherein J, $R_1$, $R_2$, $R_3$, $R_5$, $R_6$, $R_9$, m, n, p, $Y'''$, and $Y'''$ are described hereinabove. According to the sequence of reactions outlined hereinbelow in Flowsheet D, the amides represented by Formula 10 (see Flowsheet B) are reduced with lithium aluminum hydride or similar reducing agent to give the amines 21. The reaction of these amines with an anhydride, acid chloride, isocyanate, or chloroformate gives aromatic iodides 22. The aromatic iodides 22.. or the benzyl bromides represented by Formula 19 (see Flowsheet C) are heated with a trimethyltin substituted heterocycle such as 11 or 12 in an inert solvent such as THF in the presence of a catalytic amount of a palladium catalyst to give the compounds of this invention 23 or 25, respectively. Compounds 23 or 25 can be alkylated with an alkyl halide or alkyltrifluoromethanesulfonate to give the charged compounds of this invention 24 and 26, respectively.

Flowsheet D

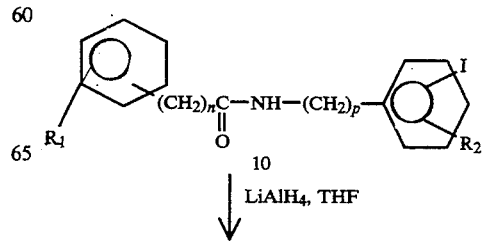

Flowsheet D

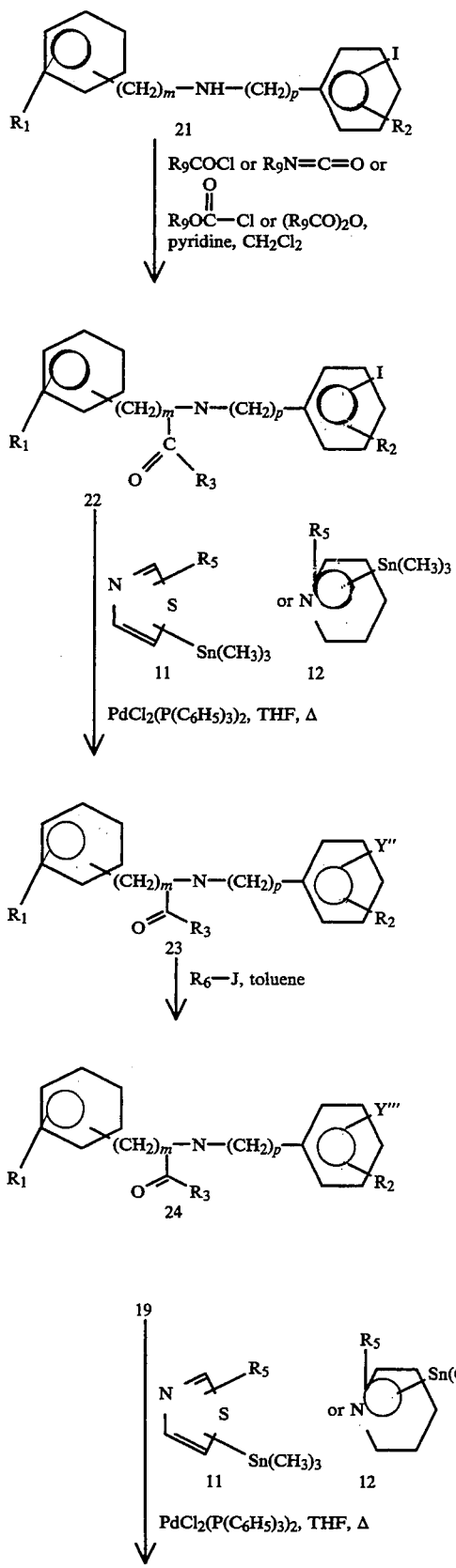

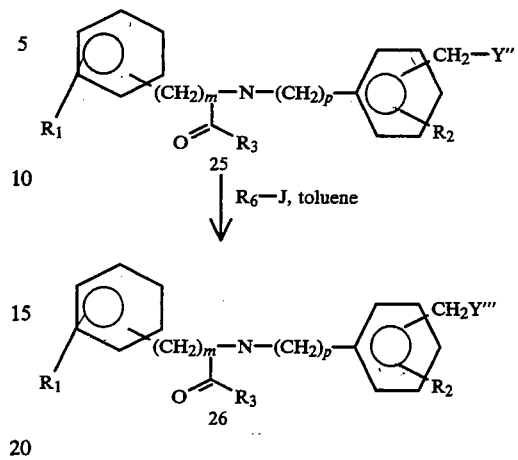

Compounds of this invention represented by Formula 33 are prepared as outlined hereinbelow in Flowsheet E wherein $R_2$, $R_5$, $R_1$, n, $R_6$ and J are as defined hereinabove. The reaction of the aromatic nitro fluorides 27 with the imidazoles 28 in the presence of a base such as potassium carbonate in dimethylsulfoxide (DMSO) at elevated temperature gives the nitro compounds 29. These are reduced catalytically with hydrogen in buffered methanol to give the substituted anilines 30. The reaction of acid chloride 4 (see Flowsheet A) with the anilines 30 gives the compounds of this invention represented by Formula 31. Alkylation of 31 with an alkyl halide or trifluoromethylsulfonate 32 gives the charged compounds of this invention represented by Formula 33.

Flowsheet E

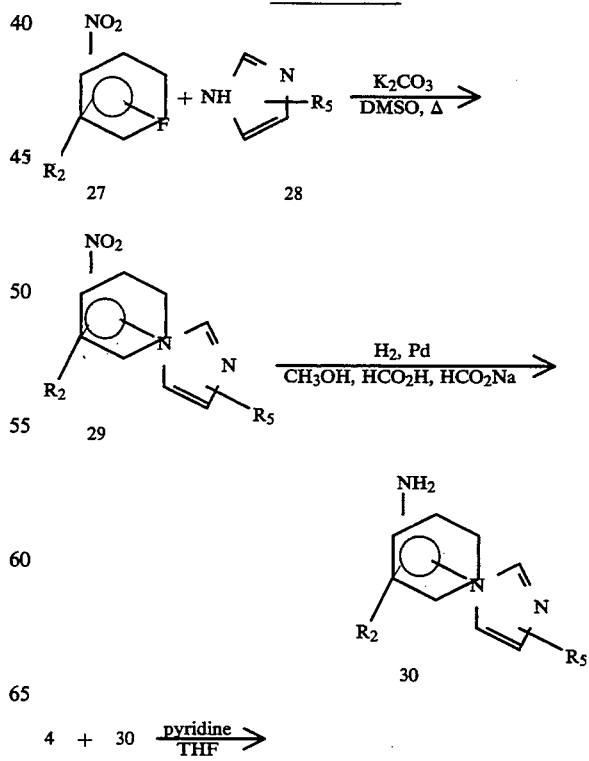

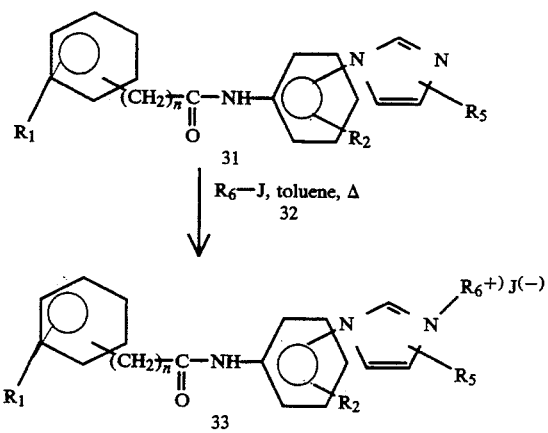

The preparation of compounds of this invention encompassed by Formula 41 is described hereinbelow in Flowsheet F wherein $R_1$, $R_2$, p, $R_7$ and Y' are as described hereinabove. According to the sequence of reactions outlined in Flowsheet F, alkylation of phenol 34 with an alkyl bromoacetate using potassium carbonate in refluxing acetone gives the carboxylic acid ester 35. The substituted phenols 34 needed to prepare the compounds can be prepared as described in the following U.S. Pat. Nos.: 4,697,031; 4,699,990 and 4,640,913 and in our copending application Ser. No. 286,193, filed in December 1988. The carboxylic acid ester 35 is hydrolyzed with sodium or potassium hydroxide in aqueous alcohol to give the carboxylic acid 36 which is converted to the acid chloride 37 using oxalyl chloride in the presence of a catalytic amount of dimethylformamide (DMF) in an inert solvent such as methylene chloride. The acid chloride is reacted with amine 38 in the presence of a base such as triethylamine or pyridine to give the amides represented by Formula 39. The alcohol 39 is converted to the mesylate using methanesulfonyl chloride and a base such as triethylamine in an inert solvent such as tetrahydrofuran (THF). This mesylate can, without isolation, be converted to the bromide 40, by treating the reaction mixture with an excess of lithium bromide. Alternatively, the bromide can be prepared directly by heating 39 in HBr in acetic acid. Alkylation of bromide 40 with a nitrogen-containing heterocycle Y' in an inert solvent with heating gives the compounds of this invention represented by Formula 41.

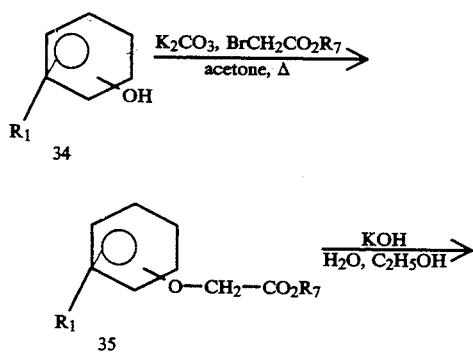

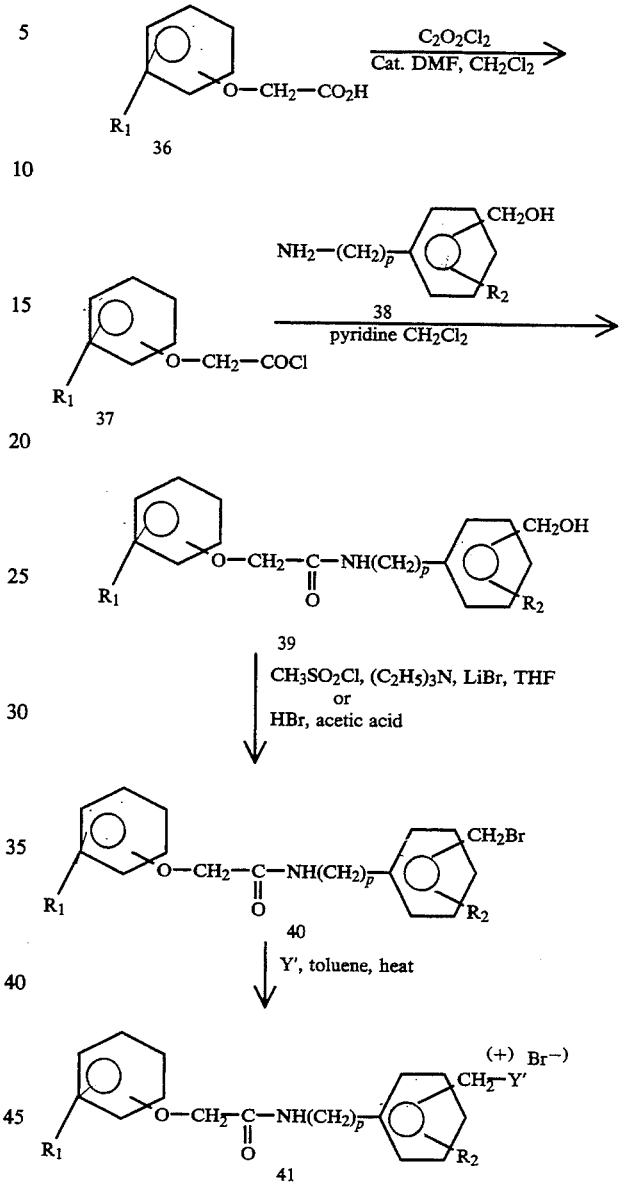

The preparations of compounds of this invention represented by Formulas 43–46 are described hereinbelow in Flowsheet G wherein $R_1$, $R_2$, $R_6$, p, $R_5$, J, Y''' and Y'''' are as described hereinabove. According to the sequence of reactions outlined in Flowsheet G, the acid chloride 37 is reacted with amine 9 in the presence of a base such as triethylamine in pyridine to give the amides represented by Formula 42. The aromatic iodides 42 or the benzyl bromides represented by Formula 40 (see Flowsheet F) are heated with a trimethyl tin substituted heterocycle such as 11 or 12 in an inert solvent such as THF in the presence of a catalytic amount of a palladium catalyst to give the compounds of this invention 43 or 45, respectively. Compounds 43 or 45 can be alkylated with an alkyl halide or alkyltrifluoromethanesulfonate to give the charged compounds of this invention 44 and 46, respectively.

Flowsheet G

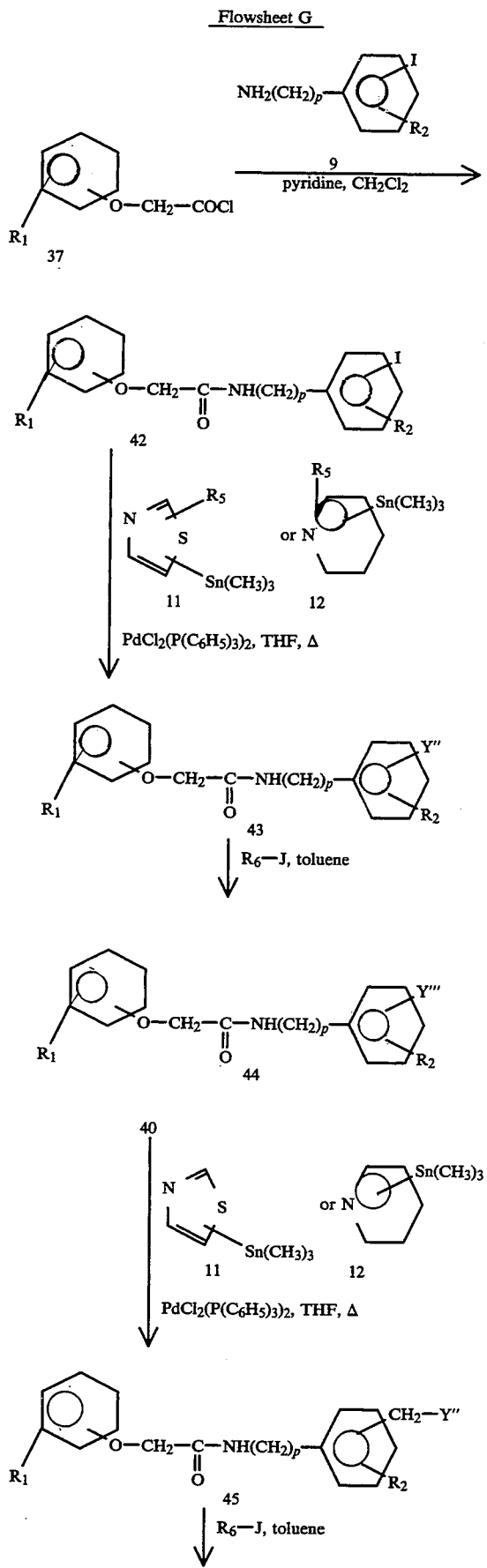

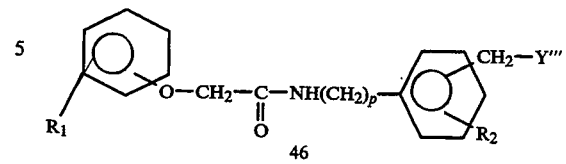

-continued
Flowsheet G

Compounds of this invention represented by Formula 52 are prepared as outlined hereinbelow in Flowsheet H wherein $R_1$, $R_2$, p, and Y' are as described hereinabove. The reaction of carboxylic acid 47 [J. Amer. Chem. Soc., 62 1180 (1940)] with oxalyl chloride in an inert solvent such as methylene chloride in the presence of a catalytic quantity of dimethylformamide (DMF) gives the acid chloride 48. Substituted nitrobenzenes 49 can be reduced to the corresponding anilines 50 by catalytic hydrogenation in an alcohol solvent. The reaction of 50 and 48 in tetrahydrofuran in the presence of pyridine gives the amides 51. Alkylation of 51 with a nitrogen-containing heterocycle Y' in an inert solvent such as acetonitrile at elevated temperature gives the compounds of this invention represented by Formula 52.

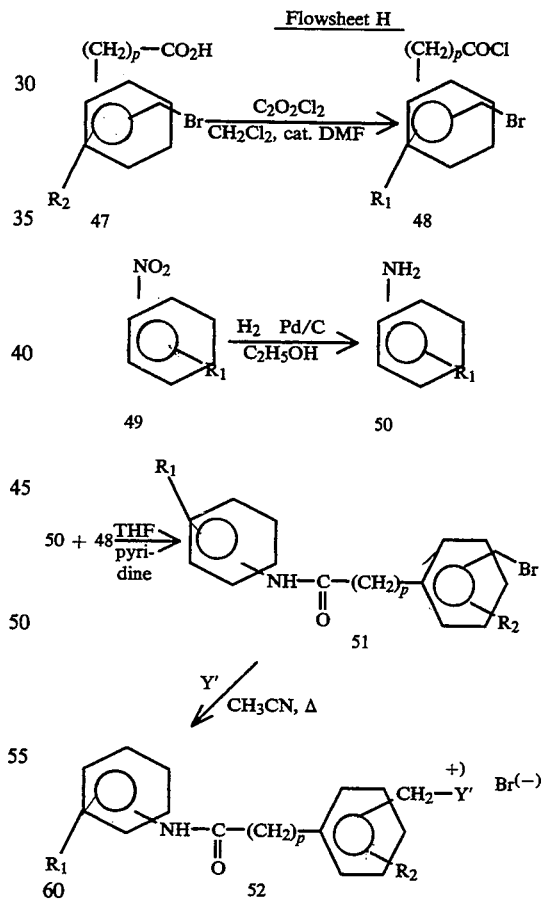

The urea compounds of this invention represented by Formula 56 are prepared as shown hereinbelow in Flowsheet I wherein $R_1$, $R_2$, p, and Y' are as described hereinabove, The anilines 50 (see Flowsheet H) are converted to the isocyanates 53 by treatment with triphosgene, triethylamine, and a small quantity of N,N-dimethylamino pyridine in methylene chloride. The reaction of 53 with amino alcohol 38 catalyzed by pyridine in THF gives the urea 54. The bromide 55 is prepared by reaction of 54 with hydrobromic acid in acetic acid. Alkylation of 55 with a nitrogen-containing heterocycle Y' in an inert solvent such as acetonitrile at elevated temperature gives the urea compounds of this invention represented by Formula 56.

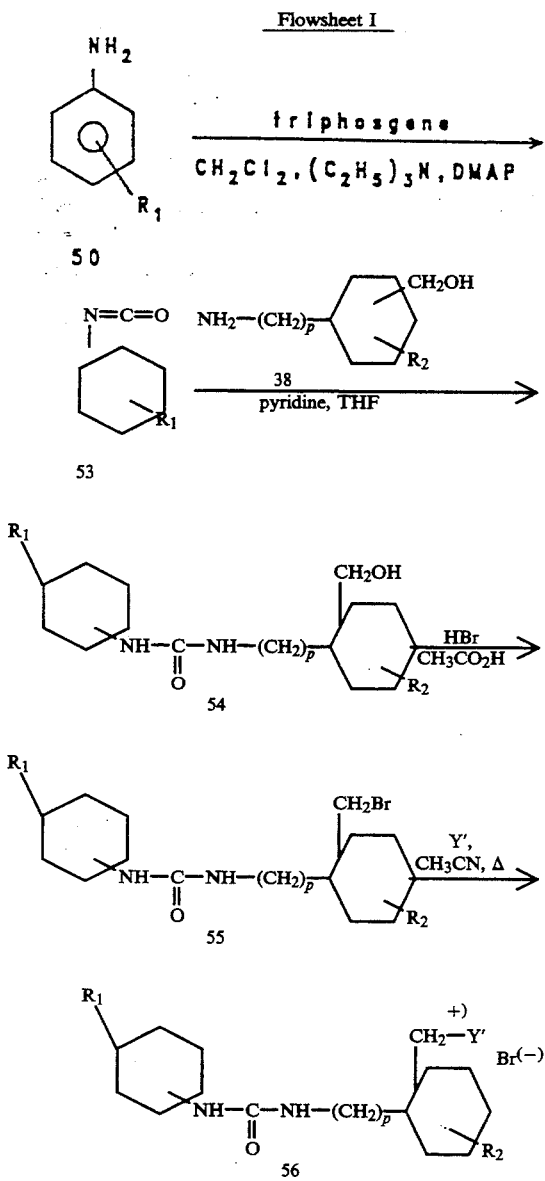

The compounds of this invention are tested for pharmacological activity as described in the following tests.

Platelet Activating Factor Antagonism In Vitro

Test compounds are evaluated as PAF receptor antagonists in vitro by measuring inhibition of PAF (platelet activating factor) induced platelet aggregation. Platelet aggregation is measured by a modification of the method described in A. Wissner, et. al., J. Med. Chem., 27 1174, 1984.

Approximately 120–240 ml of blood is collected by cardiac puncture from unanesthetized male New Zealand White rabbits (Whaley's Summit View Farms, Belvedere, N.J.) with the use of 3.2% sodium citrate anticoagulant (1 part of citrate/10 parts of blood). All syringes and pipets are plastic. The blood is gently mixed and immediately centrifuged at 800 rpm for 10–15 minutes at room temperature to recover the platelet rich plasma (PRP). Platelet poor plasma (PPP) is prepared by centrifuging PRP at 2800 rpm for 10 minutes at room temperature.

Dilutions (1:3000) of PRP in Isoton ® diluent are made and platelet counts are determined on a Coulter Thrombocounter which is standardized with platelet reference standards (Interscience Platelet Control, Portland, Oreg.). PRP platelet counts are adjusted to approximately 400,000–500,000 platelets/$\mu$l by the addition of PPP.

L-PAF (Platelet Activating Factor) is obtained from Calbiochem. A stock solution of 1–2 E-3M is prepared in 10% ethanol in water or 100% methanol and serial working dilutions are made using saline. 1–2 E-3M stock solutions of test compounds are prepared in 100% methanol and serially diluted in PBS. All solutions are made up in plastic tubes, stored on ice and protected from heat and light. Solutions are prepared fresh or frozen at $-20°$ C. and used within 48 hours.

Incubation mixtures consisted of 400 $\mu$l PRP, 50 $\mu$l of saline diluent or test compound and 50 $\mu$l of PAF agonist. More specifically, 400 $\mu$l of PRP is stabilized in a cuvette for 1–2 minutes at 37° C. in the aggregometer to achieve a stable baseline, then 50 $\mu$l of saline or test compound is added and incubated for 5 minutes before addition of the challenge concentration of PAF. A submaximal concentration is determined from the dose response curve for PAF for that experiment. In general, the challenge concentration is 5E-8 or 1E-7M. Aggregation is monitored for 5 minutes. Samples containing test compound or diluent are run simultaneously for comparison. Test compounds are initially evaluated at a screening concentration of 1E-5M. Those producing $\geq$50% inhibition of the magnitude of aggregation at 1E-5M are then reevaluated at several final concentrations ranging from 1E-8M to 5E-5M and IC50 values are determined from the dose response curve.

The recording equipment consists of a dual channel Chronolog aggregometer connected to a dual channel 10 MV full scale deflection Omniscribe chart recorder (Houston Instruments). The chart recorder is calibrated daily with the use of a suspension of Bio-Rad latex beads (S-X 12 400 mesh) which has a density slightly greater than rabbit PRP. The bead suspension is used to set the 0% light transmission mark and clear water is used to set the 100% light transmission mark. These limits defined a full scale deflection. The aggregation traces are analyzed by a digitizing method (C. Kohler and B. Zoltan, J. Pharm. Methods, 12, 113, 1984) with x, y coordinate data stored in a computer file. A suitable program computes parameters of interest such as the magnitude of aggregation.

The results of tests on representative compounds of this invention appear in Table I.

TABLE I

In Vitro PAF Antagonism: Inhibition of pAF Induced Platelet Aggregation In Rabbit Platelet Rich Plasma

| Compound | Dose (M)[a] | % INH[b] | IC$_{50}$ (M)[c] | PAF Chall Conc (M) |
|---|---|---|---|---|
| 3-[[3-[[[4-(tetradecyloxy) phenyl]acetyl]amino]phenyl] methyl]thiazolium bromide | .00001 | 98.0 | 1.200E-07 | 5E-9 |
| | .000001 | 93.0 | | 5.0000E-08 |
| | .0000025 | 97.0 | | 5.0000E-08 |
| | .000001 | 62.0 | 6.200E-07 | 5.0000E-08 |
| | .00001 | 100.0 | 1.000E-08 | 5.0000E-08 |
| | .00001 | 100.0 | 2.800E-07 | 5.0000E-08 |
| 2,3-dimethyl-1-[4-[[[4-(tetra-decyloxy)phenyl]acetyl]amino] phenyl]1H-imidazolium iodide | .00001 | 62.0 | 4.510E-06 | 5.0000E-08 |
| 2,3-dimethyl-1-[3-[[[4-(tetra-decyloxy)phenyl]acetyl]amino] phenyl]1H-imidazolium iodide | .00001 | 80.0 | 2.470E-06 | 5.0000E-08 |
| N-[3-(2-methyl-1H-imidazol-1-yl)phenyl]-4-(tetradecyloxy)-benzeneacetamide monohydrochloride | .00001 | 34.0 | | 5.0000E-08 |
| | .00001 | 39.0 | 1.860E-05 | 5.0000E-08 |
| 5-methyl-3-[[3-[[[3-(tetra-decyloxy)phenyl]acetyl]amino] phenyl]methyl]thiazolium bromide | .00001 | 100.0 | 1.060E-06 | 5E-9 |
| | .00001 | 27.0 | | 5.0000E-08 |
| | .00001 | 100.0 | 4.900E-07 | 5.0000E-08 |
| | .00001 | 89.0 | 1.270E-06 | 5.0000E-08 |
| 5-methyl-3-[[2-[[[3-(tetra-decyloxy)phenyl]acetyl]amino]-phenyl]methyl]thiazolium bromide | .00001 | 27.0 | 3.400E-05 | 5E-9 |
| | .00001 | 23.0 | | 5.0000E-08 |
| 3-[[3-[acetyl[2-[4-(tetra-decyloxy)phenyl]ethyl]amino] phenyl]methyl]-5-methyl-thiazolium bromide | .00001 | 85.0 | 2.910E-06 | 8.0000E-09 |
| | .00001 | 69.0 | 4.300E-06 | .0000005 |
| 3-[[2-[[[4-(hexadecyloxy) phenoxy]acetyl]amino]phenyl] methyl]-5-methyl-thiazolium bromide | .00001 | 60.0 | 1.120E-05 | 1.0000E-08 |
| | .00001 | 83.0 | 3.800E-06 | .0000005 |
| 3-[[3-[[[4-(hexadecyloxy) phenoxy]acetyl]amino]phenyl] methyl]-5-methyl-thiazolium bromide | .00001 | 93.0 | 4.400E-06 | 1.0000E-08 |
| | .00001 | 72.0 | 5.000E-06 | 5.0000E-08 |
| 5-methyl-3-[[3-[[4-(tetra-decyloxy)benzoyl]amino]phenyl] methyl]-thiazolium bromide | .00001 | 54.0 | 5.970E-06 | 5.0000E-08 |
| 3-[[3-[acetyl[[4-(tetradecyl-oxy)phenyl]methyl]amino]-phenyl]methyl]-5-methyl-thiazolium bromide | .00001 | 98.0 | 5.400E-07 | 5.0000E-08 |
| | .00001 | 100.0 | 5.000E-08 | 5.0000E-08 |
| | .00001 | 90.0 | 2.000E-07 | 5.0000E-08 |
| 5-methyl-3-[[4-[[[4-(tetra-decyloxy)phenyl]acetyl]amino]-phenyl]methyl]-thiazolium bromide | .00001 | 92.0 | 1.800E-07 | 5.0000E-08 |
| | .00001 | 100.0 | 3.200E-07 | 5.0000E-08 |
| | .00001 | 92.0 | 1.300E-06 | 5.0000E-08 |
| 5-methyl-3-[[3-[[[4-(tetra-decyloxy)phenyl]amino]car-bonyl]phenyl]methyl]-thiazolium bromide | .00001 | 89.0 | 2.700E-06 | 5.0000E-08 |
| 5-methyl-3-[[3-[[[[4-(tetra-decyloxy)phenyl]amino]carbonyl] amino]phenyl]methyl]-thiazolium bromide | .00001 | 92.0 | 1.500E-06 | 5.0000E-08 |
| | .00005 | 80.0 | 1.690E-05 | .0000001 |
| 3-methyl-2-[3-[[[4-(tetra-decyloxy)phenyl]acetyl]amino] phenyl]-thiazolium chloride | .00001 | 46.0 | 1.200E-05 | 5.0000E-08 |
| 5-methyl-3-[[3-[[(methylamino) carbonyl-[[4-(tetradecyloxy) phenyl]methyl]amino]phenyl] methyl]-thiazolium bromide | .00001 | 90.0 | 4.600E-07 | 5.0000E-08 |
| | .00001 | 95.0 | 1.090E-06 | .0000001 |
| 3-[[4-[acetyl[[4-(tetradecyl-oxy)phenyl]methyl]amino] phenyl]methyl]-5-methyl-thiazolium bromide | .00001 | 84.0 | 2.100E-06 | 5.0000E-08 |
| 1-[[3-[acetyl[[4-(tetradecyl-oxy)phenyl]methyl]amino] phenyl]methyl]-3,4-dimethyl-pyridinium bromide | .00001 | 52.0 | 1.200E-05 | 5.0000E-08 |
| 3,5-dimethyl-1-[[3-[[[4-(tetra-decyloxy)phenyl]acetyl]amino] phenyl]methyl]-pyridinium bromide | .00001 | 84.0 | | 5.0000E-08 |
| 2-[[3-[[[4-(tetradecyloxy) phenyl]acetyl]amino]phenyl] methyl-imidazo[1,5-a]phenyl | .00001 | 91.0 | 1.500E-06 | 5.0000E-08 |

TABLE I-continued

In Vitro PAF Antagonism:
Inhibition of pAF Induced Platelet Aggregation
In Rabbit Platelet Rich Plasma

| Compound | Dose (M)[a] | % INH[b] | IC$_{50}$ (M)[c] | PAF Chall Conc (M) |
|---|---|---|---|---|
| bromide | | | | |

[a] = dose of compound that gives the indicated % inhibition.

[b] = the % inhibition of PAF induced platelet aggregation.

[c] = the molar concentration of compound that will inhibit 50% of the platelet aggregation induced by PAF given at the indicated PAF challenge concentration.

A. PAF Induced Lethality in Mice

PAF given I.V. to mice causes an immediate hypotensive shock leading to death in 1 hour or less. Compounds are given intraperitoneally or P.O. at various times before the PAF challenge. Animals alive after 2 hours are counted and the activity of test compounds expressed as % survival corrected for any control (saline treated) animals which survived the PAF challenge. Results of this assay appear in Table II.

TABLE II

Effect of Compound Given I.V. or P.O. in Protecting Mice from a Lethal Challenge of PAF[a]

| Compound | Dose (P.O.) mg/kg | Dose (I.V.) mg/kg | % Survival |
|---|---|---|---|
| Control (saline only) | — | — | 10% |
| 5-methyl-3-[[3-[[[3-(tetradecyloxy)phenyl]-acetyl]amino]phenyl]methyl]-thiazolium bromide | 20 | — | 59% |
| | 10 | — | — |
| | 5 | — | 40% |
| 3-[[3-[acetyl[[4-(tetra-decyloxy)phenyl]methyl]-amino]phenyl]methyl]-5-methyl-thiazolium bromide | 20 | — | 75% |
| | 10 | — | 75% |
| | 5 | — | 52% |
| 3-[[3-[acetyl[[4-(tetra-decyloxy)phenyl]methyl]-amino]phenyl]methyl]-5-methyl-thiazolium bromide | — | 1 | 83% |
| | — | .5 | 83% |
| | — | .25 | 100% |
| 5-methyl-3-[[4-[[[4-(tetradecyloxy)phenyl]-acetyl]amino]phenyl]methyl]-thiazolium bromide | 20 | — | 32% |
| | 5 | — | 32% |
| 3-[[3-[[[4-(tetradecyloxy)-phenyl]acetyl]amino]phenyl]-methyl]thiazolium bromide | 40 | — | 40% |

[a] lethal challenge of PAF is 150 μg/kg IV.

B. Endotoxin Induced Shock and Mortality in Mice

Endotoxin administration produces a shock-like state characterized by vascular permeability changes, hypotension, neutropenia, thrombocytopenia, multiple organ damage and death. The major mediators released after endotoxin injection are TNF (tumor necrosis factor), PAF (platelet activating factor) and LL-1 (interleukin I). PAF administration mimics the signs and symptoms of endotoxin induced shock and death and endotoxin also induces the release of PAF. Therefore, the effects of endotoxin should be blocked with a PAF antagonist.

Male Balb/c mice (approximately 20 g) are obtained from Charles River Laboratories and used after a one-two week acclimation period. Animals are given (ip) test compound dissolved in saline or water (sonicated and heated) at different time intervals prior to and after the ip injection of endotoxin (usually 2 hours before LPS endotoxin, and 3-4 hours after). Sigma E. Coli endotoxin, 0111:B4, phenol extraction, catalog #L2630 is used for these studies.

For the acute lethality test, the endotoxin dose is determined from dose-response titrations and adjusted to a dose that is lethal for 80–90% (LD$_{80}$–LD$_{90}$) of the mice within a 24 hour period. This LD value is approximately 50 mg/kg i.p. The number of survivors in each group (control or treated with test compound) is recorded after 24, 48 or 72 hours and the treated groups (receiving test compound and endotoxin) are compared with the untreated, control group (receiving endotoxin only) or saline control (receiving saline and endotoxin).

For the chronic endotoxin shock model, a lower dose of endotoxin is administered (generally 15 to 20 mg/kg i.p). This dose gives an LD$_{80}$ in two to four days following LPS administration. Test compounds are given 2 hours before LPS and 3-4 hours after on the first day, followed by 3 or 4 consecutive days of BID dosing. The number of survivors in each group is recorded each day for a period of 5 to 7 days.

One of the test compounds, 5-methyl-3-[[3-[[[3-(tetradecyloxy)phenyl]acetyl]amino]phenyl]methyl]-thiazolium bromide, known to be a PAF antagonist from in vitro platelet aggregation studies, when administered ip prior to a lethal ip injection of endotoxin (Table 2) did show some activity (Table 3). Several of the test compounds (PAF antagonists) are efficacious in the chronic, lower dose LPS model when administered i.p. BID daily for several days. (Table 4).

TABLE 3

Effect of Compounds Given I.P. in High Dose Acute Mouse Endotoxemia

| Treatment | Days % Survival | | | | |
|---|---|---|---|---|---|
| | 0 | 1 | 2 | 3 | 4 |
| Saline Control | 30/30(100%) | 6/30(20%) | 6/30(20%) | 6/30(20%) | 6/30(20%) |
| 5-methyl-3-[[3-[[[3-(tetra-decyloxy)phenyl]acetyl] amino]phenyl]methyl] thiazolium bromide | 30/30(100%) | 12/30(40%) | 4/30(13%) | 3/30(10%) | 3/30(10%) |

LPS Endotoxin challenge = 50 mg/kg ip

Test cpd given 2 hrs. before and 3-4 hrs. after LPS challenge on day 0, followed by BID dosing for 3-4 days.

TABLE 4

| Treatment | Effect of Compounds Given i.p. in Low Dose, Chronic Mouse Endotoxemia Days No Surv./tot. (% Survival) | | | | | | | |
|---|---|---|---|---|---|---|---|---|
| | 0 | 1 | 2 | 3 | 4 | 5 | 6 | 7 |
| None | 30/30(100) | 18/30(60) | 10/30(33) | 10/30(33) | 10/30(33) | 10/30(33) | 10/30(33) | 10/30(33) |
| Saline | 30/30(100) | 22/30(73) | 12/30(40) | 9/30(30) | 9/30(30) | 9/30(30) | 9/30(30) | 9/30(30) |
| See *1 * | 30/30(100) | 27/30(90) | 13/30(43) | 12/30(40) | 12/30(40) | 12/30(40) | 12/30(40) | 12/30(40) |
| # | 30/30(100) | 25/30(83) | 20/30(66) | 19/30(63) | 19/30(63) | 19/30(63) | 19/30(63) | 19/30(63) |
| None | 30/30(100) | 7/30(23) | 5/30(16) | 4/30(13) | 4/30(13) | 4/30(13) | 4/30(13) | |
| Saline | 30/30(100) | 8/30(26) | 5/30(16) | 5/30(16) | 5/30(16) | 5/30(16) | 5/30(16) | |
| See *2 $ | 30/30(100) | 22/30(73) | 10/30(33) | 8/30(26) | 7/30(23) | 7/30(23) | 7/30(23) | |
| None | 30/30(100) | 15/30(50) | 8/30(26) | 7/30(23) | 7/30(23) | 7/30(23) | 7/30(23) | 7/30(23) |
| Saline | 30/30(100) | 22/30(73) | 11/30(36) | 10/30(33) | 10/30(33) | 10/30(33) | 10/30(33) | 10/30(33) |
| See *3 # | 30/30(100) | 30/30(100) | 19/30(63) | 14/30(46) | 13/30(43) | 12/30(43) | 12/30(43) | 12/30(43) |
| None | 30/30(100) | 13/30(43) | 8/30(26) | 7/30(23) | 7/30(23) | 7/30(23) | 7/30(23) | |
| Saline | 30/30(100) | 11/30(36) | 7/30(23) | 4/30(13) | 4/30(13) | 4/30(13) | 4/30(13) | |
| See *4 & | 30/30(100) | 27/30(90) | 18/30(60) | 18/30(60) | 18/30(60) | 18/30(60) | 17/30(56) | |
| && | 30/30(100) | 30/30(100) | 24/30(80) | 24/30(80) | 24/30(80) | 24/30(80) | 24/30(80) | |
| None | 30/30(100) | 19/30(63) | 5/30(16) | 3/30(10) | 3/30(10) | 3/30(10) | 3/30(10) | 3/30(10) |
| Saline | 30/30(100) | 20/30(66) | 4/30(13) | 4/30(13) | 4/30(13) | 4/30(13) | 4/30(13) | 4/30(13) |
| See *5 @ | 30/30(100) | 27/30(90) | 7/30(23) | 6/30(20) | 6/30(20) | 6/30(20) | 6/30(20) | 6/30(20) |
| @@ | 30/30(100) | 24/30(80) | 14/30(46) | 14/30(46) | 14/30(46) | 14/30(46) | 14/30(46) | 14/30(46) |

*1 = 3-[[3-[[[4-(tetradecyloxy)phenyl]acetyl]amino]phenyl]methyl]thiazolium bromide
* = Dose 20 mg/kg
# = Dose 10 mg/kg
*2 = 3-[[3-[acetyl[[4-(tetradecyloxy)phenyl]methyl]amino]phenyl]methyl]-5-methyl-thiazolium bromide
$ = Dose 10 mg/kg
*3 = 5-methyl-3-[[3-[[[3-(tetradecyloxy)phenyl]acetyl]amino]phenyl]methyl]thiazolium bromide
# = Dose 10 mg/kg
*4 = 5-methyl-3-[[4-[[[4-(tetradecyloxy)phenyl]acetyl]amino]phenyl]methyl]-thiazolium bromide
& = Dose 20 mg/kg
&& = Dose 10 mg/kg
*5 = 5-methyl-3-[[3-[[(methylamino)carbonyl]-[[4-(tetradecyloxy)phenyl]methyl]amino]phenyl]methyl]thiazolium bromide
@ = Dose 20 mg/kg
@@ = Dose 10 mg/kg
All mice challenged with LPS endotoxin = 20 mg/kg i.p.
CL test cpd given 2 hours before and 3–4 hours after LPS challenge on day 0, followed by BID dosing for 3–4 days.

In addition to the utilities described hereinabove, many of the compounds of this invention are useful in the preparation of other compounds of this invention.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to this invention are prepared so that an oral dosage unit contains between about 1 and 250 mg of active compound.

The tablets, capsules and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to active ingredient, sucrose as a sweetening agent, methyl and propylparabens as preservatives, a dye and flavoring such as cherry or orange flavor.

These active Compounds may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of this invention may also be administered directly to the airways in the form of an aerosol.

The invention will be further described by the following examples.

EXAMPLE 1

Methyl p-(tetradecyloxy)phenyl acetate

A mixture of 102 g of methyl 4-hydroxyphenyl acetate, 170.2 g of tetradecyl bromide and 93.3 g of potassium carbonate in 1,000 ml of acetone is refluxed for 24 hours. Another 33.9 g of potassium carbonate is added and reflux continued for an additional 24 hours. An additional 33.9 g of potassium carbonate is added and reflux continued for another 24 hours. The mixture is filtered and the filtrate evaporated to a residue which is partitioned between ether and dilute sodium hydroxide. The organic layer is dried and evaporated to a residue which is crystallized from hexane to give 170.1 g of the desired product as a white solid, m.p. 36°–38° C.

EXAMPLE 2 p-Tetradecyloxyphenylacetic acid

A mixture of 30 g of methyl p-(tetradecyloxy)phenyl acetate, 13.93 g of potassium hydroxide, 15 ml of water and 300 ml of ethyl alcohol is refluxed for 18 hours. The ethyl alcohol is evaporated and the residue is acidified with hydrochloric acid followed by ether extraction. The organic layer is dried and evaporated to a residue which is crystallized from carbon tetrachloride:hexane to give 23.7 g of the desired product as a white solid, m.p. 84°–86° C.

EXAMPLE 3 p-Tetradecyloxyphenylacetyl chloride

A mixture of 21.7 g of p-tetradecyloxyphenylacetic acid and 11.85 g of oxalyl chloride, 45.5 mg of N,N-dimethylformamide and 250 ml of methylene chloride is stirred at ambient temperature for 24 hours. The solvent is removed by evaporation and the residue is dissolved in ether and filtered through diatomaceous earth. The filtrate is evaporated to give 22.3 g of the desired product as a white solid.

EXAMPLE 4

Ethyl 3-[[[4-(tetradecyloxy)phenyl]acetyl]amino]-benzoate

A solution of 10.13 g of ethyl 3-amino-benzoate and 6.82 g of triethylamine in 100 ml of methylene 35 chloride is added dropwise to a solution of p-tetradecyloxyphenylacetyl chloride in 100 ml of methylene chloride over 15 minutes. The mixture is stirred for an additional 2.5 hours then washed with dilute hydrochloric acid. The organic layer is evaporated and the residue dissolved in 1.5 liter of ether then washed with dilute sodium hydroxide. The organic layer is dried and evaporated to a residue which is crystallized from carbon tetrachloride:hexane to give 24.4 g of the desired product as a white solid, m.p. 91°–94° C.

EXAMPLE 5

N-[3-Hydroxymethyl)phenyl]-4-(tetradecyloxy)benzeneacetamide

To a suspension of ethyl 3-[[[4-(tetradecyloxy)phenyl]acetyl]amino]benzoate in ether is added 1.85 g of lithium borohydride and 2.71 g of methyl alcohol. The mixture is refluxed for 2.5 hours followed by the slow addition of water and dilute hydrochloric acid. The mixture is extracted with ether:tetrahydrofuran, dried and evaporated to a residue which is crystallized from carbon tetrachloride to give 8.4 g of the desired product as a white powder, m.p. 120°–125° C.

EXAMPLE 6

N-[3-(Bromomethyl)phenyl]-4-(tetradecyloxy)-benzeneacetamide

To a stirred solution of 4.0 g of N-[3-hydroxymethyl)-phenyl]-4-(tetradecyloxy)-benzeneacetamide in 100 ml of tetrahydrofuran is added 1.19 g of triethylamine followed by 1.34 g of methanesulfonyl chloride. Also added is 7.66 g of lithium bromide and continued stirring for 24 hours. The solvent is removed under vacuum and the residue is partitioned between chloroform and water followed by an additional wash of the organic layer with saturated sodium bicarbonate. The organic layer is dried and filtered through a pad of silica gel. The filtrate is evaporated to a residue which is crystallized from hexane:carbon tetrachloride to give 4.1 g of the desired product as a white powder, m.p. 116°–118° C.

EXAMPLE 7

5-Methyl-3-[[3-[[[4-(tetradecyloxy)phenyl]acetyl]amino]phenyl]methyl]thiazolium bromide A mixture of 3.6 g of N-[3-(bromomethyl)-phenyl]-4-(tetradecyloxy)benzeneacetamide and 3.46 g of 5-methylthiazole in 25 ml of toluene is refluxed under inert gas for 1.5 hours, cooled and poured into 200 ml of ether. The organic layer is decanted and the solid washed with ether and collected to give 3.8 g of the desired product as a white solid, m.p. 173°–175° C.

EXAMPLE 8

N-[4-(Hydroxymethyl)phenyl]-4-tetradecyloxy)-benzeneacetamide

A solution of 3.4 g of 4-aminobenzyl alcohol in 100 ml of methylene chloride containing 6.72 g of pyridine is cooled to 0° C. and a solution of 7.8 g of p-tetradecyloxyphenylacetyl chloride in 100 ml of methylene chloride added with stirring over 30 minutes. Stirring is continued at ambient temperature over 4 hours. The mixture is diluted with 300 ml of chloroform and water added. The mixture is heated to dissolve the solids then the organic layer is washed with dilute hydrochloric acid, dried and filtered through a pad of silica gel. The filtrate is concentrated to about 200 ml on a steam bath and 25 ml of hexanes added. The mixture is cooled and filtered to give 4.8 g of the desired product as a white solid, m.p. 135°–147° C.

EXAMPLE 9

N-[4-(Bromomethyl)phenyl]-4-tetradecyloxy)-benzeneacetamide

To a solution of 4.5 g of N-[4-(hydroxymethyl)-phenyl]-4-tetradecyloxy)benzeneacetamide in 100 ml of tetrahydrofuran is added 1.36 g of methanesulfonyl chloride and 1.2 g of triethylamine followed by stirring for four hours at ambient temperature. The mixture is poured into water and extracted with ether. The organic layer is washed with saturated sodium bicarbonate, dried and filtered through a small pad of silica gel. The filtrate is evaporated and the residue crystallized from carbon tetrachloride:hexane to give 3.9 g of off-white solid, m.p. 110°–115° C.

EXAMPLE 10

5-Methyl-3-[(4-[[[4-(tetradecyloxy]phenyl]acetyl]amino]phenyl]methyl]thiazolium bromide A mixture of 3.5 g of N-[4-(bromomethyl)phenyl]-4-(tetradecyloxy)benzeneacetamide and 2.69 g of 5-methylthiazole in 45 ml of toluene is refluxed under argon for 6 hours, then allowed to stand at ambient temperature overnight. The mixture is diluted with ether then evaporated to a residue which is dissolved in hot tetrahydrofuran and again diluted with ether. The solid is collected by centrifugation and washed with ether several times then dried under vacuum to give 1.9 g of the product as a white powder, m.p. 120°–125° C.

EXAMPLE 11

N-[(2-Hydroxymethyl)phenyl]-4-(tetradecyloxy)benzeneacetamide

To a solution of p-tetradecyloxyphenylacetyl chloride in 110 ml of tetrahydrofuran is added a solution of 3.52 g of O-aminobenzyl alcohol and 9.05 g of pyridine in 100 ml of tetrahydrofuran followed by stirring at ambient temperature overnight. The tetrahydrofuran is evaporated to a residue which is dissolved in chloroform then washed with dilute hydrochloric acid and saturated sodium bicarbonate. The organic layer is dried and filtered through a pad of magnesium silicate. The filtrate is evaporated to a residue which is crystallized from carbon tetrachloride to give 10.3 g of the desired product as a white solid, m.p. 112°–115° C.

EXAMPLE 12

N-[2-(Bromomethyl)phenyl]-4-(tetradecyloxy)benzeneacetamide

To a solution of 5 g of N-[(2-hydroxymethyl)phenyl]-4-(tetradecyloxy)benzeneacetamide in 80 ml of tetrahydrofuran is added 1.68 g of methanesulfonyl chloride and 1.48 g of triethylamine followed by stirring for 30 minutes. Added 9.57 g of lithium bromide and continued stirring for 2 hours. The mixture is poured into water and extracted with warm ethyl acetate. The organic layer is washed with saturated sodium bicarbonate, dried and evaporated to a residue which is crystallized from hexanes:carbon tetrachloride to give 3.6 g of the desired product as a white solid, m.p. 100°–103° C.

EXAMPLE 13

5-Methyl-3-[[2-[[[4-(tetradecyloxy)phenyl]acetyl]amino]phenyl]methyl]thiazolium bromide A mixture of 3.0 g of N-[2-(bromomethyl)phenyl]-4-(tetradecyloxy)benzeneacetamide and 2.88 g of 5-methylthiazole in 25 ml of toluene is heated at reflux under argon for 2.5 hours. The mixture is poured into 200 ml of ether, cooled, the solid collected, washed with ether and dried to give 3.2 g of the desired product as a white powder, m.p. 124°–127° C.

EXAMPLE 14

3-(Tetradecyloxy)benzeneacetic acid, methyl ester

A mixture of 46.5 g of 3-hydroxybenzeneacetic acid methyl ester, 77.6 g n-tetradecyl bromide and 42.54 g of potassium carbonate in 500 ml of acetone is refluxed for 24 hours. Another 15.5 g of potassium carbonate is added and reflux continued for another 24 hours. An additional 15.5 g of potassium carbonate is added and reflux continued for another 24 hours. The mixture is filtered and the filtrate evaporated to a residue which is poured into water and extracted with ether. The organic layer is dried and evaporated to a residue which is crystallized from hexane to give 45 g of the desired product as a white solid, m.p. 31°–33° C.

EXAMPLE 15 m-Tetradecyloxyphenylacetic acid

A mixture of 40.5 g of 3-(tetradecyloxy)benzeneacetic acid, methyl ester, 18.8 g of potassium hydroxide, 15 ml of water and 300 ml of ethyl alcohol is refluxed for 4 hours. The solvent is removed and the residue partitioned between chloroform and dilute hydrochloric acid. The organic layer is dried and evaporated to a residue which is crystallized from carbon tetrachloride:hexane to give 31.8 g of the desired product as a white solid.

EXAMPLE 16

3-(Tetradecyloxy)benzeneacetyl chloride

A mixture of 20 g of m-tetradecyloxyphenylacetic acid, 10.93 g of oxalyl chloride and 41.95 mg of N,N-dimethylformamide in 250 ml of methylene chloride is stirred at ambient temperature for 5 hours. The solvent is removed and the concentrate dissolved in 1:1 ether:hexane and filtered through diatomaceous earth. The filtrate is evaporated to give 21.3 g of the desired product as a light yellow solid.

EXAMPLE 17

N-[3-(Hydroxymethyl)phenyl]-3-tetradecyloxy)benzeneacetamide

To a solution of 10.5 g of 3-(tetradecyloxy)benzeneacetyl chloride in 110 ml of tetrahydrofuran is added a solution of m-aminobenzyl alcohol in 110 ml of tetrahydrofuran containing 9.05 g of pyridine followed by stirring at ambient temperature for 4 hours and storing in a refrigerator over the weekend. The solvent is evaporated and the residue is poured into water and extracted with tetrahydrofuran:ether. The organic layer is washed with dilute hydrochloric acid, dried and filtered through a pad of magnesium silicate. The filtrate is evaporated and the residue purified by high pressure liquid chromatography using 2:1 hexane:ethyl acetate to give 3.6 g of the desired product as a white powder, m.p. 108°–110° C. and 5.8 g of a white powder, m.p. 86°–90° C. found to be 3-(tetradecyloxy)-[3-[[[3-(tetradecyloxy)phenyl]acetyl]amino]phenyl]benzeneacetic acid methyl ester.

EXAMPLE 18

N-[3-(Bromomethyl)phenyl]-3-(tetradecyloxy)benzeneacetamide

To a solution of 3.3 g of N-[3-(hydroxymethyl)phenyl]-3-(tetradecyloxy)benzeneacetamide in 60 ml of tetrahydrofuran is added 1.11 g of methanesulfonyl chloride and 978.95 mg of triethylamine followed by stirring at ambient temperature for 2 hours. Added 6.32 g of lithium bromide and stirred for an additional 2.5 hours. The reaction is poured into a mixture of saturated sodium chloride and saturated sodium bicarbonate then extracted with ether. The organic layer is dried and evaporated to give the desired product as a white solid, m.p. 104°–106° C.

EXAMPLE 19

5-Methyl-3-[[3-[[[3-(tetradecyloxy)phenyl]acetyl]amino]phenyl]methyl]thiazolium bromide A mixture of 4 g of N-[3-(bromomethyl)phenyl]-3-(tetradecyloxy)benzeneacetamide and 3.84 g of 5-methylthiazole in 40 ml of toluene is refluxed for 1.5 hours under argon, cooled and the solvent evaporated to a residue. The residue is mixed with ether and the solid collected by centrifugation. The solid is washed several times with ether then dried by vacuum to give 4.3 g of the desired product as an off white powder, m.p. 125°–130° C.

EXAMPLE 20

N-[2-(Hydroxymethyl)phenyl]-3-(tetradecyloxy)benzeneacetamide

To a solution of 3.52 g of O-aminobenzyl alcohol and 9.05 g of pyridine in 110 ml of methylene chloride at 0° C. is added a solution of 10.5 g of m-tetradecyloxyphenylacetyl chloride in 110 ml of methylene chloride over 30 minutes. Stirring is continued at ambient temperature for 2 hours. The mixture is washed several times with dilute hydrochloric acid and dried. The solvent is evaporated and the residue crystallized from carbon tetrachloride to give 7.7 g of the desired product as a white solid, m.p. 100°-103° C.

EXAMPLE 21

N-[2-(Bromomethyl)phenyl]-3-(tetradecyloxy)benzeneacetamide

To a solution of 4 g of N-[2-(hydroxymethyl)phenyl]-3-(tetradecyloxy)benzeneacetamide in 75 ml of tetrahydrofuran is added 1.19 g of triethylamine and 1.34 g of methanesulfonyl chloride, followed by stirring at room temperature for 1.5 hours. Added 7.66 g of lithium bromide with stirring continued for an additional 2.5 hours. The solvent is evaporated and the residue partitioned between chloroform and saturated sodium bicarbonate. The organic layer is dried and evaporated to a residue which is crystallized from hexane to give 2.6 g of the desired product as a white solid, m.p. 103°-106° C.

EXAMPLE 22

5-Methyl-3-[[2-[[[3-(tetradecyloxy)phenyl]acetyl]amino]phenyl]methyl]thiazolium bromide A mixture of 2.3 g of N-[2-(bromomethyl)phenyl]-3-(tetradecyloxy)benzeneacetamide and 2.21 g of 5-methylthiazole in 40 ml of toluene is refluxed for 2.5 hours under argon. The solvent is evaporated to a residue which is mixed with ether and the resulting solid collected by centrifugation, washed with ether then dried to give 2.7 g of the desired product as a white powder, m.p. 94°-100° C.

According to the methods outlined hereinabove in Flowsheet A and described in detail in Examples 1-22, the compounds of this invention listed hereinbelow in List 1 can be prepared. These methods are applicable to the preparation of the compounds of this invention by one skilled in the art.

List 1

3-[[2-[[[-4-(tetradecyloxy)phenyl]acetyl]amino]Phenyl]methyl]thiazolium bromide

3-[[2-[[[-3-(tetradecyloxy)phenyl]acetyl]amino)phenyl]methyl]thiazolium bromide

3-[[2-[[[-2-(tetradecyloxy)phenyl]acetyl]amino]phenyl]methyl]thiazolium bromide

3-[[2-[[[3-chloro-4-(tetradecyloxy)phenyl]acetyl]amino]phenyl]methyl]thiazolium bromide 3-[[2-[[[3-fluoro-2-(tetradecyloxy)phenyl)acetyl]amino)phenyl]methyl]thiazolium bromide 3-[[2-[[[3-acetyl-4-(tetradecyloxy)phenyl]acetyl]amino]phenyl]methyl]thiazolium bromide 3-[[2-[[[3-acetyl-2-(tetradecyloxy)phenyl]acetyl]amino]phenyl]methyl]thiazolium bromide 3-[[2-[[[3-t-butyl-4-(tetradecyloxy)phenyl]acetyl]amino]phenyl]methyl]thiazolium bromide 3-[[2-[[[3-t-butyl-2-(tetradecyloxy)phenyl]acetyl]amino]phenyl]methyl]thiazolium bromide 3-[[2-[[[3-methoxy-4-(tetradecyloxy)phenyl]acetyl]amino]phenyl]methyl]thiazolium bromide 3-[[2-[[[3-methoxy-2-(tetradecyloxy)phenyl]acetyl]amino]phenyl]methyl]thiazolium bromide 3-[[2-[[[2-chloro-4-(tetradecyloxy)phenyl]acetyl]amino]phenyl]methyl]thiazolium bromide 3-[[2-[[[4-chloro-3-(tetradecyloxy)phenyl]acetyl]amino]phenyl]methyl]thiazolium bromide 3-[[2-[[[4-t-butyl-2-(tetradecyloxy)phenyl]acetyl]amino]phenyl]methyl]thiazolium bromide 3-[[2-[[[4-methoxy-3-(tetradecyloxy)phenyl]acetyl]amino]phenyl]methyl]thiazolium bromide 3-[[2-[[[4-methoxy-2-(tetradecyloxy)phenyl]acetyl]amino]phenyl]methyl]thiazolium bromide 3-[[3-[[[-4-(tetradecyloxy)phenyl]acetyl]amino]phenyl]methyl]thiazolium bromide 3-[[3-[[[-3-(tetradecyloxy)phenyl]acetyl]amino]phenyl]methyl]thiazolium bromide 3-[[3-[[[3-chloro-2-(tetradecyloxy)phenyl]acetyl]amino]phenyl]methyl]thiazolium bromide 3-[[3-[[[3-fluoro-4-(tetradecyloxy)phenyl]acetyl]amino]phenyl]methyl]thiazolium bromide 3-[[3-[[[3-fluoro-2-(tetradecyloxy)phenyl]acetyl]amino]phenyl]methyl]thiazolium bromide 3-[[3-[[[3-acetyl-4-(tetradecyloxy)phenyl]acetyl]amino]phenyl]methyl]thiazolium bromide 3-[[3-[[[3-acetyl-2-(tetradecyloxy)phenyl]acetyl]amino]phenyl]methyl]thiazolium bromide 3-[[3-[[[3-t-butyl-4-(tetradecyloxy)phenyl]acetyl]amino]phenyl]methyl]thiazolium bromide 3-[[3-[[[3-t-butyl-2-(tetradecyloxy)phenyl]acetyl]amino]phenyl]methyl]thiazolium bromide 3-[[3-[[[3-methoxy-4-(tetradecyloxy)phenyl]acetyl]amino]phenyl]methyl]thiazolium bromide 3-[[3-[[[3-methoxy-2-(tetradecyloxy)phenyl]acetyl]amino]phenyl]methyl]thiazolium bromide 3-[[3-[[[2-chloro-4-(tetradecyloxy)phenyl]acetyl]amino]phenyl]methyl]thiazolium bromide 3-[[3-[[[4-t-butyl-3-(tetradecyloxy)phenyl]acetyl]amino]phenyl]methyl]thiazolium bromide 3-[[3-[[[4-t-butyl-2-(tetradecyloxy)phenyl]acetyl]amino]phenyl]methyl]thiazolium bromide 3-[[3-[[[4-methoxy-3-(tetradecyloxy)phenyl]acetyl]amino]phenyl]methyl]thiazolium bromide 3-[[4-[[[-4-(tetradecyloxy)phenyl]acetyl]amino]phenyl]methyl]thiazolium bromide 3-[[4-[[[-4-(hexadecyloxy)phenyl]acetyl]amino]phenyl]methyl]thiazolium bromide 3-[[4-[[[-3-(tetradecyloxy)phenyl]acetyl]amino]phenyl]methyl]thiazolium bromide 3-[[4-[[[-3-(hexadecyloxy)phenyl]acetyl]amino]phenyl]methyl]thiazolium bromide 3-[[4-[[[-2-(tetradecyloxy)phenyl]acetyl]amino]phenyl]methyl]thiazolium bromide 3-[[4-[[[-2-(hexadecyloxy)phenyl]acetyl]amino]phenyl]methyl]thiazolium bromide 3-[[4-[[[3-chloro-4-(tetradecyloxy)phenyl]acetyl]amino]phenyl]methyl]thiazolium bromide 3-[[4-[[[3-chloro-4-(hexadecyloxy)phenyl]acetyl]amino]phenyl]methyl]thiazolium bromide 3-[[4-[[[3-chloro-2-(tetradecyloxy)phenyl]acetyl]amino]phenyl]methyl]thiazolium bromide 3-[[4-[[[3-fluoro-4-(tetradecyloxy)phenyl]acetyl]amino]phenyl]methyl]thiazolium bromide 3-[[4-[[[3-fluoro-4-(hexadecyloxy)phenyl]acetyl]amino]phenyl]methyl]thiazolium bromide 3-[[4-[[[3-fluoro-2-(tetradecyloxy)phenyl]acetyl-]amino]phenyl]methyl]thiazolium bromide
3-[[4-[[[3-acetyl-4-(tetradecyloxy)phenyl]acetyl]amino]-phenyl]methyl]thiazolium bromide
3-[[4-[[[3-acetyl-4-(hexadecyloxy)phenyl]acetyl]amino]-phenyl]methyl]thiazolium bromide
3-[[4-[[[3-acetyl-2-(tetradecyloxy)phenyl]acetyl]amino]-phenyl]methyl]thiazolium bromide
3-[[4-[[[3-acetyl-2-(hexadecyloxy)phenyl]acetyl]amino]-phenyl]methyl]thiazolium bromide
3-[[4-[[[3-t-butyl-4-(tetradecyloxy)phenyl]acetyl-]amino]phenyl]methyl]thiazolium bromide
3-[[4-[[[3-t-butyl-4-(hexadecyloxy)phenyl]acetyl-]amino]phenyl]methyl]thiazolium bromide
3-[[4-[[[3-t-butyl-2-(tetradecyloxy)phenyl]acetyl-]amino]phenyl]methyl]thiazolium bromide
3-[[4-[[[3-methoxy-4-(hexadecyloxy)phenyl]acetyl-]amino]phenyl]methyl]thiazolium bromide
3-[[4-[[[3-methoxy-2-(tetradecyloxy)phenyl]acetyl-]amino]phenyl]methyl]thiazolium bromide
3-[[4-[[[3-methoxy-2-(hexadecyloxy)phenyl]acetyl-]amino]phenyl]methyl]thiazolium bromide
3-[[4-[[[2-chloro-4-(tetradecyloxy)phenyl]acetyl-]amino]phenyl]methyl]thiazolium bromide
3-[[4-[[[2-chloro-4-(hexadecyloxy)phenyl]acetyl-]amino]phenyl]methyl]thiazolium bromide
3-[[4-[[[4-chloro-3-(tetradecyloxy)phenyl]acetyl-]amino]phenyl]methyl]thiazolium bromide
3-[[4-[[[4-chloro-3-(hexadecyloxy)phenyl]acetyl-]amino]phenyl]methyl]thiazolium bromide
3-[[4-[[[4-chloro-2-(tetradecyloxy)phenyl]acetyl-]amino]phenyl]methyl]thiazolium bromide
3-[[4-[[[4-t-butyl-3-(tetradecyloxy)phenyl]acetyl-]amino]phenyl]methyl]thiazolium bromide
3-[[4-[[[4-t-butyl-3-(hexadecyloxy)phenyl]acetyl-]amino]phenyl]methyl]thiazolium bromide
3-[[4-[[[4-t-butyl-2-(tetradecyloxy)phenyl]acetyl-]amino]phenyl]methyl]thiazolium bromide
3-[[4-[[[4-t-butyl-2-(hexadecyloxy)phenyl]acetyl-]amino]phenyl]methyl]thiazolium bromide
3-[[4-[[[4-methoxy-3-(tetradecyloxy)phenyl]acetyl-]amino]phenyl ]methyl]thiazolium bromide
3-[[4-[[[4-methoxy-3-(hexadecyloxy)phenyl]acetyl-]amino]phenyl]methyl]thiazolium bromide
5-Methyl-3-[[2-[[[-4-(tetradecyloxy)phenyl]acetyl-]amino]phenyl]methyl]thiazolium bromide
5-Methyl-3-[[2-[[[-3-(tetradecyloxy)phenyl]acetyl-]amino]phenyl]methyl]thiazolium bromide
5-Methyl-3-[[2-[[[-2-(tetradecyloxy)phenyl]acetyl-]amino]phenyl]methyl]thiazolium bromide
5-Methyl-3-[[2-[[[-3-chloro-4-(tetradecyloxy)phenyl-]acetyl]amino]phenyl]methyl]thiazolium bromide
5-Methyl-3-[[2-[[[3-chloro-2-(tetradecyloxy)phenyl-]acetyl]amino]phenyl]methyl]thiazolium bromide
5-Methyl-3-[[2-[[[3-fluoro-4-(tetradecyloxy)phenyl-]acetyl]amino]phenyl]methyl]thiazolium bromide
5-Methyl-3-[[2-[[[3-fluoro-2-(tetradecyloxy)phenyl-]acetyl]amino]phenyl]methyl]thiazolium bromide
5-Methyl-3-[[2-[[[3-acetyl-2-(tetradecyloxy)phenyl-]acetyl]amino]phenyl]methyl]thiazolium bromide
5-Methyl-3-[[2-[[[3-t-butyl-4-(tetradecyloxy)phenyl-]acetyl]amino]phenyl]methyl]thiazolium bromide
5-Methyl-3-[[2-[[[3-t-butyl-2-(tetradecyloxy)phenyl-]acetyl]amino]phenyl]methyl]thiazolium bromide
5-Methyl-3-[[2-[[[3-methoxy-4-(tetradecyloxy)phenyl-]acetyl]amino]phenyl]methyl]thiazolium bromide
5-Methyl-3-[[2-[[[3-methoxy-2-(tetradecyloxy)phenyl-]acetyl]amino]phenyl]methyl]thiazolium bromide
5-Methyl-3-[[2-[[[2-chloro-4-(tetradecyloxy)phenyl-]acetyl]amino]phenyl]methyl]thiazolium bromide
5-Methyl-3-[[2-[[[4-chloro-3-(tetradecyloxy)phenyl-]acetyl]amino]phenyl]methyl]thiazolium bromide
5-Methyl-3-[[2-[[[4-t-butyl-2-(tetradecyloxy)phenyl-]acetyl]amino]phenyl]methyl]thiazolium bromide
5-Methyl-3-[[2-[[[4-methoxy-3-(tetradecyloxy)phenyl-]acetyl]amino]phenyl]methyl]thiazolium bromide
5-Methyl-3-[[2-[[[4-methoxy-2-(tetradecyloxy)phenyl-]acetyl]amino]phenyl]methyl]thiazolium bromide
5-Methyl-3-[[3-[[[-4-(tetradecyloxy)phenyl]acetyl-]amino]phenyl]methyl]thiazolium bromide
5-Methyl-3-[[3-[[[-4-(dodecyloxy)phenyl]acetyl]amino]-phenyl]methyl]thiazolium bromide
5-Methyl-3-[[3-[[[-3-(tetradecyloxy)phenyl]acetyl-]amino]phenyl]methyl]thiazolium bromide
5-Methyl-3-[[3-[[[-3-(dodecyloxy)phenyl]acetyl]amino]-phenyl]methyl]thiazolium bromide
5-Methyl-3-[[3-[[[-2-(tetradecyloxy)phenyl]acetyl-]amino]phenyl]methyl]thiazolium bromide
5-Methyl-3-[[3-[[[-2-(dodecyloxy)phenyl]acetyl]amino]-phenyl]methyl]thiazolium bromide
5-Methyl-3-[[3-[[[3-chloro-2-(tetradecyloxy)phenyl-]acetyl]amino]phenyl]methyl]thiazolium bromide
5-Methyl-3-[[3-[[[3-chloro-2-(dodecyloxy)phenyl-]acetyl]amino]phenyl]methyl]thiazolium bromide
5-Methyl-3-[[3-[[[3-fluoro-4-(tetradecyloxy)phenyl-]acetyl]amino]phenyl]methyl]thiazolium bromide
5-Methyl-3-[[3-[[[3-fluoro-4-(dodecyloxy)phenyl-]acetyl]amino]phenyl]methyl]thiazolium bromide
5-Methyl-3-[[3-[[[3-fluoro-2-(tetradecyloxy)phenyl-]acetyl]amino]phenyl]methyl]thiazolium bromide
5-Methyl-3-[[3-[[[3-fluoro-2-(dodecyloxy)phenyl-]acetyl]amino]phenyl]methyl]thiazolium bromide
5-Methyl-3-[[3-[[[3-acetyl-4-(tetradecyloxy)phenyl-]acetyl]amino]phenyl]methyl]thiazolium bromide
5-Methyl-3-[[3-[[[3-acetyl-4-(dodecyloxy)phenyl-]acetyl]amino]phenyl]methyl]thiazolium bromide
5-Methyl-3-[[3-[[[3-acetyl-2-(tetradecyloxy)phenyl-]acetyl]amino]phenyl]methyl]thiazolium bromide.
5-Methyl-3-[[3-[[[3-t-butyl-4-(dodecyloxy)phenyl-]acetyl]amino]phenyl]methyl]thiazolium bromide
5-Methyl-3-[[3-[[[3-t-butyl-2-(tetradecyloxy)phenyl-]acetyl]amino]phenyl]methyl]thiazolium bromide
5-Methyl-3-[[3-[[[3-t-butyl-2-(dodecyloxy)phenyl-]acetyl]amino]phenyl]methyl]thiazolium bromide
5-Methyl-3-[[3-[[[3-methoxy-4-(tetradecyloxy)phenyl-]acetyl]amino]phenyl]methyl]thiazolium bromide
5-Methyl-3-[[3-[[[3-methoxy-4-(dodecyloxy)phenyl-]acetyl]amino]phenyl]methyl]thiazolium bromide
5-Methyl-3-[[3-[[[3-methoxy-2-(tetradecyloxy)phenyl-]acetyl]amino]phenyl]methyl]thiazolium bromide
5-Methyl-3-[[3-[[[3-methoxy-2-(dodecyloxy)phenyl-]acetyl]amino]phenyl]methyl]thiazolium bromide
5-Methyl-3-[[3-[[[2-chloro-4-(tetradecyloxy)phenyl-]acetyl]amino]phenyl]methyl]thiazolium bromide
5-Methyl-3-[[3-[[[4-chloro-3-(dodecyloxy)phenyl-]acetyl]amino]phenyl]methyl]thiazolium bromide
5-Methyl-3-[[3-[[[4-chloro-2-(tetradecyloxy)phenyl-]acetyl]amino]phenyl]methyl]thiazolium bromide
5-Methyl-3-[[3-[[[4-chloro-2-(dodecyloxy)phenyl-]acetyl]amino]phenyl]methyl]thiazolium bromide
5-Methyl-3-[[3-[[[4-t-butyl-3-(decyloxy)phenyl]acetyl-]amino]phenyl]methyl]thiazolium bromide
5-Methyl-3-[[3-[[[4-t-butyl-3-(dodecyloxy)phenyl-]acetyl]amino]phenyl]methyl]thiazolium bromide
5-Methyl-3-[[3-[[[4-t-butyl-2-(tetradecyloxy)phenyl-]acetyl]amino]phenyl]methyl]thiazolium bromide 5-Methyl-3-[[3-[[[4-t-butyl-2-(dodecyloxy)phenyl]acetyl]amino]phenyl]methyl]thiazolium bromide
5-Methyl-3-[[3-[[[4-methoxy-3-(tetradecyloxy)phenyl]acetyl]amino]phenyl]methyl]thiazolium bromide
5-Methyl-3-[[3-[[[4-methoxy-3-(dodecyloxy)phenyl]acetyl]amino]phenyl]methyl]thiazolium bromide
5-Methyl-3-[[3-[[[4-methoxy-2-(tetradecyloxy)phenyl]acetyl]amino]phenyl]methyl]thiazolium bromide
5-Methyl-3-[[3-[[[4-methoxy-2-(dodecyloxy)phenyl]acetyl]amino]phenyl]methyl]thiazolium bromide
5-Methyl-3-[[4-[[[-4-(tetradecyloxy)phenyl]acetyl]amino]phenyl]methyl]thiazolium bromide
5-Methyl-3-[[4-[[[-3-(tetradecyloxy)phenyl]acetyl]amino]phenyl]methyl]thiazolium bromide
5-Methyl-3-[[4-[[[-2-(tetradecyloxy)phenyl]acetyl]amino]phenyl]methyl]thiazolium bromide
5-Methyl-3-[[4 -[[[3-chloro-4-(tetradecyloxy)phenyl]acetyl]amino]phenyl]methyl]thiazolium bromide
5-Methyl-3-[[4-[[[3-fluoro-2-(tetradecyloxy)phenyl]acetyl]amino]phenyl]methyl]thiazolium bromide
5-Methyl-3-[[4-[[[3-acetyl-4-(tetradecyloxy)phenyl]acetyl]amino]phenyl]methyl]thiazolium bromide
5-Methyl-3-[[4-[[[3-acetyl-2-(tetradecyloxy)phenyl]acetyl]amino]phenyl]methyl]thiazolium bromide
5-Methyl-3-[[4-[[[3-t-butyl-4-(tetradecyloxy)phenyl]acetyl]amino]phenyl]methyl]thiazolium bromide
5-Methyl-3-[[4-[[[3-t-butyl-2-(tetradecyloxy)phenyl]acetyl]amino]phenyl]methyl]thiazolium bromide
5-Methyl-3-[[4-[[[3-methoxy-4-(tetradecyloxy)phenyl]acetyl]amino]phenyl]methyl]thiazolium bromide
5-Methyl-3-[[4-[[[3-methoxy-2-(tetradecyloxy)phenyl]acetyl]amino]phenyl]methyl]thiazolium bromide
5-Methyl-3-[[4-[[[2-chloro-4-(tetradecyloxy)phenyl]acetyl]amino]phenyl]methyl]thiazolium bromide
5-Methyl-3-[[4-[[[4-chloro-3-(tetradecyloxy)phenyl]acetyl]amino]phenyl]methyl]thiazolium bromide
5-Methyl-3-[[4-[[[4-chloro-2-(tetradecyloxy)phenyl]acetyl]amino]phenyl]methyl]thiazolium bromide
5-Methyl-3-[[4-[[[4-t-butyl-3-(tetradecyloxy)phenyl]acetyl]amino]phenyl]methyl]thiazolium bromide
5-Methyl-3-[[4-[[[4-t-butyl-2-(tetradecyloxy)phenyl]acetyl]amino]phenyl]methyl]thiazolium bromide
5-Methyl-3-[[4-[[[4-methoxy-3-(tetradecyloxy)phenyl]acetyl]amino]phenyl]methyl]thiazolium bromide
5-Methyl-3-[[4-[[[4-methoxy-2-(tetradecyloxy)phenyl]acetyl]amino]phenyl]methyl]thiazolium bromide
2-Methyl-3-[[2-[[[-4-(tetradecyloxy)phenyl]acetyl]amino]phenyl]methyl]thiazolium bromide
2-Methyl-3-[[2-[[[3-chloro-4-(tetradecyloxy)phenyl]acetyl]amino]phenyl]methyl]thiazolium bromide
2-Methyl-3-[[2-[[[3-chloro-2-(tetradecyloxy)phenyl]acetyl]amino]phenyl]methyl]thiazolium bromide
2-Methyl-3-[[2-[[[3-fluoro-4-(tetradecyloxy)phenyl]acetyl]amino]phenyl]methyl]thiazolium bromide
2-Methyl-3-[[2-[[[3-fluoro-2-(tetradecyloxy)phenyl]acetyl]amino]phenyl]methyl]thiazolium bromide
2-Methyl-3-[[2-[[[3-acetyl-4-(tetradecyloxy)phenyl]acetyl]amino]phenyl]methyl]thiazolium bromide
2-Methyl-3-[[2-[[[3-acetyl-2-(tetradecyloxy)phenyl]acetyl]amino]phenyl]methyl]thiazolium bromide
2-Methyl-3-[[2-[[[3-t-butyl-4-(tetradecyloxy)phenyl]acetyl]amino]phenyl]methyl]thiazolium bromide
2-Methyl-3-[[2-[[[3-t-butyl-2-(tetradecyloxy)phenyl]acetyl]amino]phenyl]methyl]thiazolium bromide
2-Methyl-3-[[2-[[[3-methoxy-4-(tetradecyloxy)phenyl]acetyl]amino]phenyl]methyl]thiazolium bromide
2-Methyl-3-[[2-[[[3-methoxy-2-(tetradecyloxy)phenyl]acetyl]amino]phenyl]methyl]thiazolium bromide
2-Methyl-3-[[2-[[[2-chloro-4-(tetradecyloxy)phenyl]acetyl]amino]phenyl]methyl]thiazolium bromide
2-Methyl-3-[[2-[[[4-chloro-3-(tetradecyloxy)phenyl]acetyl]amino]phenyl]methyl]thiazolium bromide
2-Methyl-3-[[2-[[[4-chloro-2-(tetradecyloxy)phenyl]acetyl]amino]phenyl]methyl]thiazolium bromide
2-Methyl-3-[[2-[[[4-t-butyl-3-(tetradecyloxy)phenyl]acetyl]amino]phenyl]methyl]thiazolium bromide
2-Methyl-3-[[2-[[[4-methoxy-2-(tetradecyloxy)phenyl]acetyl]amino]phenyl]methyl]thiazolium bromide
2-Methyl-3-[[3-[[[-4-(tetradecyloxy)phenyl]acetyl]amino]phenyl]methyl]thiazolium bromide
2-Methyl-3-[[3-[[[-3-(tetradecyloxy)phenyl]acetyl]amino]phenyl]methyl]thiazolium bromide
2-Methyl-3-[[3-[[[-2-(tetradecyloxy)phenyl]acetyl]amino]phenyl]methyl]thiazolium bromide
2-Methyl-3-[[3-[[[3-chloro-4-(tetradecyloxy)phenyl]acetyl]amino]phenyl]methyl]thiazolium bromide
2-Methyl-3-[[3-[[[3-chloro-2-(tetradecyloxy)phenyl]acetyl]amino]phenyl]methyl]thiazolium bromide
2-Methyl-3-[[3-[[[3-fluoro-4-(tetradecyloxy)phenyl]acetyl]amino]phenyl]methyl]thiazolium bromide
2-Methyl-3-[[3-[[[3-fluoro-2-(tetradecyloxy)phenyl]acetyl]amino]phenyl]methyl]thiazolium bromide
2-Methyl-3-[[3-[[[3-acetyl-4-(tetradecyloxy)phenyl]acetyl]amino]phenyl]methyl]thiazolium bromide
2-Methyl-3-[[3-[[[3-acetyl-2-(tetradecyloxy)phenyl]acetyl]amino]phenyl]methyl]thiazolium bromide
2-Methyl-3-[[3-[[[3-t-butyl-4-(tetradecyloxy)phenyl]acetyl]amino]phenyl]methyl]thiazolium bromide
2-Methyl-3-[[3-[[[3-t-butyl-2-(tetradecyloxy)phenyl]acetyl]amino]phenyl]methyl]thiazolium bromide
2-Methyl-3-[[3-[[[3-methoxy-4-(tetradecyloxy)phenyl]acetyl]amino]phenyl]methyl]thiazolium bromide
2-Methyl-3-[[3-[[[3-methoxy-2-(tetradecyloxy)phenyl]acetyl]amino]phenyl]methyl]thiazolium bromide
2-Methyl-3-[[3-[[[2-chloro-4-(tetradecyloxy)phenyl]acetyl]amino]phenyl]methyl]thiazolium bromide
2-Methyl-3-[[3-[[[4-t-butyl-3-(tetradecyloxy)phenyl]acetyl]amino]phenyl]methyl]thiazolium bromide
2-Methyl-3-([3-[[[4-t-butyl-2-(tetradecyloxy)phenyl])acetyl]amino]phenyl]methyl]thiazolium bromide
2-Methyl-3-[[3-[[[4-methoxy-3-(tetradecyloxy)phenyl]acetyl]amino]phenyl]methyl]thiazolium bromide
2-Methyl-3-[[3-[[[4-methoxy-2-(tetradecyloxy)phenyl]acetyl]amino]phenyl]methyl]thiazolium bromide
2-Methyl-3-[[4-[[[-4-(tetradecyloxy)phenyl]acetyl]amino]phenyl]methyl]thiazolium bromide
2-Methyl-3-([4-([(-3-(tetradecyloxy)phenyl]acetyl]amino]phenyl]methyl]thiazolium bromide
2-Methyl-3-[[4-[[[-2-(tetradecyloxy)phenyl]acetyl]amino]phenyl]methyl]thiazolium bromide
2-Methyl-3-[[4-[[[3-chloro-4-(tetradecyloxy)phenyl]acetyl]amino]phenyl]methyl]thiazolium bromide
2-Methyl-3-[[4-[[[3-chloro-2-(tetradecyloxy)phenyl]acetyl]amino]phenyl]methyl]thiazolium bromide
2-Methyl-3-[[4-[[[3-fluoro-4-(tetradecyloxy)phenyl]acetyl]amino]phenyl]methyl]thiazolium bromide
2-Methyl-3-[[4-[[[3-fluoro-2-(tetradecyloxy)phenyl]acetyl]amino]phenyl]methyl]thiazolium bromide
2-Methyl-3-[[4-[[[3-acetyl-4-(tetradecyloxy)phenyl]acetyl]amino]phenyl]methyl]thiazolium bromide
2-Methyl-3-[[4-[[[3-acetyl-2-(tetradecyloxy)phenyl]acetyl]amino]phenyl]methyl]thiazolium bromide
2-Methyl-3-[[4-[[[3-methoxy-4-(tetradecyloxy)phenyl]acetyl]amino]phenyl]methyl]thiazolium bromide
2-Methyl-3-[[4-[[[3-methoxy-2-(decyloxy)phenyl]acetyl]amino]phenyl]methyl]thiazolium bromide 2-Methyl-3-[[4-[[[2-chloro-4-(tetradecyloxy)phenyl]acetyl]amino]phenyl]methyl]thiazolium bromide
2-Methyl-3-[[4-[[[4-chloro-3-(tetradecyloxy)phenyl]acetyl]amino]phenyl]methyl]thiazolium bromide
2-Methyl-3-[[4-[[[4-chloro-2-(tetradecyloxy)phenyl]acetyl]amino]phenyl]methyl]thiazolium bromide
2-Methyl-3-[[4-[[[4-t-butyl-3-(tetradecyloxy)phenyl]acetyl]amino]phenyl]methyl]thiazolium bromide
2-Methyl-3-[[4-[[[4-t-butyl-2-(tetradecyloxy)phenyl]acetyl]amino]phenyl]methyl]thiazolium bromide
2-Methyl-3-[[4-[[[4-methoxy-3-(tetradecyloxy)phenyl]acetyl]amino]phenyl]methyl]thiazolium bromide
2-Methyl-3-[[4-[[[4-methoxy-2-(tetradecyloxy)phenyl]acetyl]amino]phenyl]methyl]thiazolium bromide
4-Methyl-3-[[2-[[[-4-(tetradecyloxy)phenyl]acetyl]amino]phenyl]methyl]thiazolium bromide
4-Methyl-3-[[2-[[[-3-(tetradecyloxy)phenyl]acetyl]amino]phenyl]methyl]thiazolium bromide
4-Methyl-3-[[2-[[[-2-(tetradecyloxy)phenyl]acetyl]amino]phenyl]methyl]thiazolium bromide
4-Methyl-3-[[2-[[[3-chloro-4-(tetradecyloxy)phenyl]acetyl]amino]phenyl]methyl]thiazolium bromide
4-Methyl-3-[[2-[[[3-chloro-2-(tetradecyloxy)phenyl]acetyl]amino]phenyl]methyl]thiazolium bromide
4-Methyl-3-[[2-[[[3-fluoro-4-(tetradecyloxy)phenyl]acetyl]amino]phenyl]methyl]thiazolium bromide
4-Methyl-3-[[2-[[[3-fluoro-2-(tetradecyloxy)phenyl]acetyl]amino]phenyl]methyl]thiazolium bromide
4-Methyl-3-[[2-[[[3-acetyl-4-(tetradecyloxy)phenyl]acetyl]amino]phenyl]methyl]thiazolium bromide
4-Methyl-3-[[2-[[[3-acetyl-2-(tetradecyloxy)phenyl]acetyl]amino]phenyl]methyl]thiazolium bromide
4-Methyl-3-[[2-[[[3-t-butyl-4-(tetradecyloxy)phenyl]acetyl]amino]phenyl]methyl]thiazolium bromide
4-Methyl-3-[[2-[[[3-t-butyl-2-(tetradecyloxy)phenyl]acetyl]amino]phenyl]methyl]thiazolium bromide
4-Methyl-3-[[2-[[[3-methoxy-4-(tetradecyloxy)phenyl]acetyl]amino]phenyl]methyl]thiazolium bromide
4-Methyl-3-[[2-[[[3-methoxy-2-(tetradecyloxy)phenyl]acetyl]amino]phenyl]methyl]thiazolium bromide
4-Methyl-3-[[2-[[[2-chloro-4-(tetradecyloxy)phenyl]acetyl]amino]phenyl]methyl]thiazolium bromide
4-Methyl-3-[[2-[[[4-chloro-3-(tetradecyloxy)phenyl]acetyl]amino]phenyl]methyl]thiazolium bromide
4-Methyl-3-[[2-[[[4-chloro-2-(tetradecyloxy)phenyl]acetyl]amino]phenyl]methyl]thiazolium bromide
4-Methyl-3-[[2-[[[4-t-butyl-3-(tetradecyloxy)phenyl]acetyl]amino]phenyl]methyl]thiazolium bromide
4-Methyl-3-[[2-[[[4-t-butyl-2-(tetradecyloxy)phenyl]acetyl]amino]phenyl]methyl]thiazolium bromide
4-Methyl-3-[[2-[[[4-methoxy-3-(tetradecyloxy)phenyl]acetyl]amino]phenyl]methyl]thiazolium bromide
4-Methyl-3-[[2-[[[4-methoxy-2-(tetradecyloxy)phenyl]acetyl]amino]phenyl]methyl]thiazolium bromide
4-Methyl-3-[[3-[[[-4-(tetradecyloxy)phenyl]acetyl]amino]phenyl]methyl]thiazolium bromide
4-Methyl-3-[[3-[[[-3-(tetradecyloxy)phenyl]acetyl]amino]phenyl]methyl]thiazolium bromide
4-Methyl-3-[[3-[[[-2-(tetradecyloxy)phenyl]acetyl]amino]phenyl]methyl]thiazolium bromide
4-Methyl-3-[[3-[[[3-chloro-4-(octyloxy)phenyl]acetyl]amino]phenyl]methyl]thiazolium bromide
4-Methyl-3-[[3-[[[3-chloro-2-(tetradecyloxy)phenyl]acetyl]amino]phenyl]methyl]thiazolium bromide
4-Methyl-3-[[3-[[[3-fluoro-4-(tetradecyloxy)phenyl]acetyl]amino]phenyl]methyl]thiazolium bromide
4-Methyl-3-[[3-[[[3-fluoro-2-(tetradecyloxy)phenyl]acetyl]amino]phenyl]methyl]thiazolium bromide
4-Methyl-3-[[3-[[[3-acetyl-4-(tetradecyloxy)phenyl]acetyl]amino]phenyl]methyl]thiazolium bromide
4-Methyl-3-[[3-[[[3-acetyl-2-(tetradecyloxy)phenyl]acetyl]amino]phenyl]methyl]thiazolium bromide
4-Methyl-3-[[3-[[[3-t-butyl-4-(decyloxy)phenyl]acetyl]amino]phenyl]methyl]thiazolium bromide
4-Methyl-3-[[3-[[[3-t-butyl-2-(tetradecyloxy)phenyl]acetyl]amino]phenyl]methyl]thiazolium bromide
4-Methyl-3-[[3-[[[3-methoxy-2-(tetradecyloxy)phenyl]acetyl]amino]phenyl]methyl]thiazolium bromide
4-Methyl-3-[[3-[[[2-chloro-4-(tetradecyloxy)phenyl]acetyl]amino]phenyl]methyl]thiazolium bromide
4-Methyl-3-[[3-[[[4-chloro-3-(tetradecyloxy)phenyl]acetyl]amino]phenyl]methyl]thiazolium bromide
4-Methyl-3-[[3-[[[4-chloro-2-(tetradecyloxy)phenyl]acetyl]amino]phenyl]methyl]thiazolium bromide
4-Methyl-3-[[3-[[[4-t-butyl-3-(tetradecyloxy)phenyl]acetyl]amino]phenyl]methyl]thiazolium bromide
4-Methyl-3-[[3-[[[4-t-butyl-2-(tetradecyloxy)phenyl]acetyl]amino]phenyl]methyl]thiazolium bromide
4-Methyl-3-[[3-[[[4-methoxy-3-(tetradecyloxy)phenyl]acetyl]amino]phenyl]methyl]thiazolium bromide
4-Methyl-3-[[4-[[[-3-(tetradecyloxy)phenyl]acetyl]amino]phenyl]methyl]thiazolium bromide
4-Methyl-3-[[4-[[[-2-(tetradecyloxy)phenyl]acetyl]amino]phenyl]methyl]thiazolium bromide
4-Methyl-3-[[4-[[[3-chloro-4-(tetradecyloxy)phenyl]acetyl]amino]phenyl]methyl]thiazolium bromide
4-Methyl-3-[[4-[[[3-chloro-2-(tetradecyloxy)phenyl]acetyl]amino]phenyl]methyl]thiazolium bromide
4-Methyl-3-[[4-[[[3-fluoro-4-(tetradecyloxy)phenyl]acetyl]amino]phenyl]methyl]thiazolium bromide
4-Methyl-3-[[4-[[[3-acetyl-4-(tetradecyloxy)phenyl]acetyl]amino]phenyl]methyl]thiazolium bromide
4-Methyl-3-[[4-[[[3-acetyl-2-(tetradecyloxy)phenyl]acetyl]amino]phenyl]methyl]thiazolium bromide
4-Methyl-3-[[4-[[[3-t-butyl-4-(tetradecyloxy)phenyl]acetyl]amino]phenyl]methyl]thiazolium bromide
4-Methyl-3-[[4-[[[3-t-butyl-2-(tetradecyloxy)phenyl]acetyl]amino]phenyl]methyl]thiazolium bromide
4-Methyl-3-[[4-[[[3-methoxy-4-(tetradecyloxy)phenyl]acetyl]amino]phenyl]methyl]thiazolium bromide
4-Methyl-3-[[4-[[[3-methoxy-2-(tetradecyloxy)phenyl]acetyl]amino]phenyl]methyl]thiazolium bromide
4-Methyl-3-[[4-[[[2-chloro-4-(tetradecyloxy)phenyl]acetyl]amino]phenyl]methyl]thiazolium bromide
4-Methyl-3-[[4-[[[4-chloro-3-(dodecyloxy)phenyl]acetyl]amino]phenyl]methyl]thiazolium bromide
4-Methyl-3-[[4-[[[4-chloro-2-(tetradecyloxy)phenyl]acetyl]amino]phenyl]methyl]thiazolium bromide
4-Methyl-3-[[4-[[[4-t-butyl-2-(tetradecyloxy)phenyl]acetyl]amino]phenyl]methyl]thiazolium bromide
4-Methyl-3-[[4-[[[4-methoxy-3-(tetradecyloxy)phenyl]acetyl]amino]phenyl]methyl]thiazolium bromide
4-Methyl-3-[[4-[[[4-methoxy-2-(hexadecyloxy)phenyl]acetyl]amino]phenyl]methyl]thiazolium bromide

EXAMPLE 23

Methyl p-(tetradecyloxy)benzoate

A well stirred mixture of 100 g of methyl 4-hydroxybenzoate, 182.25 g of tetradecylbromide, 136.26 g of potassium carbonate and 4.93 g of sodium iodide in 1-liter of acetone is refluxed for 48 hours. The mixture is poured into ice water, the solid collected and washed with water. The solid is dissolved in chloroform and washed with 1N sodium hydroxide, dried and evaporated to a residue which is crystallized from hexanes to give 18.5 g of the desired product as a white solid, m.p. 64°–66° C.

EXAMPLE 24 p-(Tetradecyloxy)benzoic acid

A mixture of 120 g of methyl p-(tetradecyloxy)benzoate, 57.96 g of potassium hydroxide, 1-liter of methyl alcohol, 400 ml of ethyl alcohol and 60 ml of water is refluxed for 4.5 hours. A solid is formed and the reaction mixture partitioned between dilute hydrochloric acid and chloroform with some warming. The organic layer is washed with warm dilute hydrochloric acid and dried. The filtrate is evaporated to a volume of 600 ml and an equal volume of hexanes added to form a solid which is dried to give 104 g of the desired product as a white solid, m.p. 94°–96° C.

EXAMPLE 25 p-Tetradecyloxybenzoyl chloride

A mixture of 50 g of p-(tetradecyloxy)benzoic acid and 28.46 g of oxalyl chloride in 500 ml of chloroform containing 10 drops of N,N-dimethylformamide is stirred for 18 hours at ambient temperature. The solvent is evaporated and the residue dissolved in ether, filtered and evaporated to give 54 g of the desired product as a white solid.

EXAMPLE 26

N-[3-(Hydroxymethyl)phenyl]-4-(tetradecyloxy)benzamide

To a solution of 8.17 g of m-aminobenzyl alcohol and 16.14 g of pyridine in 200 ml of methylene chloride is added at 0° C. over 30 minutes a solution of 18 g of p-tetradecyloxybenzoyl chloride in 200 ml of methylene chloride. Stirring is continued for another 6 hours. An additional 400 ml of chloroform and water is added followed by warming to dissolve all the solids. The warm organic layer is separated and washed with dilute hydrochloric acid and saturated sodium bicarbonate. The warm organic layer is dried and filtered. The filtrate is diluted with an equal volume of hexane and cooled in a refrigerator overnight. The resulting solid is collected and air dried to give 18.4 g of the desired product as a white solid, m.p. 112°–115° C.

EXAMPLE 27

N-[3-(Bromomethyl)phenyl]-4-(tetradecyloxy)benzamide

To a solution of N-[3-(hydroxymethyl)phenyl]-4-(tetradecyloxy)benzamide and 3.47 g of methanesulfonyl chloride in 200 ml of tetrahydrofuran is added 3.07 g of triethylamine followed by stirring at ambient temperature for 2 hours. Also added is 21.93 g of lithium bromide followed by stirring at ambient temperature for an additional 3 hours. The mixture is poured into water and extracted with ether. The organic layer is washed with a mixture of brine and saturated sodium bicarbonate then dried. The solvent is removed under vacuum and the residue crystallized from carbon tetrachloride:-hexanes to give the desired product as a white solid, m.p. 116°–118° C.

EXAMPLE 28

5-Methyl-3-[[3-[[4.-tetradecyloxy)benzoyl]amino]phenyl]methyl]thiazolium bromide A mixture of 4 g of N-[3-(bromomethyl)phenyl]-4-(tetradecyloxy)benzamide and 3.95 g of 5-methylthiazole in 50 ml of toluene is refluxed under argon for 4 hours. The solvent is removed and ether added to the residue. The solid is collected by centrifugation and washed several times with ether then vacuum dried to give 4.4 g of the desired product as a white powder, m.p. 188°–192° C.

According to the methods outlined hereinabove in Flowsheet A and described in detail in Examples 9–28, the compounds of this invention listed hereinbelow in List 2 can be prepared. These methods are applicable to the preparation of the compounds of this invention by one skilled in the art.

List 2

3-[[2-[[-4-(tetradecyloxy)benzoyl]amino)Phenyl]methyl]thiazolium bromide

3-[[2-[[-3-(tetradecyloxy)benzoyl]amino]Phenyl]methyl]thiazolium bromide

3-[[2-[[-2-(tetradecyloxy)benzoyl]amino]phenyl]methyl)thiazolium bromide

3-[[2-[[3-chloro-4-(tetradecyloxy)benzoyl]amino]phenyl]methyl]thiazolium bromide 3-[[2-[[3-fluoro-2-(tetradecyloxy)benzoyl]amino)phenyl]methyl)thiazolium bromide 3-[[2-[[3-t-butyl-2-(tetradecyloxy)benzoyl]amino]-Phenyl]methyl]thiazolium bromide 3-[[2-[[3-methoxy-4-(tetradecyloxy)benzoyl]amino]-Phenyl]methyl]thiazolium bromide 3-[[2-[[3-methoxy-2-(tetradecyloxy)benzoyl]amino)-Phenyl]methyl]thiazolium bromide 3-[[2-[[2-chloro-4-(tetradecyloxy)benzoyl)amino]-Phenyl]methyl)thiazolium bromide 3-[[2-[[4-chloro-3-(tetradecyloxy)benzoyl]amino]-Phenyl]methyl]thiazolium bromide 3-[[2-[[4-t-butyl-2-(tetradecyloxy)benzoyl]amino]-Phenyl]methyl]thiazolium bromide 3-[[2-[[4-methoxy-3-(tetradecyloxy)benzoyl]amino]-Phenyl]methyl)thiazolium bromide 3-[[2-[[4-methoxy-2-(tetradecyloxy)benzoyl]amino)-Phenyl]methyl]thiazolium bromide 3-[[3-[[-4-(tetradecyloxy)benzoyl]amino]Phenyl]methyl]thiazolium bromide 3-[[3-[[-3-(tetradecyloxy)benzoyl]amino]Phenyl]methyl]thiazolium bromide 3-[[3-[[3-chloro-2-(tetradecyloxy)benzoyl)amino)-Phenyl)methyl)thiazolium bromide 3-[[3-[[3-fluoro-4-(tetradecyloxy)benzoyl]amino]-Phenyl]methyl]thiazolium bromide 3-[[3-[[3-fluoro-2-(tetradecyloxy)benzoyl]amino]-Phenyl]methyl]thiazolium bromide 3-[[3-[[3-methoxy-4-(tetradecyloxy)benzoyl]amino]-Phenyl]methyl]thiazolium bromide 3-[[3-[[3-methoxy-2-(tetradecyloxy)benzoyl]amino]-phenyl]methyl]thiazolium bromide 3-[[3-[[2-chloro-4-(tetradecyloxy)benzoyl]amino]-phenyl]methyl]thiazolium bromide 3-[[3-[[4-t-butyl-3-(tetradecyloxy)benzoyl]amino]-phenyl]methyl]thiazolium bromide 3-[[3-[[4-t-butyl-2-(tetradecyloxy)benzoyl]amino]-phenyl]methyl]thiazolium bromide 3-[[3-[[4-methoxy-3-(tetradecyloxy)benzoyl]amino]-phenyl]methyl]thiazolium bromide
3-[[4-[[-4-(tetradecyloxy)benzoyl]amino]phenyl]methyl]thiazolium bromide
3-[[4-[[-4-(hexadecyloxy)benzoyl]amino]phenyl]methyl]thiazolium bromide
3-[[4-[[-3-(tetradecyloxy)benzoyl]amino]phenyl]methyl]thiazolium bromide
3-[[4-[[-3-(hexadecyloxy)benzoyl]amino]phenyl]methyl]thiazolium bromide
3-[[4-[[-2-(tetradecyloxy)benzoyl]amino]phenyl]methyl]thiazolium bromide
3-[[4-[[-2-(hexadecyloxy)benzoyl]amino]phenyl]methyl]thiazolium bromide
3-[[4-[[3-chloro-4-(tetradecyloxy)benzoyl]amino]-phenyl]methyl]thiazolium bromide
3-[[4-[[3-chloro-4-(hexadecyloxy)benzoyl]amino]-phenyl]methyl]thiazolium bromide
3-[[4-[[3-chloro-2-(tetradecyloxy)benzoyl]amino]-phenyl]methyl]thiazolium bromide
3-[[4-[[3-acetyl-2-(tetradecyloxy)benzoyl]amino]-phenyl]methyl]thiazolium bromide
3-[[4-[[3-acetyl-2-(hexadecyloxy)benzoyl]amino]-phenyl]methyl]thiazolium bromide
3-[[4-[[3-t-butyl-4-(tetradecyloxy)benzoyl]amino]-phenyl]methyl]thiazolium bromide
3-[[4-[[3-t-butyl-4-(hexadecyloxy)benzoyl]amino]-phenyl]methyl]thiazolium bromide
3-[[4-[[3-t-butyl-2-(tetradecyloxy)benzoyl]amino]-phenyl]methyl]thiazolium bromide
3-[[4-[[3-methoxy-4-(hexadecyloxy)benzoyl]amino]-phenyl]methyl]thiazolium bromide
3-[[4-[[3-methoxy-2-(tetradecyloxy)benzoyl]amino]-phenyl]methyl]thiazolium bromide
3-[[4-[[3-methoxy-2-(hexadecyloxy)benzoyl]amino]-phenyl]methyl]thiazolium bromide
3-[[4-[[2-chloro-4-(tetradecyloxy)benzoyl]amino]-Phenyl]methyl]thiazolium bromide
3-[[4-[[2-chloro-4-(hexadecyloxy)benzoyl]amino]-Phenyl]methyl]thiazolium bromide
3-[[4-[[4-chloro-3-(tetradecyloxy)benzoyl]amino]-phenyl]methyl]thiazolium bromide
3-[[4-[[4-chloro-3-(hexadecyloxy)benzoyl]amino)-Phenyl]methyl]thiazolium bromide
3-[[4-[[4-chloro-2-(tetradecyloxy)benzoyl]amino]-Phenyl]methyl]thiazolium bromide
3-[[4-[[4-t-butyl-3-(tetradecyloxy)benzoyl]amino]-Phenyl]methyl]thiazolium bromide
5-Methyl-3-[[2-[[-4-(tetradecyloxy)benzoyl)amino]-Phenyl]methyl]thiazolium bromide
5-Methyl-3-((2-((-3-(tetradecyloxy)benzoyl]amino)-Phenyl]methyl]thiazolium bromide
5-Methyl-3-[[2-[[-2-(tetradecyloxy)benzoyl]amino]-Phenyl]methyl]thiazolium bromide
5-Methyl-3-[[2-[[3-chloro-4-(tetradecyloxy)benzoyl-)amino]Phenyl]methyl]thiazolium bromide
5-Methyl-3-[[2-[[3-chloro-2-(tetradecyloxy)benzoyl-]amino]Phenyl]methyl)thiazolium bromide
5-Methyl-3-[[2-[[3-fluoro-4-(tetradecyloxy)benzoyl-]amino]phenyl]methyl]thiazolium bromide
5-Methyl-3-[[2-[[3-fluoro-2-(tetradecyloxy)benzoyl-]amino]Phenyl]methyl]thiazolium bromide
5-Methyl-3-[[2-[[3-acetyl-2-(tetradecyloxy)benzoyl-]amino]Phenyl]methyl]thiazolium bromide
5-Methyl-3-[[2-[[3-t-butyl-4-(tetradecyloxy)benzoyl-]amino]Phenyl]methyl]thiazolium bromide
5-Methyl-3-[[2-[[3-t-butyl-2-(tetradecyloxy)benzoyl-]amino) phenyl]methyl]thiazolium bromide
5-Methyl-3-[[2-[[3-methoxy-4-(tetradecyloxy)benzoyl-]amino]phenyl]methyl]thiazolium bromide
5-Methyl-3-[[2-[[3-methoxy-2-(tetradecyloxy)benzoyl-]amino]phenyl]methyl]thiazolium bromide
5-Methyl-3-[[2-[[2-chloro-4-(tetradecyloxy)benzoyl-]amino]phenyl]methyl]thiazolium bromide
5-Methyl-3-[[2-[[4-chloro-3-(tetradecyloxy)benzoyl-]amino]phenyl]methyl]thiazolium bromide
5-Methyl-3-[[2-[[4-t-butyl-2-(tetradecyloxy)benzoyl-)amino)Phenyl)methyl)thiazolium bromide
5-Methyl-3-[[2-[[4-methoxy-3-(tetradecyloxy)benzoyl-]amino]phenyl]methyl]thiazolium bromide
5-Methyl-3-[[3-[[-3-(dodecyloxy)benzoyl]amino]-phenyl]methyl]thiazolium bromide
5-Methyl-3-[[3-[[-4-(tetradecyloxy)benzoyl]amino]-phenyl]methyl]thiazolium bromide
5-Methyl-3-[[3-[[-2-(dodecyloxy)benzoyl]amino]-phenyl]methyl]thiazolium bromide
5-Methyl-3-[[3-[[3-chloro-2-(tetradecyloxy)benzoyl-]amino]phenyl]methyl]thiazolium bromide
5-Methyl-3-[[3-[[3-chloro-2-(dodecyloxy)benzoyl-]amino]phenyl]methyl]thiazolium bromide
5-Methyl-3-[[3-[[3-fluoro-4-(tetradecyloxy)benzoyl-]amino]phenyl]methyl]thiazolium bromide
5-Methyl-3-[[3-[[3-fluoro-4-(dodecyloxy)benzoyl-]amino]phenyl]methyl]thiazolium bromide
5-Methyl-3-[[3-[[3-fluoro-2-(tetradecyloxy)benzoyl-]amino]phenyl]methyl]thiazolium bromide
5-Methyl-3-[[3-[[3-fluoro-2-(dodecyloxy)benzoyl-]amino]phenyl]methyl]thiazolium bromide
5-Methyl-3-[[3-[[3-acetyl-4-(tetradecyloxy)benzoyl-]amino]phenyl]methyl]thiazolium bromide
5-Methyl-3-[[3-[[3-acetyl-4-(dodecyloxy)benzoyl-]amino]phenyl]methyl]thiazolium bromide
5-Methyl-3-[[3-[[3-acetyl-2-(tetradecyloxy)benzoyl-]amino]phenyl]methyl]thiazolium bromide
5-Methyl-3-[[3-[[3-t-butyl-4-(dodecyloxy)benzoyl-]amino]phenyl]methyl]thiazolium bromide
5-Methyl-3-[[3-[[2-chloro-4-(tetradecyloxy)benzoyl-]amino]phenyl]methyl]thiazolium bromide
5-Methyl-3-[[3-[[4-chloro-3-(dodecyloxy)benzoyl-]amino]phenyl]methyl]thiazolium bromide
5-Methyl-3-[[3-[[4-chloro-2-(tetradecyloxy)benzoyl-]amino]phenyl]methyl]thiazolium bromide
5-Methyl-3-[[3-[[4-chloro-2-(dodecyloxy)benzoyl-]amino]phenyl]methyl]thiazolium bromide
5-Methyl-3-[[3-[[4-t-butyl-3-(decyloxy)benzoyl]amino]-phenyl]methyl]thiazolium bromide
5-Methyl-3-[[3-[[4-t-butyl-3-(dodecyloxy)benzoyl-]amino]phenyl]methyl]thiazolium bromide
5-Methyl-3-[[3-[[4-t-butyl-2-(tetradecyloxy)benzoyl-]amino]phenyl]methyl]thiazolium bromide
5-Methyl-3-[[3-[[4-t-butyl-2-(dodecyloxy)benzoyl-]amino]phenyl]methyl]thiazolium bromide
5-Methyl-3-[[3-[[4-methoxy-3-(tetradecyloxy)benzoyl-]amino]phenyl]methyl]thiazolium bromide
5-Methyl-3-[[3-[[4-methoxy-3-(dodecyloxy)benzoyl-]amino]phenyl]methyl]thiazolium bromide
5-Methyl-3-[[3-[[4-methoxy-2-(tetradecyloxy)benzoyl-]amino]phenyl]methyl]thiazolium bromide
5-Methyl-3-[[3-[[4-methoxy-2-(dodecyloxy)benzoyl-]amino]phenyl]methyl]thiazolium bromide
5-Methyl-3-[[4-[[-4-(tetradecyloxy)benzoyl]amino]-phenyl]methyl]thiazolium bromide
5-Methyl-3-[[4-[[-3-(tetradecyloxy)benzoyl]amino]-phenyl]methyl]thiazolium bromide
5-Methyl-3-[[4-[[-2-(tetradecyloxy)benzoyl]amino]-phenyl]methyl]thiazolium bromide 5-Methyl-3-[[4-[[3-acetyl-4-(tetradecyloxy)benzoyl]amino]phenyl]methyl]thiazolium bromide
5-Methyl-3-[[4-[[3-acetyl-2-(tetradecyloxy)benzoyl]amino]phenyl]methyl]thiazolium bromide
5-Methyl-3-[[4-[[3-t-butyl-4-(tetradecyloxy)benzoyl]amino]phenyl]methyl]thiazolium bromide
5-Methyl-3-[[4-[[3-t-butyl-2-(tetradecyloxy)benzoyl]amino]phenyl]methyl]thiazolium bromide
5-Methyl-3-[[4-[[3-methoxy-4-(tetradecyloxy)benzoyl]amino]phenyl]methyl]thiazolium bromide
5-Methyl-3-[[4-[[3-methoxy-2-(tetradecyloxy)benzoyl]amino]phenyl]methyl]thiazolium bromide
5-Methyl-3-[[4-[[2-chloro-4-(tetradecyloxy)benzoyl]amino]phenyl]methyl]thiazolium bromide
5-Methyl-3-[[4-[[4-chloro-3-(tetradecyloxy)benzoyl]amino]phenyl]methyl]thiazolium bromide
5-Methyl-3-[[4-[[4-chloro-2-(tetradecyloxy)benzoyl]amino]phenyl]methyl]thiazolium bromide
5-Methyl-3-[[4-[[4-t-butyl-3-(tetradecyloxy)benzoyl]amino]phenyl]methyl]thiazolium bromide
5-Methyl-3-[[4-[[4-t-butyl-2-(tetradecyloxy)benzoyl]amino]phenyl]methyl]thiazolium bromide
5-Methyl-3-[[4-[[4-methoxy-3-(tetradecyloxy)benzoyl]amino]phenyl]methyl]thiazolium bromide
5-Methyl-3-[(4-[[4-methoxy-2-(tetradecyloxy)benzoyl]amino]phenyl]methyl]thiazolium bromide
2-Methyl-3-[[2-[[-4-(tetradecyloxy)benzoyl) amino]-Phenyl]methyl]thiazolium bromide
2-Methyl-3-[[2-[[3-chloro-4-(tetradecyloxy)benzoyl]amino]Phenyl]methyl]thiazolium bromide
2-Methyl-3-[[2-[[3-t-butyl-2-(tetradecyloxy)benzoyl]amino]phenyl]methyl]thiazolium bromide
2-Methyl-3-[[2-[[3-methoxy-4-(tetradecyloxy)benzoyl]amino]phenyl]methyl]thiazolium bromide
2-Methyl-3-[[2-[[3-methoxy-2-(tetradecyloxy)benzoyl]amino]phenyl]methyl]thiazolium bromide
2-Methyl-3-[[2-[[2-chloro-4-(tetradecyloxy)benzoyl]amino]Phenyl]methyl]thiazolium bromide
2-Methyl-3-[[2-[[4-chloro-3-(tetradecyloxy)benzoyl]amino]Phenyl]methyl]thiazolium bromide
2-Methyl-3-[[2-[[4-chloro-2-(tetradecyloxy)benzoyl]amino]Phenyl]methyl]thiazolium bromide
2-Methyl-3-[[2-[[4-t-butyl-3-(tetradecyloxy)benzoyl]amino]Phenyl]methyl]thiazolium bromide
2-Methyl-3-[[2-[[4-methoxy-2-(tetradecyloxy)benzoyl]amino]Phenyl]methyl]thiazolium bromide
2-Methyl-3-[[3-[[-4-(tetradecyloxy)benzoyl]amino]-Phenyl]methyl]thiazolium bromide
2-Methyl-3-[[3-[[-3-(tetradecyloxy)benzoyl]amino]-Phenyl]methyl]thiazolium bromide
2-Methyl-3-[[3-[[-2-(tetradecyloxy)benzoyl]amino]-phenyl]methyl]thiazolium bromide
2-Methyl-3-((3-([3-chloro-4-(tetradecyloxy)benzoyl]Amino)Phenyl)methyl)thiazolium bromide
2-Methyl-3-[[3-[(3-chloro-2-(tetradecyloxy)benzoyl]amino)phenyl]methyl]thiazolium bromide
2-Methyl-3-[[3-[[3-fluoro-4-(tetradecyloxy)benzoyl]amino]phenyl]methyl]thiazolium bromide
2-Methyl-3-[[3-[[3-fluoro-2-(tetradecyloxy)benzoyl]amino]phenyl]methyl]thiazolium bromide
2-Methyl-3-[[3-[[2-chloro-4-(tetradecyloxy)benzoyl]amino]phenyl]methyl]thiazolium bromide
2-Methyl-3-[[3-[[4-t-butyl-3-(tetradecyloxy)benzoyl]amino]Phenyl]methyl]thiazolium bromide
2-Methyl-3-[[3-[[4-t-butyl-2-(tetradecyloxy)benzoyl]amino]phenyl]methyl]thiazolium bromide
2-Methyl-3-[[3-[[4-methoxy-3-(tetradecyloxy) 1 benzoyl]amino]Phenyl]methyl]thiazolium bromide
2-Methyl-3-[[3-[[4-methoxy-2-(tetradecyloxy)benzoyl]amino)Phenyl]methyl]thiazolium bromide
2-Methyl-3-[[4-[[-4-(tetradecyloxy)benzoyl]amino]-Phenyl]methyl]thiazolium bromide
2-Methyl-3-[[4-[[-3-(tetradecyloxy)benzoyl]amino]-Phenyl]methyl]thiazolium bromide
2-Methyl-3-[[4-[[-2-(tetradecyloxy)benzoyl]amino]-Phenyl]methyl)thiazolium bromide
2-Methyl-3-[[4-[[3-chloro-4-(tetradecyloxy)benzoyl]amino)phenyl]methyl)thiazolium bromide
2-Methyl-3-[[4-[[3-chloro-2-(tetradecyloxy)benzoyl]amino]Phenyl]methyl]thiazolium bromide
2-Methyl-3-[[4-[[3-fluoro-4-(tetradecyloxy)benzoyl]amino)Phenyl]methyl]thiazolium bromide
2-Methyl-3-[[4-[[3-fluoro-2-(tetradecyloxy)benzoyl]amino]phenyl]methyl]thiazolium bromide
2-Methyl-3-[[4-[[3-acetyl-4-(tetradecyloxy)benzoyl]amino]phenyl]methyl]thiazolium bromide
2-Methyl-3-[[4-[[3-acetyl-2-(tetradecyloxy)benzoyl]amino]phenyl]methyl]thiazolium bromide
2-Methyl-3-[[4-[[3-methoxy-4-(tetradecyloxy)benzoyl]amino]phenyl]methyl]thiazolium bromide
2-Methyl-3-[[4-[[4-methoxy-3-(tetradecyloxy)benzoyl]amino]phenyl]methyl]thiazolium bromide
2-Methyl-3-[[4-[[4-methoxy-2-(tetradecyloxy)benzoyl]amino]phenyl]methyl]thiazolium bromide
4-Methyl-3-[[2-[[-4-(tetradecyloxy)benzoyl]amino]-phenyl]methyl]thiazolium bromide
4-Methyl-3-[[2-[[-3-(tetradecyloxy)benzoyl]amino]-phenyl]methyl]thiazolium bromide
4-Methyl-3-[[2-[[-2-(tetradecyloxy)benzoyl]amino]-phenyl]methyl]thiazolium bromide
4-Methyl-3-[[2-[[3-chloro-4-(tetradecyloxy)benzoyl]amino]phenyl]methyl]thiazolium bromide
4-Methyl-3-[[2-[[3-chloro-2-(tetradecyloxy)benzoyl]amino]phenyl]methyl]thiazolium bromide
4-Methyl-3-[[2-[[3-fluoro-4-(tetradecyloxy)benzoyl]amino]Phenyl]methyl]thiazolium bromide
benzoyl]amino[2-[[3-fluoro-2-(tetradecyloxy)o]-Phenyl]methyl]thiazolium bromide
4-Methyl-3-[[2-[[3-acetyl-4-(tetradecyloxy)benzoyl]amino]phenyl]methyl]thiazolium bromide
4-Methyl-3-[[2-[[3-acetyl-2-(tetradecyloxy)benzoyl]amino]phenyl]methyl]thiazolium bromide
4-Methyl-3-[[2-[[3-t-butyl-4-(tetradecyloxy)benzoyl]amino]phenyl]methyl]thiazolium bromide
4-Methyl-3-[[2-[[3-t-butyl-2-(tetradecyloxy)benzoyl]amino]phenyl]methyl]thiazolium bromide
4-Methyl-3-[[2-[[3-methoxy-4-(tetradecyloxy)benzoyl]amino]phenyl]methyl]thiazolium bromide
4-Methyl-3-[[2-[[3-methoxy-2-(tetradecyloxy)benzoyl]amino]phenyl]methyl]thiazolium bromide
4-Methyl-3-[[2-[[4-methoxy-2-(tetradecyloxy)benzoyl]amino]phenyl]methyl]thiazolium bromide
4-Methyl-3-[[3-[[-4-(tetradecyloxy)benzoyl]amino]-phenyl]methyl]thiazolium bromide
4-Methyl-3-[[3-[[-3-(tetradecyloxy)benzoyl]amino]-phenyl]methyl]thiazolium bromide
4-Methyl-3-[[3-[[-2-(tetradecyloxy)benzoyl]amino]-phenyl]methyl]thiazolium bromide
4-Methyl-3-[[3-[[3-chloro-4-(octyloxy)benzoyl]amino]-phenyl]methyl]thiazolium bromide
4-Methyl-3-[[3-[[3-chloro-2-(tetradecyloxy)benzoyl]amino]phenyl]methyl]thiazolium bromide
4-Methyl-3-[[3-[[3-fluoro-4-(tetradecyloxy)benzoyl]amino]phenyl]methyl]thiazolium bromide
4-Methyl-3-[[3-[[3-fluoro-2-(tetradecyloxy)benzoyl]amino]phenyl]methyl]thiazolium bromide 4-Methyl-3-[[3-[[3-acetyl-4-(tetradecyloxy)benzoyl-
  ]amino]phenyl]methyl]thiazolium bromide
4-Methyl-3-[[3-[[3-acetyl-2-(tetradecyloxy)benzoyl-
  ]amino]phenyl]methyl]thiazolium bromide
4-Methyl-3-[[3-[[3-t-butyl-4-(decyloxy)benzoyl]amino]-
  phenyl]methyl]thiazolium bromide
4-Methyl-3-[[3-[[3-t-butyl-2-(tetradecyloxy)benzoyl-
  ]amino]phenyl]methyl]thiazolium bromide
4-Methyl-3-[[3-[[3-methoxy-2-(tetradecyloxy)benzoyl-
  ]amino]phenyl]methyl]thiazolium bromide
4-Methyl-3-[[3-[[2-chloro-4-(tetradecyloxy)benzoyl-
  ]amino]phenyl]methyl]thiazolium bromide
4-Methyl-3-[[3-[[4-chloro-3-(tetradecyloxy)benzoyl-
  ]amino]phenyl]methyl]thiazolium bromide
4-Methyl-3-[[3-[[4-chloro-2-(tetradecyloxy)benzoyl-
  ]amino]phenyl]methyl]thiazolium bromide
4-Methyl-3-[[4-[[-2-(tetradecyloxy)benzoyl]amino]-
  phenyl]methyl]thiazolium bromide
4-Methyl-3-[[4-[[3-chloro-4-(tetradecyloxy)benzoyl-
  ]amino]phenyl]methyl]thiazolium bromide
4-Methyl-3-[[4-[[3-chloro-2-(tetradecyloxy)benzoyl-
  ]amino]phenyl]methyl]thiazolium bromide
4-Methyl-3-[[4-[[3-fluoro-4-(tetradecyloxy)benzoyl-
  ]amino]phenyl]methyl]thiazolium bromide
4-Methyl-3-[[4-[[3-acetyl-4-(tetradecyloxy)benzoyl-
  ]amino]phenyl]methyl]thiazolium bromide
4-Methyl-3-[[4-[[3-acetyl-2-(tetradecyloxy)benzoyl-
  ]amino]phenyl]methyl]thiazolium bromide
4-Methyl-3-[[4-[[3-t-butyl-4-(tetradecyloxy)benzoyl-
  ]amino]phenyl]methyl]thiazolium bromide
4-Methyl-3-[[4-[[3-t-butyl-2-(tetradecyloxy)benzoyl-
  ]amino]phenyl]methyl]thiazolium bromide
4-Methyl-3-[[4-[[3-methoxy-4-(tetradecyloxy)benzoyl-
  ]amino]phenyl]methyl]thiazolium bromide
4-Methyl-3-[[4-[[3-methoxy-2-(tetradecyloxy)benzoyl-
  ]amino]phenyl]methyl]thiazolium bromide
4-Methyl-3-[[4-[[2-chloro-4-(tetradecyloxy)benzoyl-
  ]amino]phenyl]methyl]thiazolium bromide
4-Methyl-3-[[4-[[4-chloro-3-(dodecyloxy)benzoyl-
  ]amino]phenyl]methyl]thiazolium bromide
4-Methyl-3-[[4-[[4-chloro-2-(tetradecyloxy)benzoyl-
  ]amino]phenyl]methyl]thiazolium bromide
4-Methyl-3-[[4-[[4-t-butyl-2-(tetradecyloxy)benzoyl-
  ]amino]phenyl]methyl]thiazolium bromide

EXAMPLE 29

3-[[[4-(Tetradecyloxy)phenyl]methyl]aminoben-
zenemethanol

To a solution of the N-[3-(hydroxymethyl)phenyl]-4-(tetradecyloxy)benzamide in 80 ml of tetrahydrofuran at 0° C. under argon is added 36.39 ml of 1M lithium aluminum hydride. Stirred at room temperature for 1 hour and refluxed for 7 hours. After stirring overnight and cooling to 0° C., ethyl acetate is added followed by sodium hydroxide solution until a solid forms. The mixture is diluted with ether, filtered and evaporated to a residue which is crystallized from hexane to give 6.7 g of the desired product as a white solid, m.p. 72°–75° C.

EXAMPLE 30

N-[3-(Hydroxmethyl)phenyl]-N-[[4-(tetradecyloxy)-
phenyl]methyl]acetamide

To a solution of 3-[[[4-(tetradecyloxy)phenyl]methyl-
]aminobenzenemethanol and 4.76 g of pyridine in 50 ml of methylene chloride, cooled to 0° C. over thirty minutes is added a solution of 4.13 g of acetyl chloride in 10 ml of methylene chloride. The mixture is stirred at ambient temperature for 1.5 hours, diluted with chloroform and washed with dilute hydrochloric acid then saturated sodium bicarbonate. The organic layer is dried and evaporated to a residue which is stirred with 60 ml of ethyl alcohol:1 ml of water and 0.84 g of sodium hydroxide for 35 minutes. The mixture is poured into water and extracted with ether. The organic layer is dried and evaporated to a residue which is crystallized from hexane to give 6.7 g of the desired product as a white solid, m.p. 65°–67° C.

EXAMPLE 31

N-[3-(Bromomethyl)phenyl]-N-[[4-(tetradecyloxy)-
phenyl]methyl]acetamide

To a solution of 6 g of N-[3-(hydroxymethyl)phenyl]-N-[[4-(tetradecyloxy)phenyl]methyl]acetamide in 100 ml of tetrahydrofuran is added 1.56 g of triethylamine and 1.76 g of methanesulfonyl chloride followed by stirring at ambient temperature for 1 hour. Added 11.14 g of lithium bromide and continued stirring for an additional hour. The mixture is poured into water and extracted with ether. The organic layer is washed with a solution of saturated sodium bicarbonate and brine then dried and evaporated to a residue which is crystallized from petroleum ether to give 6.6 g of the desired product as a white solid, m.p. 56°–58° C.

EXAMPLE 32

3-[[3-[Acetyl[[4-(tetradecyloxy)phenyl]methyl]amino]-
phenyl]methyl]-5-methylthiazolium bromide A mixture of 3 g of N-[3-(bromomethyl)phenyl]-N-[[4-(tetradecyloxy)phenyl]methyl]acetamide and 2.24 g of 5-methylthiazole in 40 ml of toluene is refluxed for 4 hours, cooled and diluted with 60 ml of ether and allowed to stand at room temperature overnight. The solid is collected by centrifugation and washed three times with ether then vacuum dried to give 3.1 g of the desired product as a white powder, m.p. 130°–134° C.

EXAMPLE 33 p-(Tetradecyloxy)phenyl isocyanate

To a solution of 8.74 g of triphosgene in 125 ml of methylene chloride cooled to 0° C. is added dropwise a solution of p-(tetradecyloxy)aniline, 7.95 g of triethylamine and 239.93 mg of dimethylaminopyrydine in 125 ml of methylene chloride over 30 minutes. Stirring at ambient temperature is continued for 4 hours. The solvent is evaporated and the residue stirred with ether and filtered. The cake is washed with additional ether and the combined flitrates evaporated to give the desired product as an oil.

EXAMPLE 34

N-[3-(Hydroxymethyl)phenyl]-N'-[4-(tetradecyloxy)-
phenyl]urea

To a 0° C. solution of 13 g of p-(tetradecyloxy)phenyl isocyanate in 70 ml of tetrahydrofuran and 30 ml of pyridine is added over 10 minutes a solution of 7.24 g of 3-aminobenzyl alcohol in 70 ml of tetrahydrofuran with continued stirring for one hour. The mixture is heated until all the solids dissolve then allowed to stand at ambient temperature overnight. The mixture is poured into water and the solid collected. The solid is washed with dilute hydrochloric acid and water then crystallized from ethyl alcohol to give 13.1 g of the desired product as a light pink solid, m.p. 150°–158° C.

EXAMPLE 35

N-[3-(Bromoethyl)phenyl]-N'-[4-(tetradecyloxy)phenyl]urea

A mixture of 10.0 g of N-[3-(hydroxymethyl)phenyl]-N'-[4-(tetradecyloxy)phenyl]urea, 70 ml of hydrogen bromide in acetic acid and 40 ml of chloroform is refluxed for 2.5 hours, then cooled. The solid is collected and washed with carbon tetrachloride and two times with water. The collected solid is crystallized from ethyl alcohol:tetrahydrofuran followed by recrystallization from tetrahydrofuran to give 7.4 g of the desired product as a white powder, m.p. 164°–169° C.

EXAMPLE 36

5-Methyl-3-[[3-[[[[4-(tetradecyloxy)phenyl]amino]carbonyl]amino]phenyl]methyl]thiazolium bromide A mixture of 4 g of N-[3-(bromomethyl)phenyl]-N'-[4-(tetradecyloxy)phenyl]urea and 2.3 g of 5-methylthiazole in 60 ml of tetrahydrofuran is refluxed for 4 hours. The solvent is evaporated, toluene added to the residue and evaporated to a residue. The residue is stirred with ether and the solid collected, washed with fresh ether and dried under vacuum to give 4.7 g of the desired product as a white powder, m.p. 65°–168° C.

According to the methods outlined hereinabove in Flowsheet I and described in detail in Examples 33–36, the compounds of this invention listed hereinbelow in List 3 can be prepared. These methods are applicable to the preparation of the compounds of this invention by one skilled in the art.

List 3

3-[[2-[[[[-4-(tetradecyloxy)phenyl]amino]carbonyl]amino]phenyl]methyl]thiazolium bromide
3-[[2-[[[[3-methoxy-4-(tetradecyloxy)phenyl]amino]carbonyl]amino]phenyl]methyl]thiazolium bromide
3-[[2-[[[[3-methoxy-2-(tetradecyloxy)phenyl]amino]carbonyl]amino]phenyl]methyl]thiazolium bromide
3-[[2-[[[[2-chloro-4-(tetradecyloxy)phenyl]amino]carbonyl]amino]phenyl]methyl]thiazolium bromide
3-[[2-[[[[4-chloro-3-(tetradecyloxy)phenyl]amino]carbonyl]amino]phenyl]thiazolium bromide
3-[[2-[[[[4-t-butyl-2-(tetradecyloxy)phenyl]amino]carbonyl]amino]phenyl]methyl]thiazolium bromide
3-[[2-[[[[4-methoxy-3-(tetradecyloxy)phenyl]amino]carbonyl]amino]phenyl]methyl]thiazolium bromide
3-[[2-[[[[4-methoxy-2-(tetradecyloxy)phenyl]amino]carbonyl]amino]phenyl]methyl]thiazolium bromide
3-[[3-[[[[-4-(tetradecyloxy)phenyl]amino]carbonyl]amino]phenyl]methyl]thiazolium bromide
3-[[3-[[[[-3-(tetradecyloxy)phenyl]amino]carbonyl]amino]phenyl]methyl]thiazolium bromide
3-[[3-[[[[3-chloro-2-(tetradecyloxy)phenyl]amino]carbonyl]amino]phenyl]methyl]thiazolium bromide
3-[[3-[[[[3-fluoro-4-(tetradecyloxy)phenyl]amino]carbonyl]amino]phenyl]methyl]thiazolium bromide
3-[[3-[[[[3-fluoro-2-(tetradecyloxy)phenyl]amino]carbonyl]amino]phenyl]methyl]thiazolium bromide
3-[[3-[[[[3-methoxy-4-(tetradecyloxy)phenyl]amino]carbonyl]amino]phenyl]methyl]thiazolium bromide
3-[[3-[[[[3-methoxy-2-(tetradecyloxy)phenyl]amino]carbonyl]amino]phenyl]methyl]thiazolium bromide
3-[[3-[[[[2-chloro-4-(tetradecyloxy)phenyl]amino]carbonyl]amino]phenyl]methyl]thiazolium bromide
3-[[4-[[[[-3-(hexadecyloxy)phenyl]amino]carbonyl]amino]phenyl]methyl]thiazolium bromide
3-[[4-[[[[-2-(tetradecyloxy)phenyl]amino]carbonyl]amino]phenyl]methyl]thiazolium bromide
3-[[4-[[[[-2-(hexadecyloxy)phenyl]amino]carbonyl]amino]phenyl]methyl]thiazolium bromide
3-[[4-[[[[3-chloro-4-(tetradecyloxy)phenyl]amino]carbonyl]amino]phenyl]methyl]thiazolium bromide
3-[[4-[[[[3-chloro-4-(hexadecyloxy)phenyl]amino]carbonyl]amino]phenyl]methyl]thiazolium bromide
3-[[4-[[[[3-chloro-2-(tetradecyloxy)phenyl]amino]carbonyl]amino]phenyl]methyl]thiazolium bromide
3-[[4-[[[[3-acetyl-2-(tetradecyloxy)phenyl]amino]carbonyl]amino]phenyl]methyl]thiazolium bromide
3-[[4-[[[[3-acetyl-2-(hexadecyloxy)phenyl]amino]carbonyl]amino]phenyl]methyl]thiazolium bromide
3-[[4-[[[[3-t-butyl-4-(tetradecyloxy)phenyl]amino]carbonyl]amino]phenyl]methyl]thiazolium bromide
3-[[4-[[[[3-t-butyl-4-(hexadecyloxy)phenyl]amino]carbonyl]amino]phenyl]methyl]thiazolium bromide
3-[[4-[[[[3-t-butyl-2-(tetradecyloxy)phenyl]amino]carbonyl]amino]phenyl]methyl]thiazolium bromide
3-[[4-[[[[3-methoxy-4-(hexadecyloxy)phenyl]amino]carbonyl]amino]phenyl]methyl]thiazolium bromide
3-[[4-[[[[3-methoxy-2-(tetradecyloxy)phenyl]amino]carbonyl]amino]phenyl]methyl]thiazolium bromide
3-[[4-[[[[3-methoxy-2-(hexadecyloxy)phenyl]amino]carbonyl]amino]phenyl]methyl]thiazolium bromide
3-[[4-[[[[2-chloro-4-(tetradecyloxy)phenyl]amino]carbonyl]amino]phenyl]methyl]thiazolium bromide
5-Methyl-3-[[2-[[[[-4-(tetradecyloxy)phenyl]amino]carbonyl]amino]phenyl]methyl]thiazolium bromide
5-Methyl-3-[[2-[[[[-3-(tetradecyloxy)phenyl]amino]carbonyl]amino]phenyl]methyl]thiazolium bromide
5-Methyl-3-[[2-[[[[-2-(tetradecyloxy)phenyl]amino]carbonyl]amino]phenyl]methyl]thiazolium bromide
5-Methyl-3-[[2-[[[[3-chloro-4-(tetradecyloxy)phenyl]amino]carbonyl]amino]phenyl]methyl]thiazolium bromide
5-Methyl-3-[[2-[[[[3-chloro-2-(tetradecyloxy)phenyl]amino]carbonyl]amino]phenyl]methyl]thiazolium bromide
5-Methyl-3-[[2-[[[[3-fluoro-4-(tetradecyloxy)phenyl]amino]carbonyl]amino]phenyl]methyl]thiazolium bromide
5-Methyl-3-[[2-[[[[3-fluoro-2-(tetradecyloxy)phenyl]amino]carbonyl]amino]phenyl]methyl]thiazolium bromide
5-Methyl-3-[[2-[[[[3-acetyl-2-(tetradecyloxy)phenyl]amino]carbonyl]amino]phenyl]methyl]thiazolium bromide
5-Methyl-3-[[2-[[[[3-t-butyl-4-(tetradecyloxy)phenyl]amino]carbonyl]amino]phenyl]methyl]thiazolium bromide
5-Methyl-3-[[2-[[[[3-t-butyl-2-(tetradecyloxy)phenyl]amino]carbonyl]amino]phenyl]methyl]thiazolium bromide
5-Methyl-3-[[2-[[[[3-methoxy-4-(tetradecyloxy)phenyl]amino]carbonyl]amino]Phenyl]methyl]thiazolium bromide
5-Methyl-3-[[2-[[[[3-methoxy-2-(tetradecyloxy)phenyl]amino]carbonyl) amino]Phenyl]methyl]thiazolium bromide
5-Methyl-3-[[2-[[[[2-chloro-4-(tetradecyloxy)phenyl]amino]carbonyl]amino]Phenyl]methyl]thiazolium bromide
5-Methyl-3-[[2-[[[[4-chloro-3-(tetradecyloxy)phenyl]amino]carbonyl]amino]Phenyl]methyl]thiazolium bromide 5-Methyl-3-[[2-[[[[4-t-butyl-2-(tetradecyloxy)phenyl]amino]carbonyl]amino]Phenyl]methyl]thiazolium bromide
5-Methyl-3-[[3-[[[[3-chloro-2-(tetradecyloxy)phenyl]amino]carbonyl]amino]Phenyl]methyl]thiazolium bromide
5-Methyl-3-[[3-[[[[3-chloro-2-(dodecyloxy)phenyl]amino]carbonyl]amino]Phenyl]methyl]thiazolium bromide
5-Methyl-3-[[3-[[[[3-fluoro-4-(tetradecyloxy)phenyl]amino]carbonyl]amino]Phenyl]methyl]thiazolium bromide
5-Methyl-3-[[3-[[[[3-fluoro-4-(dodecyloxy)phenyl]amino]carbonyl]amino]Phenyl]methyl]thiazolium bromide
5-Methyl-3-[[3-[[[[3-fluoro-2-(tetradecyloxy)phenyl)amino]carbonyl]amino]Phenyl]methyl]thiazolium bromide
5-Methyl-3-[[3-[[[[3-fluoro-2-(dodecyloxy)phenyl]amino]carbonyl]amino]phenyl]methyl]thiazolium bromide
5-Methyl-3-[[3-[[[[3-acetyl-4-(tetradecyloxy)phenyl]amino]carbonyl]amino]Phenyl]methyl]thiazolium bromide
5-Methyl-3-[[3-[[[[3-acetyl-4-(dodecyloxy)phenyl)amino]carbonyl]amino]phenyl]methyl]thiazolium bromide
5-Methyl -3-[[3-[[[[3-acetyl-2-(tetradecyloxy)phenyl]amino]carbonyl)amino)phenyl]methyl]thiazolium bromide
5-Methyl-3-[[3-[[[[3-t-butyl-4-(dodecyloxy)phenyl]amino]carbonyl]amino]Phenyl]methyl]thiazolium bromide
5-Methyl-3-[[3-[[[[2-chloro-4-(tetradecyloxy)phenyl)amino]carbonyl]amino]phenyl]methyl)thiazolium bromide
5-Methyl-3-[[3-[[[[4-chloro-3-(dodecyloxy)phenyl]amino]carbonyl]amino]phenyl)methyl)thiazolium bromide
5-Methyl-3-[[3-[[[[4-chloro-2-(tetradecyloxy)phenyl]amino]carbonyl]amino]Phenyl]methyl]thiazolium bromide
5-Methyl-3-[[3-[[[[4-chloro-2-(dodecyloxy)phenyl]amino]carbonyl]amino]Phenyl]methyl]thiazolium bromide
5-Methyl-3-[[3-[[[[4-t-butyl-3-(decyloxy)phenyl]amino]carbonyl]amino]Phenyl]methyl]thiazolium bromide
5-Methyl-3-[[3-[[[[4-methoxy-3-(hexadecyloxy)phenyl]amino]carbonyl]amino]phenyl]methyl]thiazolium bromide
5-Methyl -3-[[3-[[[[4-methoxy-2-(tetradecyloxy)phenyl]amino]carbonyl]amino]phenyl]methyl]thiazolium bromide
5-Methyl-3-[[3-[[[[4-methoxy-2-(dodecyloxy)phenyl]amino]carbonyl]amino]phenyl]methyl]thiazolium bromide
5-Methyl-3-[[4-[[[[-4-(tetradecyloxy)phenyl]amino]carbonyl]amino]phenyl]methyl]thiazolium bromide
5-Methyl-3-[[4-[[[[-3-(tetradecyloxy)phenyl]amino]carbonyl]amino]phenyl]methyl]thiazolium bromide
5-Methyl-3-[[4-[[[[-2-(tetradecyloxy)phenyl]amino]carbonyl]amino]phenyl]methyl]thiazolium bromide
5-Methyl-3-[[4-[[[[3-acetyl-4-(tetradecyloxy)phenyl]amino]carbonyl]amino]phenyl]methyl]thiazolium bromide
5-Methyl-3-[[4-[[[[3-acetyl-2-(tetradecyloxy)phenyl]amino]carbonyl]amino]phenyl]methyl]thiazolium bromide
5-Methyl-3-[[4-[[[[3-t-butyl-4-(decyloxy)phenyl]amino]carbonyl]amino]phenyl]methyl]thiazolium bromide
5-Methyl-3-[[4-[[[[3-t-butyl-2-(tetradecyloxy)phenyl]amino]carbonyl]amino]phenyl]methyl]thiazolium bromide
5-Methyl-3-[[4-[[[[3-methoxy-4-(tetradecyloxy)phenyl]amino]carbonyl]amino]phenyl]methyl]thiazolium bromide
5-Methyl-3-[[4-[[[[3-methoxy-2-(tetradecyloxy)phenyl]amino]carbonyl]amino]phenyl]methyl]thiazolium bromide
5-Methyl-3-[[4-[[[[2-chloro-4-(tetradecyloxy)phenyl]amino]carbonyl]amino]phenyl]methyl]thiazolium bromide
5-Methyl-3-[[4-[[[[4-chloro-3-(tetradecyloxy)phenyl]amino]carbonyl]amino]phenyl]methyl]thiazolium bromide
5-Methyl-3-[[4-[[[[4-chloro-2-(tetradecyloxy)phenyl]amino]carbonyl]amino]phenyl]methyl]thiazolium bromide
5-Methyl-3-[[4-[[[[4-t-butyl-3-(tetradecyloxy)phenyl]amino]carbonyl]amino]phenyl]methyl]thiazolium bromide
5-Methyl-3-[[4-[[[[4-t-butyl-2-(tetradecyloxy)phenyl]amino]carbonyl]amino]phenyl]methyl]thiazolium bromide
5-Methyl-3-[[4-[[[[4-methoxy-3-(tetradecyloxy)phenyl]amino]carbonyl]amino]phenyl]methyl]thiazolium bromide
5-Methyl-3-[[4-[[[[4-methoxy-2-(tetradecyloxy)phenyl]amino]carbonyl]amino]phenyl]methyl]thiazolium bromide
2-Methyl-3-[[2-[[[[-4-(tetradecyloxy)phenyl]amino]carbonyl]amino]phenyl]methyl]thiazolium bromide
2-Methyl-3-[[2-[[[[2-chloro-4-(tetradecyloxy)phenyl]amino]carbonyl]amino]phenyl]methyl]thiazolium bromide
2-Methyl -3-[[2-[[[[4-chloro-3-(tetradecyloxy)phenyl]amino]carbonyl]amino]phenyl]methyl]thiazolium bromide
2-Methyl-3-[[2-[[[[4-chloro-2-(tetradecyloxy)phenyl]amino]carbonyl]amino]phenyl]methyl]thiazolium bromide
2-Methyl-3-[[2-[[[[4-t-butyl-3-(tetradecyloxy)phenyl]amino]carbonyl]amino]phenyl]methyl]thiazolium bromide
2-Methyl-3-[[2-[[[[4-methoxy-2-(tetradecyloxy)phenyl]amino]carbonyl]amino]phenyl]methyl]thiazolium bromide
2-Methyl-3-[[3-[[[[-4-(tetradecyloxy)phenyl]amino]carbonyl]amino]phenyl]methyl]thiazolium bromide
2-Methyl-3-[[3-[[[[-3-(tetradecyloxy)phenyl]amino]carbonyl]amino]phenyl]methyl]thiazolium bromide
2-Methyl-3-[[3-[[[[-2-(tetradecyloxy)phenyl]amino]carbonyl]amino]phenyl]methyl]thiazolium bromide
2-Methyl-3-[[3-[[[[3-chloro-4-(tetradecyloxy)phenyl]amino]carbonyl]amino]phenyl]methyl]thiazolium bromide
2-Methyl-3-[[3-[[[[3-chloro-2-(tetradecyloxy)phenyl]amino]carbonyl]amino]phenyl]methyl]thiazolium bromide
2-Methyl-3-[[3-[[[[3-fluoro-4-(tetradecyloxy)phenyl]amino]carbonyl]amino]phenyl]methyl]thiazolium bromide
2-Methyl-3-[[3-[[[[3-fluoro-2-(tetradecyloxy)phenyl]amino]carbonyl]amino]phenyl]methyl]thiazolium bromide 2-Methyl-3-[[3-[[[[2-chloro-4-(tetradecyloxy)phenyl-]amino]carbonyl]amino]phenyl]methyl]thiazolium bromide 2-Methyl-3-[[3-[[[[4-t-butyl-3-(tetradecyloxy)phenyl-]amino]carbonyl]amino]phenyl]methyl]thiazolium bromide 2-Methyl-3-[[4-[[[[3-fluoro-2-(tetradecyloxy)phenyl-]amino]carbonyl]amino]phenyl]methyl]thiazolium bromide 2-Methyl-3-[[4-[[[[3-acetyl-4-(tetradecyloxy)phenyl-]amino]carbonyl]amino]phenyl]methyl]thiazolium bromide 2-Methyl-3-[[4-[[[[3-acetyl-2-(tetradecyloxy)phenyl-]amino]carbonyl]amino]phenyl]methyl]thiazolium bromide 2-Methyl-3-[[4-[[[[3-methoxy-4-(tetradecyloxy)phenyl-]amino]carbonyl]amino]phenyl]methyl]thiazolium bromide 2-Methyl-3-[[4-[[[[4-methoxy-3-(tetradecyloxy)phenyl-]amino]carbonyl]amino]phenyl]methyl]thiazolium bromide 2-Methyl-3-[[4-[[[[4-methoxy-2-(tetradecyloxy)phenyl-]amino]carbonyl]amino]phenyl]methyl]thiazolium bromide 4-Methyl-3-[[2-[[[[-4-(tetradecyloxy)phenyl]amino]carbonyl]amino]phenyl]methyl]thiazolium bromide 4-Methyl-3-[[2-[[[[-3-(tetradecyloxy)phenyl)amino)carbonyl]amino]Phenyl]methyl]thiazolium bromide 4-Methyl-3-[[2-[[[[-2-(tetradecyloxy)phenyl]amino]carbonyl]amino]Phenyl]methyl]thiazolium bromide 4-Methyl-3-[[2-[[[[3-chloro-4-(tetradecyloxy)phenyl-]amino)carbonyl]amino]phenyl]methyl]thiazolium bromide 4-Methyl-3-[[2-[[[[3-chloro-2-(tetradecyloxy)phenyl-]amino]carbonyl]amino]Phenyl]methyl]thiazolium bromide 4-Methyl-3-[[2-[[[[3-fluoro-4-(tetradecyloxy)phenyl-]amino]carbonyl]amino]Phenyl]methyl]thiazolium bromide 4-Methyl-3-[[2-[[[[3-fluoro-2-(tetradecyloxy)phenyl-]amino]carbonyl]amino]Phenyl]methyl]thiazolium bromide 4-Methyl-3-[[2-[[[[3-acetyl-4-(tetradecyloxy)phenyl-]amino]carbonyl]amino]Phenyl]methyl]thiazolium bromide 4-Methyl-3-[[2-[[[[3-acetyl-2-(tetradecyloxy)phenyl-]amino]carbonyl]amino]Phenyl]methyl]thiazolium bromide 4-Methyl-3-[[2-[[[[3-t-butyl-4-(tetradecyloxy)phenyl-)amino]carbonyl]amino]Phenyl]methyl]thiazolium bromide 4-Methyl-3-[[3-[[[[-2-(tetradecyloxy)phenyl]amino]carbonyl]amino]phenyl]methyl]thiazolium bromide 4-Methyl-3-[[3-([[[3-chloro-4-(octyloxy)phenyl]amino]-carbonyl]amino]Phenyl]methyl]thiazolium bromide 4-Methyl-3-[[3-[[[[3-chloro-2-(tetradecyloxy)phenyl-]amino]carbonyl]amino]Phenyl]methyl]thiazolium bromide 4-Methyl-3-[[3-[[[[3-fluoro-4-(tetradecyloxy)phenyl-]amino)carbonyl)amino]phenyl]methyl]thiazolium bromide 4-Methyl-3-[[3-[[[[3-fluoro-2-(tetradecyloxy)phenyl-]amino]carbonyl]amino]phenyl]methyl]thiazolium bromide 4-Methyl-3-[[3-[[[[3-acetyl-4-(tetradecyloxy)phenyl-]amino]carbonyl]amino]phenyl]methyl]thiazolium bromide 4-Methyl-3-[[3-([([3-acetyl-2-(tetradecyloxy)phenyl-]amino]carbonyl]amino]phenyl]methyl]thiazolium bromide 4-Methyl-3-[[3-[[[[3-t-butyl-4-(decyloxy)phenyl]amino]-carbonyl]amino]phenyl]methyl]thiazolium bromide 4-Methyl-3-[[3-[[[[3-t-butyl-2-(tetradecyloxy)phenyl-]amino]carbonyl]amino]phenyl]methyl]thiazolium bromide 4-Methyl-3-[[3-[[[[3-methoxy-2-(tetradecyloxy)phenyl-]amino]carbonyl]amino]phenyl]methyl]thiazolium bromide 4-Methyl-3-[[3-[[[[2-chloro-4-(tetradecyloxy)phenyl-]amino]carbonyl]amino]phenyl]methyl]thiazolium bromide 4-Methyl-3-[[3-[[[[4-chloro-3-(tetradecyloxy)phenyl-]amino]carbonyl]amino]Phenyl]methyl]thiazolium bromide 4-Methyl-3-[[3-[[[[4-chloro-2-(tetradecyloxy)phenyl-]amino]carbonyl]amino]phenyl]methyl]thiazolium bromide 4-Methyl-3-[[4-[[[[-2-(tetradecyloxy)phenyl]amino]carbonyl]amino]phenyl]methyl]thiazolium bromide 4-Methyl-3-[[4-[[[[3-chloro-4-(tetradecyloxy)phenyl-)amino]carbonyl]amino]phenyl]methyl)thiazolium bromide 4-Methyl-3-[[4-[[[[3-chloro-2-(tetradecyloxy)phenyl-]amino]carbonyl]amino]phenyl]methyl]thiazolium bromide 4-Methyl-3-[[4-[[[[3-methoxy-2-(tetradecyloxy)phenyl-]amino]carbonyl]amino)phenyl]methyl]thiazolium bromide 4-Methyl -3-[[4-[[[[2-chloro-4-(tetradecyloxy)phenyl-]amino]carbonyl]amino]Phenyl]methyl)thiazolium bromide 4-Methyl-3-[[4-[[[[4-chloro-3-(dodecyloxy)phenyl-]amino]carbonyl]amino]phenyl]methyl]thiazolium bromide 4-Methyl-3-[[4-[[[[4-chloro-2-(tetradecyloxy)phenyl-]amino]carbonyl]amino]phenyl]methyl]thiazolium bromide 4-Methyl-3-[[4-[[[[4-t-butyl-2-(tetradecyloxy)phenyl-]amino]carbonyl]amino]phenyl]methyl]thiazolium bromide

EXAMPLE 37

4-Methyl-1-(3-nitrophenyl)-1H-imidazole

To a mixture of 112.9 g of m-fluoronitrobenzene and 65.69 g of 4-methylimidazole in 1 liter of dimethylsulfoxide is added 58.51 g of potassium carbonate followed by heating under dry conditions at 110° C. for 39 hours. The reaction mixture is poured into 3.2 liters of water and stored in a refrigerator for 2 days. The mixture is filtered and the cake washed with copious volumes of water followed by suction drying to give 25 g of brown solid. The solid is crystallized from ethyl acetate to give 15.0 g of the desired product as a beige solid, m.p. 119°–120° C. From the combined recrystallization filtrates is obtained 800 mg of 5-methyl-1-(3-nitrophenyl)-1H-imidazole as a beige solid, m.p. 130°–132° C.

EXAMPLE 38

3-(4-Methyl-1H-imidazol-1-yl)benzenamine

A mixture of 14.6 g of 4-methyl-1-(3-nitrophenyl)-1H-imidazole, 766 mg of palladium black, 19.6 g of sodium formate, 12.8 ml of formic acid in 300 ml of methyl alcohol is stirred for 18 hours under a hydrogen atmosphere. The mixture is filtered through diatomaceous earth and the filtrate evaporated to a residue. The residue is partitioned between saturated potassium bicarbonate and chloroform. The organic layer is dried and evaporated to a residue which is dissolved in a minimum of chloroform and passed through a pad of hydrous magnesium silicate. The filtrate is evaporated to a residue which is stirred with ether and the resulting solid filtered and air dried to give 10.3 g of the desired product as a solid, m.p. 117°–119° C.

EXAMPLE 39

N-[3-(2-Methyl-1H-imidazol-1-yl)phenyl-4-(tetradecyloxy)benzeneacetamide

To a solution of 2.8 g of p-tetradecyloxybenzoyl chloride in 30 ml of tetrahydrofuran is added a solution of 1.32 g of 3-(4-methyl-1H-imidazol-1-yl) benzenamine and 2.41 g of pyridine in 30 ml of tetrahydrofuran followed by stirring for 2 hours at ambient temperature. The mixture is heated briefly to reflux then stirred at ambient temperature for 2 hours. The solvent is evaporated to a residue. The residue is partitioned between chloroform and saturated sodium bicarbonate. The organic layer is dried and evaporated to an oil which is chromatographed on silica gel using ethyl acetate:5% methyl alcohol:0.1% ammonium hydroxide to give a solid which is crystallized from hexane:carbon tetrachloride to give 2.6 g of the desired compound as a white solid, m.p. 110°–112° C.

EXAMPLE 40

N-[3-(2-Methyl-1H-imidazol-1-yl)phenyl-4-(tetradecyloxy)benzeneacetamide monohydrochloride To a solution of 500 mg of N-[3-(2-methyl-1H-imidazol-1-yl)phenyl-4-(tetradecyloxy)benzeneacetamide in a minimum of ether is treated with 70 ml of ether saturated with hydrogen chloride. The resulting solid is collected via centrifugation, washed with ether and vacuum dried to give 0.4 g of the desired product as a white solid, m.p. 175°–178° C.

EXAMPLE 41

2,3-Dimethyl-1-[3-[[[4-(tetradecyloxy)phenyl]acetyl]amino]phenyl]-1H-imidazolium iodide A mixture of 800 mg of N-[3-(2-methyl-1H-imidazol-1-yl)phenyl-4-(tetradecyloxy)benzeneacetamide and 1.13 g of methyl iodide in 15 ml of toluene is refluxed for 2.5 hours. The solvent is evaporated to a residue which is stirred with ether and the solid collected by centrifugation, washed with ether and vacuum dried to give 0.8 g of the desired product as a solid, m.p. 140°–143° C.

EXAMPLE 42

2-Methyl-1-(p-nitrophenyl)imidazole

A mixture of 50.0 g of p-fluoronitrobenzene, 85.93 g of 2-methylimidazole and 44.9 g of potassium carbonate in 860 ml of dimethylsulfoxide is heated at 120° C. for 24 hours. The mixture is poured into 2.5 liter of water and stored in a refrigerator for two days. The mixture is filtered and cake washed with copious volumes of water and vacuum dried. The cake is dissolved in 1500 ml of ethyl acetate, filtered through hydrous magnesium silicate and the filtrate reduced to about 500 ml, cooled and the resulting solid, filtered, and air dried to give 81.0 g of the desired product as brown crystals, m.p. 135°–137° C.

EXAMPLE 43

4-(2-Methyl-1H-imidazol-1-yl)benzenamine

A mixture of 54.0 g of 2-methyl-1-(p-nitrophenyl)imidazole, 2.87 g of palladium black, 36.7 g of sodium formate and 47.4 ml of formic acid in 1100 ml of methyl alcohol is stirred at room temperature for 18 hours under a hydrogen atmosphere. The mixture is filtered and the filtrate evaporated to a residue. The residue is partitioned between saturated potassium bicarbonate and chloroform. The organic layer is dried and passed through a pad of hydrous magnesium silicate. The filtrate is evaporated to a residue which is crystallized from ether:ethanol to give 34.9 g of the desired product as a solid, m.p. 108°–110° C.

EXAMPLE 44

N-[4-(2-Methyl-1H-imidazol-1-yl)phenyl]-4-(tetradecyloxy)benzeneacetamide

To a solution of 5.0 g of p-tetradecyloxyphenylacetyl chloride in 50 ml of tetrahydrofuran is added to a solution of 4.31 g of pyridine and 2.36 g of 4-(2-methyl-1H-imidazol-1-yl)benzenamine in 50 ml of tetrahydrofuran over 5 minutes. The mixture is stirred at ambient temperature for 1 hour, heated to reflux and allowed to stir at room temperature for 2 hours. The solvent is evaporated to a residue which is partitioned between chloroform and dilute sodium bicarbonate. The organic layer is separated, washed with water, dried and filtered through a pad of magnesium silicate. The solvent is evaporated to an oil which crystallizes from methyl alcohol:water to give 4.0 g of white solid which is chromatographed on silica gel using ethyl acetate containing 0.1% ammonium hydroxide to give 3.9 g of the desired product as a white solid, m.p. 106°–109° C.

EXAMPLE 45

N-[4-(2-Methyl-1H-imidazol-1-yl)phenyl]-4-(tetradecyloxy)benzeneacetamide monohydrochloride A solution of 500 mg of N-[4-(2-methyl-1H-imidazol-1-yl)phenyl]-4-(tetradecyloxy)benzeneacetamide in 7 ml of tetrahydrofuran and 70 ml of ether is saturated with hydrogen chloride. The solid is collected by centrifugation, washed three times with ether and vacuum dried to give 0.5 g of the desired product as a white solid, m.p. 207°–211° C.

EXAMPLE 46

2,3-Dimethyl-1-[4-[[[4-(tetradecyloxy)phenyl]acetyl]amino]phenyl]-1H-imidazolium iodide A mixture of 1.5 g of N-[4-(2-methyl-1H-imidazol-1-yl)phenyl]-4-(tetradecyloxy)benzeneacetamide and 2.11 g of methyl iodide in 25 ml of toluene is refluxed under argon for 2 hours, cooled, diluted with ether and the solid collected. The cake is dried to give 1.8 g of the desired product as a white solid, m.p. 140°–143° C.

EXAMPLE 47 p-(Hexadecyloxy)phenol

To a suspension of 28.99 g of 60% sodium hydride in 350 ml of N,N-dimethylformamide, cooled to 0° C. and under argon is added 60 g of hydroquinone in 450 ml of N,N-dimethylformamide with stirring over 40 minutes. After an additional 30 minutes, 450 ml of tetrahydrofuran is added followed by 192 g of 1-iodohexadecane over one hour. The mixture is stirred at room temperature for 3 hours. The reaction mixture poured into dilute hydrochloric acid and extracted with chloroform. The organic layer is washed with water, dried and evaporated to give the desired product as an oil.

EXAMPLE 48

4-Hexadecyloxyphenoxyacetic acid methyl ester

A mixture of 23 g of p-(hexadecyloxy)phenol, 13.35 g of methyl bromoacetate, 10.45 g of potassium carbonate in 200 ml of acetone is refluxed for 24 hours. The mixture is cooled, chloroform added and filtered. The filtrate is evaporated and the residue crystallized from hexane to give 25 g of the desired compound as a gray white solid.

EXAMPLE 49

[4-(Hexadecyloxy)phenoxy]acetic acid

A mixture of 24.5 g of 4-Hexadecyloxyphenoxyacetic acid methyl ester 10.14 g of potassium hydroxide in 10 ml of water and 250 ml ethyl alcohol is refluxed for 3 hours then allowed to stand at 50° for 18 hours. The mixture is poured into dilute hydrochloric acid and extracted with chloroform. The organic layer is evaporated to a residue which is crystallized from hexane:carbon tetrachloride to give 13.7 g of the desired product as a white solid, m.p. 125°-127° C.

EXAMPLE 50

4-Hexadecyloxyphenoxyacetyl chloride

A mixture of 13.2 g of [4-(hexadecyloxy)phenoxy]acetic acid, 6.4 g of oxalyl chloride, 225 ml of methylene chloride and 5 drops of N,N-dimethylformamide is stirred at ambient temperature for 17 hours. The solvent is evaporated to a residue which is dissolved in ether and filtered through diatomaceous earth. The filtrate is evaporated to give 13.9 g of the desired product as a white solid.

EXAMPLE 51

2-[4-(Hexadecyloxy)phenoxy]-N-[3-hydroxymethyl)-phenyl]acetamide

To a solution of 1.75 g of m-aminobenzyl alcohol and 3.46 g of pyridine in 60 ml of methylene chloride cooled to 0° C., is added dropwise with stirring 4.5 g of 4-hexadecyloxyphenoxyacetyl chloride in 60 ml of methylene chloride over 30 minutes. Stirring is continued for 4 hours. The mixture is diluted with chloroform and poured into water. The organic layer is washed with dilute hydrochloric acid, dried and evaporated to a residue which is crystallized from carbon tetrachloride to give 5.1 g of the desired product as a white solid, m.p. 88°-91° C.

EXAMPLE 52

N-[3-(Bromomethyl)phenyl]-2-[4-(hexadecyloxy)-phenoxy]acetamide

To a solution of 3.5 g of 2-[4-(hexadecyloxy)phenoxy]-N-[3-hydroxymethyl)phenyl]acetamide and 1.29 g of methanesulfonyl chloride in 60 ml of tetrahydrofuran is added 853.89 mg of triethylamine followed by stirring at room temperature for 2.5 hours. Stirring is continued for 4 hours after adding 6.11 g of lithium bromide. The mixture is poured into water and extracted with ether. The organic layer is washed with saturated sodium bicarbonate, dried and evaporated to a residue which is crystallized from hexane to give a solid which is chromatographed on silica gel with chloroform to give a solid which is crystallized from hexane to give 2.1 g of the desired product as a white solid, m.p. 183°-186° C.

EXAMPLE 53

3-[[3-[[[4-Hexadecyloxy)phenoxy]acetyl]amino]-phenyl]methyl]-5-methyl-thiazolium bromide A mixture of 1.9 g of N-[3-(bromomethyl)phenyl]-2-[4-(hexadecyloxy)phenoxy]acetamide and 1.68 g of 5-methyl thiazole in 25 ml of toluene is refluxed under argon for 5.5 hours then concentrated to a residue which is mixed with ether and the solid collected by centrifugation then washed several times with ether. The solid is vacuum dried to give 1.7 g of the desired product as a white solid, m.p. 121°-124° C.

EXAMPLE 54

2-[4-(Hexadecyloxy)phenoxy]-N-[2-(hydroxymethyl)-phenyl]acetamide

To a solution of 1.36 g of O-aminobenzyl alcohol and 2.69 g of pyridine in 60 ml of methylene chloride is added dropwise with stirring over 40 minutes a solution of 3.5 g of 4-hexadecyloxyphenoxyacetyl chloride in 40 ml of methylene chloride. Stirring is continued at room temperature for 4 hours. The mixture is diluted with chloroform and heated to dissolve the solids, washed with water and dilute hydrochloric acid. The organic layer is dried and evaporated to a residue which is crystallized from carbon tetrachloride to give 3.9 g of the desired product as a white solid, m.p. 128°-131° C.

EXAMPLE 55

N-[2-(Bromomethyl)phenyl]-2-[4-(hexadecyloxy)-phenoxy]acetamide

To a solution of 3.5 g of 2-[4-(hexadecyloxy)phenoxy]-N-[2-(hydroxymethyl)phenyl]acetamide and 1.29 g of methanesulfonyl chloride in 60 ml of tetrahydrofuran is added 853.89 mg of triethylamine followed by stirring at room temperature for 2.5 hours. Also added is 6.11 g of lithium bromide followed by stirring at room temperature for 4 hours. The mixture is poured into water and extracted with ether. The organic layer is dried and passed through a pad of magnesium silicate. The solvent is evaporated to a residue which is crystallized from hexane to give 2.0 g of the desired product as a white solid.

EXAMPLE 56

3-[[2-[[[4-(Hexadecyloxy)phenoxy]acetyl]amino]-phenyl]methyl]-5-methyl-thiazolium bromide A mixture of 1.8 g of N-[2-(bromomethyl)phenyl]-2-[4-(hexadecyloxy)phenoxy]acetamide and 1.59 g of 5-methyl thiazole in 25 ml of toluene is refluxed under argon for 6 hours. The solvent is evaporated to a residue which is stirred with ether and the solid collected by centrifugation, washed with ether and vacuum dried to give 1.7 g of the desired product as an off-white solid, m.p. 121°-124° C.

According to the methods outlined hereinabove in Flowsheet F and described in detail in Examples 47–56, the compounds of this invention listed hereinbelow in List 4 can be prepared. These methods are applicable to the preparation of the compounds of this invention by one skilled in the art.

List 4

3-[[2-[[[-4-(tetradecyloxy)phenoxy]acetyl]amino]-phenyl]methyl]thiazolium bromide
3-[[2-[[[-3-(tetradecyloxy)phenoxy]acetyl]amino]-phenyl]methyl]thiazolium bromide
3-[[2-[[[-2-(tetradecyloxy)phenoxy]acetyl]amino]-phenyl]methyl]thiazolium bromide
3-[[2-[[[3-chloro-4-(tetradecyloxy)phenoxy]acetyl-]amino]phenyl]methyl]thiazolium bromide
3-[[2-[[[3-fluoro-2-(tetradecyloxy)phenoxy]acetyl-]amino]phenyl]methyl]thiazolium bromide
3-[[2-[[[3-t-butyl-2-(tetradecyloxy)phenoxy]acetyl-]amino]phenyl]methyl]thiazolium bromide
3-[[2-[[[3-methoxy-4-(tetradecyloxy)phenoxy]acetyl-]amino]phenyl]methyl]thiazolium bromide
3-[[2-[[[3-methoxy-2-(tetradecyloxy)phenoxy]acetyl-]amino]phenyl]methyl]thiazolium bromide
3-[[2-[[[2-chloro-4-(tetradecyloxy)phenoxy]acetyl-]amino]phenyl]methyl]thiazolium bromide
3-[[2-[[[4-chloro-3-(tetradecyloxy)phenoxy]acetyl-]amino]phenyl]methyl]thiazolium bromide
3-[[2-[[[4-t-butyl-2-(tetradecyloxy)phenoxy]acetyl-]amino]phenyl]methyl]thiazolium bromide
3-[[2-[[[4-methoxy-3-(tetradecyloxy)phenoxy]acetyl-]amino]phenyl]methyl]thiazolium bromide
3-[[2-[[[4-methoxy-2-(tetradecyloxy)phenoxy]acetyl-]amino]phenyl]methyl]thiazolium bromide
3-[[3-[[[-4-(tetradecyloxy)phenoxy]acetyl]amino]-phenyl]methyl]thiazolium bromide
3-[[3-[[[-3-(tetradecyloxy)phenoxy]acetyl]amino]-phenyl]methyl]thiazolium bromide
3-[[3-[[[3-chloro-2-(tetradecyloxy)phenoxy]acetyl-]amino]phenyl]methyl]thiazolium bromide
3-[[3-[[[3-fluoro-4-(tetradecyloxy)phenoxy]acetyl-]amino]phenyl]methyl]thiazolium bromide
3-[[3-[[[3-fluoro-2-(tetradecyloxy)phenoxy]acetyl-]amino]phenyl]methyl]thiazolium bromide
3-[[3-[[[3-methoxy-4-(tetradecyloxy)phenoxy]acetyl-]amino]phenyl]methyl]thiazolium bromide
3-[[3-[[[3-methoxy-2-(tetradecyloxy)phenoxy]acetyl-]amino]phenyl]methyl]thiazolium bromide
3-[[3-[[[2-chloro-4-(tetradecyloxy)phenoxy]acetyl-]amino]phenyl]methyl]thiazolium bromide
3-[[3-[[[4-t-butyl-3-(tetradecyloxy)phenoxy]acetyl-]amino]phenyl]methyl]thiazolium bromide
3-[[3-[[[4-t-butyl-2-(tetradecyloxy)phenoxy]acetyl-]amino]phenyl]methyl]thiazolium bromide
3-[[3-[[[4-methoxy-3-(tetradecyloxy)phenoxy]acetyl-]amino]phenyl]methyl]thiazolium bromide
3-[[4-[[[-4-(tetradecyloxy)phenoxy]acetyl]amino]-phenyl]methyl]thiazolium bromide
3-[[4-[[[-4-(hexadecyloxy)phenoxy]acetyl]amino]-phenyl]methyl]thiazolium bromide
3-[[4-[[[-3-(tetradecyloxy)phenoxy]acetyl]amino]-phenyl]methyl]thiazolium bromide
3-[[4-[[[-3-(hexadecyloxy)phenoxy]acetyl]amino]-phenyl]methyl]thiazolium bromide
3-[[4-[[[-2-(tetradecyloxy)phenoxy]acetyl]amino]-phenyl]methyl]thiazolium bromide
3-[[4-[[[-2-(hexadecyloxy)phenoxy]acetyl]amino]-phenyl]methyl]thiazolium bromide
3-[[4-[[[3-chloro-4-(tetradecyloxy)phenoxy]acetyl-]amino]phenyl]methyl]thiazolium bromide
3-[[4-[[[3-chloro-4-(hexadecyloxy)phenoxy]acetyl-]amino]phenyl]methyl]thiazolium bromide
3-[[4-[[[3-chloro-2-(tetradecyloxy)phenoxy]acetyl-]amino]phenyl]methyl]thiazolium bromide
3-[[4-[[[3-acetyl-2-(tetradecyloxy)phenoxy]acetyl-]amino]phenyl]methyl]thiazolium bromide
3-[[4-[[[3-acetyl-2-(hexadecyloxy)phenoxy]acetyl-]amino]phenyl]methyl]thiazolium bromide
3-[[4-[[[3-t-butyl-4-(tetradecyloxy)phenoxy]acetyl-]amino]phenyl]methyl]thiazolium bromide
3-[[4-[[[3-t-butyl-4-(hexadecyloxy)phenoxy]acetyl-]amino]phenyl]methyl]thiazolium bromide
3-[[4-[[[3-t-butyl-2-(tetradecyloxy)phenoxy]acetyl-]amino]phenyl]methyl]thiazolium bromide
3-[[4-[[[3-methoxy-4-(hexadecyloxy)phenoxy]acetyl-]amino]phenyl]methyl]thiazolium bromide
3-[[4-[[[3-methoxy-2-(tetradecyloxy)phenoxy]acetyl-]amino]phenyl]methyl]thiazolium bromide
3-[[4-[[[3-methoxy-2-(hexadecyloxy)phenoxy]acetyl-]amino]phenyl]methyl]thiazolium bromide
3-[[4-[[[2-chloro-4-(tetradecyloxy)phenoxy]acetyl-]amino]phenyl]methyl]thiazolium bromide
3-[[4-[[[2-chloro-4-(hexadecyloxy)phenoxy]acetyl-]amino]phenyl]methyl]thiazolium bromide
3-[[4-[[[4-chloro-3-(tetradecyloxy)phenoxy]acetyl-]amino]phenyl]methyl]thiazolium bromide
3-[[4-[[[4-chloro-3-(hexadecyloxy)phenoxy]acetyl-]amino]phenyl]methyl]thiazolium bromide
3-[[4-[[[4-chloro-2-(tetradecyloxy)phenoxy]acetyl-]amino]phenyl]methyl]thiazolium bromide
3-[[4-[[[4-t-butyl-3-(tetradecyloxy)phenoxy]acetyl-]amino]phenyl]methyl]thiazolium bromide
5-Methyl-3-[[2-[[[-4-(tetradecyloxy)phenoxy]acetyl-]amino]phenyl]methyl]thiazolium bromide
5-Methyl-3-[[2-[[[-3-(tetradecyloxy)phenoxy]acetyl-]amino]phenyl]methyl]thiazolium bromide
5-Methyl-3-[[2-[[[-2-(tetradecyloxy)phenoxy]acetyl-]amino]phenyl]methyl]thiazolium bromide
5-Methyl-3-[[2-[[[3-chloro-4-(tetradecyloxy)phenox-y]acetyl]amino]phenyl]methyl]thiazolium bromide
5-Methyl-3-[[2-[[[3-chloro-2-(tetradecyloxy)phenox-y]acetyl]amino]phenyl]methyl]thiazolium bromide
5-Methyl-3-[[2-[[[3-fluoro-4-(tetradecyloxy)phenox-y]acetyl]amino]phenyl]methyl]thiazolium bromide
5-Methyl-3-[[2-[[[3-fluoro-2-(tetradecyloxy)phenox-y]acetyl]amino]phenyl]methyl]thiazolium bromide
5-Methyl-3-[[2-[[[3-acetyl-2-(tetradecyloxy)phenox-y]acetyl]amino]phenyl]methyl]thiazolium bromide
5-Methyl-3-[[2-[[[3-t-butyl-4-(tetradecyloxy)phenox-y]acetyl]amino]phenyl]methyl]thiazolium bromide
5-Methyl-3-[[2-[[[3-t-butyl-2-(tetradecyloxy)phenox-y]acetyl]amino]phenyl]methyl]thiazolium bromide
5-Methyl-3-[[2-[[[3-methoxy-4-(tetradecyloxy)phenox-y]acetyl]amino]phenyl]methyl]thiazolium bromide
5-Methyl-3-[[2-[[[3-methoxy-2-(tetradecyloxy)phenox-y]acetyl]amino]phenyl]methyl]thiazolium bromide
5-Methyl-3-[[2-[[[2-chloro-4-(tetradecyloxy)phenox-y]acetyl]amino]phenyl]methyl]thiazolium bromide
5-Methyl-3-[[2-[[[4-chloro-3-(tetradecyloxy)phenox-y]acetyl]amino]phenyl]methyl]thiazolium bromide
5-Methyl-3-[[2-[[[4-t-butyl-2-(tetradecyloxy)phenox-y]acetyl]amino]phenyl]methyl]thiazolium bromide
5-Methyl-3-[[2-[((4-methoxy-3-(tetradecyloxy)phenox-y)acetyl)amino]Phenyl)methyl]thiazolium bromide
5-Methyl-3-[[3-[[[-3-(dodecyloxy)phenoxy]acetyl-]amino]phenyl]methyl]thiazolium bromide
5-Methyl-3-[[3-[[[-4-(tetradecyloxy)phenoxy]acetyl-]amino]phenyl]methyl]thiazolium bromide
5-Methyl-3-[[3-[[[-2-(dodecyloxy)phenoxy]acetyl-]amino]phenyl]methyl]thiazolium bromide
5-Methyl-3-[[3-[[[3-chloro-2-(tetradecyloxy)phenox-y]acetyl]amino]phenyl]methyl]thiazolium bromide 5-Methyl-3-[[3-[[[3-chloro-2-(dodecyloxy)phenoxy]acetyl]amino]phenyl]methyl]thiazolium bromide
5-Methyl-3-[[3-[[[3-fluoro-4-(tetradecyloxy)phenoxy]acetyl]amino]phenyl]methyl]thiazolium bromide
5-Methyl-3-[[3-[[[3-fluoro-4-(dodecyloxy)phenoxy]acetyl]amino]phenyl]methyl]thiazolium bromide
5-Methyl-3-[[3-[[[3-fluoro-2-(tetradecyloxy)phenoxy]acetyl]amino]phenyl]methyl]thiazolium bromide
5-Methyl-3-[[3-[[[3 -fluoro-2-(dodecyloxy)phenoxy]acetyl]amino]phenyl]methyl]thiazolium bromide
5-Methyl-3-[[3-[[[3-acetyl-4-(tetradecyloxy)phenoxy]acetyl]amino]phenyl]methyl]thiazolium bromide
5-Methyl-3-[[3-[[[3-acetyl-4-(dodecyloxy)phenoxy]acetyl]amino]phenyl]methyl]thiazolium bromide
5-Methyl-3-[[3-[[[3-acetyl-2-(tetradecyloxy)phenoxy]acetyl]amino]phenyl]methyl]thiazolium bromide
5-Methyl-3-[[3-[[[3-t-butyl-4-(dodecyloxy)phenoxy]acetyl]amino]phenyl]methyl]thiazolium bromide
5-Methyl-3-[[3-[[[2-chloro-4-(tetradecyloxy)phenoxy]acetyl]amino]phenyl]methyl]thiazolium bromide
5-Methyl-3-[[3-[[[4-chloro-3-(dodecyloxy)phenoxy]acetyl]amino]phenyl]methyl]thiazolium bromide
5-Methyl-3-[[3-[[[4-chloro-2-(tetradecyloxy)phenoxy]acetyl]amino]phenyl]methyl]thiazolium bromide
5-Methyl-3-[[3-[[[4-chloro-2-(dodecyloxy)phenoxy]acetyl]amino]phenyl]methyl]thiazolium bromide
5-Methyl-3-[[3-[[[4-t-butyl-3-(decyloxy)phenoxy]acetyl]amino]phenyl]methyl]thiazolium bromide
5-Methyl-3-[[3-[[[4-t-butyl-3-(dodecyloxy)phenoxy]acetyl]amino]phenyl]methyl]thiazolium bromide
5-Methyl-3-[[3-[[[4-t-butyl-2-(tetradecyloxy)phenoxy]acetyl]amino]phenyl]methyl]thiazolium bromide
5-Methyl-3-[[3-[[[4-t-butyl-2-(dodecyloxy)phenoxy]acetyl]amino]phenyl]methyl]thiazolium bromide
5-Methyl-3-[[3-[[[4-methoxy-3-(tetradecyloxy)phenoxy]acetyl]amino]phenyl]methyl]thiazolium bromide
5-Methyl-3-[[3-[[[4-methoxy-3-(dodecyloxy)phenoxy]acetyl]amino]phenyl]methyl]thiazolium bromide
5-Methyl-3-[[3-[[[4-methoxy-2-(tetradecyloxy)phenoxy]acetyl]amino]phenyl]methyl]thiazolium bromide
5-Methyl-3-[[3-[[[4-methoxy-2-(dodecyloxy)phenoxy]acetyl]amino]phenyl]methyl]thiazolium bromide
5-Methyl-3-[[4-[[[-4-(tetradecyloxy)phenoxy]acetyl]amino]phenyl]methyl]thiazolium bromide
5-Methyl-3-[[4-[[[-3-(tetradecyloxy)phenoxy]acetyl]amino]phenyl]methyl]thiazolium bromide
5-Methyl-3-[[4-[[[-2-(tetradecyloxy)phenoxy]acetyl]amino]phenyl]methyl]thiazolium bromide
5-Methyl-3-[[4-[[[3-acetyl-4-(tetradecyloxy)phenoxy]acetyl]amino]phenyl]methyl]thiazolium bromide
5-Methyl-3-[[4-[[[3-acetyl-2-(tetradecyloxy)phenoxy]acetyl]amino]phenyl]methyl]thiazolium bromide
5-Methyl-3-[[4-[[[3-t-butyl-4-(tetradecyloxy)phenoxy]acetyl]amino]phenyl]methyl]thiazolium bromide
5-Methyl-3-[[4-[[[3-t-butyl-2-(tetradecyloxy)phenoxy]acetyl]amino]phenyl]methyl]thiazolium bromide
5-Methyl-3-[[4-[[[3-methoxy-4-(tetradecyloxy)phenoxy]acetyl]amino]phenyl]methyl]thiazolium bromide
5-Methyl-3-[[4-[[[3-methoxy-2-(tetradecyloxy)phenoxy]acetyl]amino]phenyl]methyl]thiazolium bromide
5-Methyl-3-[[4-[[[2-chloro-4-(tetradecyloxy)phenoxy]acetyl]amino]phenyl]methyl]thiazolium bromide
5-Methyl-3-[[4-[[[4-chloro-3-(tetradecyloxy)phenoxy]acetyl]amino]phenyl]methyl]thiazolium bromide
5-Methyl-3-[[4-[[[4-chloro-2-(tetradecyloxy)phenoxy]acetyl]amino]phenyl]methyl]thiazolium bromide
5-Methyl-3-[[4-[[[4-t-butyl-3-(tetradecyloxy)phenoxy]acetyl]amino]phenyl]methyl]thiazolium bromide
5-Methyl-3-[[4-[[[4-t-butyl-2-(tetradecyloxy)phenoxy]acetyl]amino]phenyl]methyl]thiazolium bromide
5-Methyl-3-[[4-[[[4-methoxy-3-(tetradecyloxy)phenoxy]acetyl]amino]phenyl]methyl]thiazolium bromide
5-Methyl-3-[[4-[[[4-methoxy-2-(tetradecyloxy)phenoxy]acetyl]amino]phenyl]methyl]thiazolium bromide
2-Methyl-3-[[2-[[[-4-(tetradecyloxy)phenoxy]acetyl]amino]phenyl]methyl]thiazolium bromide
2-Methyl-3-[[2-[[[3-chloro-4-(tetradecyloxy)phenoxy]acetyl]amino]phenyl]methyl]thiazolium bromide
2-Methyl-3-[[2-[[[3-t-butyl-2-(tetradecyloxy)phenoxy]acetyl]amino]phenyl]methyl]thiazolium bromide
2-Methyl-3-[[2-[[[3-methoxy-4-(tetradecyloxy)phenoxy]acetyl]amino]phenyl]methyl]thiazolium bromide
2-Methyl-3-[[2-[[[3-methoxy-2-(tetradecyloxy)phenoxy]acetyl]amino]phenyl]methyl]thiazolium bromide
2-Methyl-3-[[2-[[[2-chloro-4-(tetradecyloxy)phenoxy]acetyl]amino]phenyl]methyl]thiazolium bromide
2-Methyl-3-[[2-[[[4-chloro-3-(tetradecyloxy)phenoxy]acetyl]amino]phenyl]methyl]thiazolium bromide
2-Methyl-3-[[2-[[[4-chloro-2-(tetradecyloxy)phenoxy]acetyl]amino]phenyl]methyl]thiazolium bromide
2-Methyl-3-[[2-[[[4-t-butyl-3-(tetradecyloxy)phenoxy]acetyl]amino]phenyl]methyl]thiazolium bromide
2-Methyl-3-[[2-[[[4-methoxy-2-(tetradecyloxy)phenoxy]acetyl]amino]phenyl]methyl]thiazolium bromide
2-Methyl-3-[[3-[[[-4-(tetradecyloxy)phenoxy]acetyl]amino]phenyl]methyl]thiazolium bromide
2-Methyl-3-[[3-[[[-3-(tetradecyloxy)phenoxy]acetyl]amino]phenyl]methyl]thiazolium bromide
2-Methyl-3-[[3-[[[-2-(tetradecyloxy)phenoxy]acetyl]amino]phenyl]methyl]thiazolium bromide
2-Methyl-3-[[3-[[[3-chloro-4-(tetradecyloxy)phenoxy]acetyl]amino]phenyl]methyl]thiazolium bromide
2-Methyl-3 -[[3 -[[[3 -chloro-2-(tetradecyloxy)phenoxy]acetyl]amino]phenyl]methyl]thiazolium bromide
2-Methyl-3-[[3-[[[3-fluoro-4-(tetradecyloxy)phenoxy]acetyl]amino]phenyl]methyl]thiazolium bromide
2-Methyl-3-[[3-[[[3-fluoro-2-(tetradecyloxy)phenoxy]acetyl]amino]phenyl]methyl]thiazolium bromide
2-Methyl-3-[[3-[[[2-chloro-4-(tetradecyloxy)phenoxy]acetyl]amino]phenyl]methyl]thiazolium bromide
2-Methyl-3-[[3-[[[4-t-butyl-3-(tetradecyloxy)phenoxy]acetyl]amino]phenyl]methyl]thiazolium bromide
2-Methyl-3-[[3-[[[4-t-butyl-2-(tetradecyloxy)phenoxy]acetyl]amino]phenyl]methyl]thiazolium bromide
2-Methyl-3-[[3-[[[4-methoxy-3-(tetradecyloxy)phenoxy]acetyl]amino]phenyl]methyl]thiazolium bromide
2-Methyl-3-[[3-[[[4-methoxy-2-(tetradecyloxy)phenoxy]acetyl]amino]phenyl]methyl]thiazolium bromide
2-Methyl-3-[[4-[[[-4-(tetradecyloxy)phenoxy]acetyl]amino]phenyl]methyl]thiazolium bromide
2-Methyl-3-[[4-[[[-3-(tetradecyloxy)phenoxy]acetyl]amino]phenyl]methyl]thiazolium bromide
2-Methyl-3-[[4-[[[-2-(tetradecyloxy)phenoxy]acetyl]amino]phenyl]methyl]thiazolium bromide
2-Methyl-3-[[4-[[[3-chloro-4-(tetradecyloxy)phenoxy]acetyl]amino]phenyl]methyl]thiazolium bromide
2-Methyl-3-[[4-[[[3-chloro-2-(tetradecyloxy)phenoxy]acetyl]amino]phenyl]methyl]thiazolium bromide
2-Methyl-3-[[4-[[[3-fluoro-4-(tetradecyloxy)phenoxy]acetyl]amino]phenyl]methyl]thiazolium bromide
2-Methyl-3-[[4-[[[3-fluoro-2-(tetradecyloxy)phenoxy]acetyl]amino]phenyl]methyl]thiazolium bromide
2-Methyl-3-[[4-[[[3-acetyl-4-(tetradecyloxy)phenoxy]acetyl]amino]phenyl]methyl]thiazolium bromide
2-Methyl-3-[[4-[[[3-acetyl-2-(tetradecyloxy)phenoxy]acetyl]amino]phenyl]methyl]thiazolium bromide 2-Methyl-3-[[4-[[[3-methoxy-4-(tetradecyloxy)phenoxy]acetyl]amino]phenyl]methyl]thiazolium bromide
2-Methyl-3-[[4-[[[4-methoxy-3-(tetradecyloxy)phenoxy]acetyl]amino]phenyl]methyl]thiazolium bromide
2-Methyl-3-[[4-[[[4-methoxy-2-(tetradecyloxy)phenoxy]acetyl]amino]phenyl]methyl]thiazolium bromide
4-Methyl-3-[[2-[[[-4-(tetradecyloxy)phenoxy]acetyl]amino]phenyl]methyl]thiazolium bromide
4-Methyl-3-[[2-[[[-3-(tetradecyloxy)phenoxy]acetyl]amino]phenyl]methyl]thiazolium bromide
4-Methyl-3-[[2-[[[-2-(tetradecyloxy)phenoxy]acetyl]amino]phenyl]methyl]thiazolium bromide
4-Methyl-3-[[2-[[[3-chloro-4-(tetradecyloxy)phenoxy]acetyl]amino]phenyl]methyl]thiazolium bromide
4-Methyl-3-[[2-[[[3-chloro-2-(tetradecyloxy)phenoxy]acetyl]amino]phenyl]methyl]thiazolium bromide
4-Methyl-3-[[2-[[[3-fluoro-4-(tetradecyloxy)phenoxy)acetyl)amino]Phenyl]methyl]thiazolium bromide
4-Methyl-3-[[2-[[[3-fluoro-2-(tetradecyloxy)phenoxy]acetyl]amino]phenyl]methyl]thiazolium bromide
4-Methyl-3-[[2-[[[3-acetyl-4-(tetradecyloxy)phenoxy]acetyl]amino]phenyl]methyl]thiazolium bromide
4-Methyl-3-[[2-[[[3-acetyl-2-(tetradecyloxy)phenoxy]acetyl]amino]phenyl]methyl]thiazolium bromide
4-Methyl-3-[[2-[[[3-t-butyl-4-(tetradecyloxy)phenoxy]acetyl]amino]phenyl]methyl]thiazolium bromide
4-Methyl-3-[[2-[[[3-t-butyl-2-(tetradecyloxy)phenoxy]acetyl]amino]phenyl]methyl]thiazolium bromide
4-Methyl-3-[[2-[[[3-methoxy-4-(tetradecyloxy)phenoxy]acetyl]amino]phenyl]methyl]thiazolium bromide
4-Methyl-3-[[2-[[[3-methoxy-2-(tetradecyloxy)phenoxy]acetyl]amino]phenyl]methyl]thiazolium bromide
4-Methyl-3-[[2-[[[4-methoxy-2-(tetradecyloxy)phenoxy]acetyl]amino]phenyl]methyl]thiazolium bromide
4-Methyl-3-[[3-[[[-4-(tetradecyloxy)phenoxy]acetyl]amino]phenyl]methyl]thiazolium bromide
4-Methyl-3-[[3-[[[-3-(tetradecyloxy)phenoxy]acetyl]amino]phenyl]methyl]thiazolium bromide
4-Methyl-3-[[3-[[[-2-(tetradecyloxy)phenoxy]acetyl]amino]phenyl]methyl]thiazolium bromide
4-Methyl-3-[[3-[[[3-chloro-4-(octyloxy)phenoxy]acetyl]amino]phenyl]methyl]thiazolium bromide
4-Methyl-3-[[3-[[[3-chloro-2-(tetradecyloxy)phenoxy]acetyl]amino]phenyl]methyl]thiazolium bromide
4-Methyl-3-[[3-[[[3-fluoro-4-(tetradecyloxy)phenoxy]acetyl]amino]phenyl]methyl]thiazolium bromide
4-Methyl-3-[[3-[[[3-fluoro-2-(tetradecyloxy)phenoxy]acetyl]amino]phenyl]methyl]thiazolium bromide
4-Methyl-3-[[3-[[[3-acetyl-4-(tetradecyloxy)phenoxy]acetyl]amino]phenyl]methyl]thiazolium bromide
4-Methyl-3-[[3-[[[3-acetyl-2-(tetradecyloxy)phenoxy]acetyl]amino]phenyl]methyl]thiazolium bromide
4-Methyl-3-[[3-[[[3-t-butyl-4-(decyloxy)phenoxy]acetyl]amino]phenyl]methyl]thiazolium bromide
4-Methyl-3-[[3-[[[3-t-butyl-2-(tetradecyloxy)phenoxy]acetyl]amino]phenyl]methyl]thiazolium bromide
4-Methyl-3-[[3-[[[3-methoxy-2-(tetradecyloxy)phenoxy)acetyl)amino]Phenyl]methyl]thiazolium bromide
4-Methyl-3-[[3-[[[2-chloro-4-(tetradecyloxy)phenoxy)acetyl)amino]phenyl)methyl]thiazolium bromide
4-Methyl-3-[[3-[[[4-chloro-3-(tetradecyloxy)phenoxy)acetyl)amino]phenyl)methyl]thiazolium bromide
4-Methyl-3-[[3-[[[4-chloro-2-(tetradecyloxy)phenoxy]acetyl]amino]phenyl]methyl]thiazolium bromide
4-Methyl-3-[[4-[[[-2-(tetradecyloxy)phenoxy]acetyl]amino]phenyl]methyl]thiazolium bromide
4-Methyl-3-[[4-[[[3-chloro-4-(tetradecyloxy)phenoxy]acetyl]amino]phenyl]methyl]thiazolium bromide
4-Methyl-3-[[4-[[[3-chloro-2-(tetradecyloxy)phenoxy]acetyl]amino]phenyl]methyl]thiazolium bromide
4-Methyl-3-[[4-[[[3-fluoro-4-(tetradecyloxy)phenoxy]acetyl]amino]phenyl]methyl]thiazolium bromide
phenoxy]acetyl [4-[[[3-acetyl-4-(tetradecyloxy)phenoxy]acetyl]amino]phenyl]methyl]thiazolium bromide
4-Methyl-3-[[4-[[[3-acetyl-2-(tetradecyloxy)phenoxy]acetyl]amino]phenyl]methyl]thiazolium bromide
4-Methyl-3-[[4-[[[3-t-butyl-4-(tetradecyloxy)phenoxy]acetyl]amino]phenyl]methyl]thiazolium bromide
4-Methyl-3-[[4-[[[3-t-butyl-2-(tetradecyloxy)phenoxy]acetyl]amino]phenyl]methyl]thiazolium bromide
4-Methyl-3-[[4-[[[3-methoxy-4-(tetradecyloxy)phenoxy]acetyl]amino]phenyl]methyl]thiazolium bromide
4-Methyl-3-[[4-[[[3-methoxy-2-(tetradecyloxy)phenoxy]acetyl]amino]phenyl]methyl]thiazolium bromide
4-Methyl-3-[[4-[[[2-chloro-4-(tetradecyloxy)phenoxy]acetyl]amino]phenyl]methyl]thiazolium bromide
4-Methyl-3-[[4-[[[4-chloro-3-(dodecyloxy)phenoxy]acetyl]amino]phenyl]methyl]thiazolium bromide
4-Methyl-3-[[4-[[[4-chloro-2-(tetradecyloxy)phenoxy]acetyl]amino]phenyl]methyl]thiazolium bromide
4-Methyl-3-[[4-[[[4-t-butyl-2-(tetradecyloxy)phenoxy]acetyl]amino]phenyl]methyl]thiazolium bromide

EXAMPLE 57

3-[[2-[4-(Tetradecyloxy)phenyl]ethyl]aminobenzenemethanol

To a solution of 42.36 ml of 1 molar lithium aluminum hydride in ether is added dropwise under argon over 20 minutes a solution of ethyl 3-[[[4-(tetradecyloxy)phenyl]acetyl]amino]benzoate in 50 ml of ether and 50 ml of tetrahydrofuran. The mixture is refluxed for 3 hours, cooled to 0° C. and ethyl acetate added. Saturated sodium sulfate is added followed by ether. The mixture is filtered and the cake washed with ether. The filtrate is evaporated and the residue chromatographed on silica gel using 9:1 chloroform:ethyl acetate. The product fractions are combined and evaporated to a residue which is crystallized from hexane to give 4.5 g of the desired product as a white solid, m.p. 67°–70° C.

EXAMPLE 58

N-[3-(Bromomethyl)phenyl-N-[2-[4-(tetradecyloxy)phenyl]ethyl]acetamide

A mixture of 4 g of 3-[[2-[4-(tetradecyloxy)phenyl]ethyl]aminobenzenemethanol, 3.71 g of acetic anhydride and 2.3 g of triethylamine in 50 ml of chloroform is refluxed for 3 hours. The solvent is evaporated to a residue which is mixed with 15 ml of 30% HBr in acetic acid followed by heating at 80° C. for 2.5 hours. The mixture is poured into water and extracted with ether. The organic layer is washed with saturated sodium bicarbonate, dried and evaporated to a residue which is crystallized from hexanes to give 4.4 g of the desired product as a white solid, m.p. 75°–77° C.

EXAMPLE 59

3-[[3-[Acetyl[2-(4-(tetradecyloxy)phenyl]ethyl]amino]phenyl]methyl]-5-methyl-thiazolium bromide A mixture of 2.5 g N-[3-(bromomethyl)phenyl-N-[2-[4-(tetradecyloxy)phenyl]ethyl]acetamide and 2.28 g of 5-methylthiazole in 50 ml of toluene is refluxed for 5 hours, cooled and ether added. The solid is collected by centrifugation and washed several times with ether then vacuum dried to give 1.8 g of the desired product as a white solid, m.p. 136°-140° C.

According to the methods outlined hereinabove in Flowsheet C and described in detail in Examples 57-59, the compounds of this invention listed hereinbelow in List 5 can be prepared. These methods are applicable to the preparation of the compounds of this invention by one skilled in the art.

List 5

3-[[4-[acetyl[2-[4-(tetradecyloxy)phenyl]ethyl]amino]phenyl]methyl]thiazolium bromide
3-[[4-[acetyl [2-[4-(tetradecyloxy)phenyl]ethyl]amino]phenyl)methyl]-5-methyl-thiazolium bromide
3-[[4-[acetyl [2-[4-(dodecyloxy)phenyl]ethyl]amino]phenyl]methyl]thiazolium bromide
3-[[4-[acetyl[2-[4-(hexadecyloxy)phenyl]ethyl]amino]phenyl]methyl]-5-methyl-thiazolium bromide
3-[[4-[acetyl [2-[3-(tetradecyloxy)phenyl]ethyl]amino]phenyl]methyl]thiazolium bromide
3-[[4-[acetyl [2-[3-(tetradecyloxy)phenyl]ethyl]amino]phenyl]methyl]-5-methyl-thiazolium bromide
3-[[4-[acetyl[2-[3-(dodecyloxy)phenyl]ethyl]amino]phenyl]methyl]thiazolium bromide
3-[[4-[acetyl [2-[3-(dodecyloxy)phenyl]ethyl]amino]phenyl]methyl]-5-methyl-thiazolium bromide
3-[[4-[acetyl [2-[3-chloro-4-(tetradecyloxy)phenyl]ethyl]amino]phenyl]methyl]thiazolium bromide
3-[[4-[acetyl[2-[3-chloro-4-(tetradecyloxy)phenyl]ethyl]amino]phenyl]methyl]-5-methyl-thiazolium bromide
3-[[4-[acetyl[2-[3-fluoro-4-(tetradecyloxy)phenyl]ethyl]amino]phenyl]methyl]thiazolium bromide
3-[[4-[acetyl[2-[3-fluoro-4-(tetradecyloxy)phenyl]ethyl]amino]phenyl]methyl]-5-methyl-thiazolium bromide
3-[[4-[acetyl[2-[3-t-butyl-4-(tetradecyloxy)phenyl]ethyl]amino]phenyl]methyl]thiazolium bromide
3-[[4-[acetyl[2-[3-t-butyl-4-(tetradecyloxy)phenyl]ethyl]amino]phenyl]methyl]-5-methyl-thiazolium bromide
3-[[4-[acetyl[2-[3-methoxy-4-(tetradecyloxy)phenyl]ethyl]amino]phenyl]methyl]thiazolium bromide
3-[[4-[acetyl [2-[3-methoxy-4-(tetradecyloxy)phenyl]ethyl]amino]phenyl]methyl]-5-methyl -thiazolium bromide
3-[[4-[acetyl[2-[4-chloro-3-(tetradecyloxy)phenyl]ethyl]amino]phenyl]methyl]thiazolium bromide
3-[[4-[acetyl [2-[4-chloro-3-(tetradecyloxy)phenyl]ethyl]amino]phenyl]methyl]-5-methyl-thiazolium bromide
3-[[4-[acetyl [2-[4-t-butyl-3-(tetradecyloxy)phenyl]ethyl]amino]phenyl]methyl]thiazolium bromide
3-[[4-[acetyl [2-[4-t-butyl-3-(tetradecyloxy)phenyl]ethyl]amino]phenyl]methyl]-5-methyl-thiazolium bromide
3-[[4-[acetyl [2-[4-methoxy-3-(tetradecyloxy)phenyl]ethyl]amino]phenyl]methyl]thiazolium bromide
3-[[4-[acetyl [2-[4-methoxy-3-(tetradecyloxy)phenyl]ethyl]amino]phenyl]methyl]-5-methyl-thiazolium bromide
3-[[3-[acetyl [2-[4-(tetradecyloxy)phenyl]ethyl]amino]phenyl]methyl]thiazolium bromide
3-[[3-[acetyl[2-[4-(tetradecyloxy)phenyl]ethyl]amino]phenyl]methyl]-5-methyl-thiazolium bromide
3-[[3-[acetyl[2-[4-(hexadecyloxy)phenyl]ethyl]amino]phenyl]methyl]thiazolium bromide
3-[[3-[acetyl [2-[4-(dodecyloxy)phenyl]ethyl]amino]phenyl]methyl]-5-methyl-thiazolium bromide
3-[[3-[acetyl [2-[3-(tetradecyloxy)phenyl]ethyl]amino]phenyl]methyl]thiazolium bromide
3-[[3-[acetyl [2-[3-(tetradecyloxy)phenyl]ethyl]amino]phenyl]methyl]-5-methyl-thiazolium bromide
3-[[3-[acetyl [2-[3-(hexadecyloxy)phenyl]ethyl]amino]phenyl]methyl]thiazolium bromide
3-[[3-[acetyl [2-[3-(hexadecyloxy)phenyl]ethyl]amino]phenyl]methyl]-5-methyl-thiazolium bromide
3-[[3-[acetyl[2-[3-chloro-4-(tetradecyloxy)phenyl]ethyl]amino]phenyl]methyl]thiazolium bromide
3-[[3 -[acetyl [2-[3-chloro-4-(tetradecyloxy)phenyl]ethyl]amino]phenyl]methyl]-5-methyl-thiazolium bromide
3-[[3-[acetyl [2-[3-chloro-4-(hexadecyloxy)phenyl]ethyl]amino]phenyl]methyl]thiazolium bromide
3-[[3-[acetyl[2-[3-chloro-4-(hexadecyloxy)phenyl]ethyl]amino]phenyl]methyl]-5-methyl-thiazolium bromide
3-[[3-[acetyl [2-[3-fluoro-4-(tetradecyloxy)phenyl]ethyl]amino]phenyl]methyl]thiazolium bromide
3-[[3-[acetyl[2-[3-fluoro-4-(tetradecyloxy)phenyl]ethyl]amino]phenyl]methyl]-5-methyl-thiazolium bromide
3-[[3-[acetyl[2-[3-t-butyl-4-(tetradecyloxy)phenyl]ethyl]amino]phenyl]methyl]thiazolium bromide
3-[[3-[acetyl[2-[3-t-butyl-4-(tetradecyloxy)phenyl]ethyl]amino]phenyl]methyl]-5-methyl-thiazolium bromide
3-[[3-[acetyl[2-[3-methoxy-4-(tetradecyloxy)phenyl]ethyl]amino]phenyl]methyl]thiazolium bromide
3-[[3-[acetyl[2-[3-methoxy-4-(tetradecyloxy)phenyl]ethyl]amino]phenyl]methyl]-5-methyl-thiazolium bromide
3-[[3-[acetyl[2-[4-chloro-3-(tetradecyloxy)phenyl]ethyl]amino]phenyl]methyl]thiazolium bromide
3-[[3-[acetyl[2-[4-chloro-3-(tetradecyloxy)phenyl]ethyl]amino]phenyl]methyl]-5-methyl-thiazolium bromide
3-[[3-[acetyl[2-[4-t-butyl-3-(tetradecyloxy)phenyl]ethyl]amino]phenyl]methyl]thiazolium bromide
3-[[3-[acetyl [2-[4-t-butyl-3-(tetradecyloxy)phenyl]ethyl]amino]phenyl]methyl]-5-methyl-thiazolium bromide
3-[[3-[acetyl [2-[4-methoxy-3-(tetradecyloxy)phenyl]ethyl]amino]phenyl]methyl]thiazolium bromide
3-[[3-[acetyl [2-[4-methoxy-3-(tetradecyloxy)phenyl]ethyl]amino]phenyl]methyl]-5-methyl-thiazolium bromide
3-[[3-[propionyl[[4-methoxy-3-(tetradecyloxy)phenyl]ethyl]amino]phenyl]methyl]-5-methyl-thiazolium bromide
3-[[2-[acetyl [2-[4-(tetradecyloxy)phenyl]ethyl]amino]phenyl]methyl]-5-methyl-thiazolium bromide
3-[[2-[acetyl [2-[3-(tetradecyloxy)phenyl]ethyl]amino]phenyl]methyl]-5-methyl-thiazolium bromide
3-[[2-[acetyl [2-[3-chloro-4-(tetradecyloxy)phenyl]ethyl]amino]phenyl]methyl]-5-methyl-thiazolium bromide
3-[[2-[acetyl[2-[3-fluoro-4-(tetradecyloxy)phenyl]ethyl]amino]phenyl]methyl]-5-methyl-thiazolium bromide
3-[[2-[acetyl [2-[3-methoxy-4-(tetradecyloxy)phenyl]ethyl]amino]phenyl]methyl]-5-methyl-thiazolium bromide
3-[[2-[acetyl[2-[4-chloro-3-(tetradecyloxy)phenyl]ethyl]amino]phenyl]methyl]-5-methyl-thiazolium bromide
3-[[2-[acetyl [2-[4-methoxy-3-(tetradecyloxy)phenyl]ethyl]amino]phenyl]methyl]-5-methyl-thiazolium bromide

EXAMPLE 60

N'-Methyl-N-[[3-[[[(methylamino)carbonyl]oxy]methyl]phenyl]-N-[[4-(tetradecyloxy)phenyl]methyl]urea A mixture of 8 g of 3-[[[4-(tetradecyloxy)phenyl]methyl]aminobenzenemethanol and 3.22 g of methyl isocyanate in 10 ml of pyridine and 20 ml of ether is stirred at room temperature overnight. The mixture is poured into water and extracted with ether:tetrahydrofuran. The organic layer is washed with dilute hydrochloric acid and brine. The organic layer is dried and evaporated to a residue which is crystallized from hexane:carbon tetrachloride to give 8.7 g of the desired product as a white powder, m.p. 107°–109° C.

EXAMPLE 61

N-[3-(Hydroxymethyl)phenyl]-N'-methyl-N-[4-(tetradecyloxy)phenyl]urea

A mixture of 7.8 g of N'-methyl-N-[3-[[[(methylamino)carbonyl]oxy]methyl]phenyl]-N-[[4-(tetradecyloxy)phenyl]methyl]urea and 768.77 mg of sodium hydroxide in 100 ml of ethyl alcohol and 10 ml of water is refluxed for 6 hours. The mixture is poured into water and extracted with ether:tetrahydrofuran. The organic layer is washed with brine, dried and evaporated to a residue which is crystallized from carbon tetrachloride:hexane to give 6.9 g of the desired product as a white solid.

EXAMPLE 62

N-[3-(Bromomethyl)phenyl]-N'-methyl-N-[[4-(tetradecyloxy)phenyl]methyl]urea

To a solution of N-[3-(hydroxymethyl)phenyl]-N'-methyl-N-[4-(tetradecyloxy)phenyl]urea and 1.64 g of methanesulfonyl chloride in 100 ml of tetrahydrofuran is added 1.45 g of triethylamine followed by stirring at room temperature for 1.5 hours. Added 10.8 g of lithium bromide and stirred at room temperature for 4 hours. The mixture is poured into water and extracted with ether. The organic layer is dried and evaporated to a residue which is purified by chromatography on silica gel using 3:1 hexane:ethyl acetate to give 3.5 g of the desired product as a white solid, m.p. 70°–73° C.

EXAMPLE 63

5-Methyl-3-[[3-[[[(methylamino)carbonyl]-[[4-(tetradecyloxy]phenyl]methyl]amino]phenyl]methyl]-thiazolium bromide A mixture of 3.3 g of N-[3-(bromomethyl)phenyl]-N'-methyl-N-[[4-(tetradecyloxy)phenyl]methyl]urea and 2.1 g of 5-methylthiazole in 50 ml of acetonitrile is refluxed under argon for 5 hours. The mixture is allowed to stand at room temperature overnight. The mixture is diluted with ether and the solid collected. The solid is washed several times with ether then vacuum dried to give 3.7 g of the desired product as a white solid, m.p. 124°–126° C.

According to the methods outlined hereinabove in Flowsheet C and described in detail in Examples 60–63, the compounds of this invention listed hereinbelow in List 6 can be prepared. These methods are applicable to the preparation of the compounds of this invention by one skilled in the art.

List 6

3-[[4-[[(methylamino)carbonyl][[4-(tetradecyloxy)-phenyl]methyl]amino]phenyl]methyl]thiazolium bromide 3-[[4-[[(methylamino)carbonyl][[4-(tetradecyloxy)-phenyl]methyl]amino]phenyl]methyl]-5-methyl-thiazolium bromide 3-[[4-[[(methylamino)carbonyl][[3-(tetradecyloxy)-phenyl]methyl]amino]phenyl]methyl]thiazolium bromide 3-[[4-[[(methylamino)carbonyl][[3-(tetradecyloxy)-phenyl]methyl]amino]phenyl]methyl]-5-methyl-thiazolium bromide 3-[[4-[[(methylamino)carbonyl][[3-(dodecyloxy)-phenyl]methyl]amino]phenyl]methyl]thiazolium bromide 3-[[4-[[(methylamino)carbonyl][[3-(dodecyloxy)-phenyl]methyl]amino]phenyl]methyl]-5-methyl-thiazolium bromide 3-[[4-[[(methylamino)carbonyl][[3-chloro-4-(tetradecyloxy)phenyl]methyl]amino]phenyl]methyl]-thiazolium bromide 3-[[4-[[(methylamino)carbonyl][[3-methoxy-4-(tetradecyloxy)phenyl]methyl]amino]phenyl]methyl]-5-methyl-thiazolium bromide 3-[[4-[[(methylamino)carbonyl][[4-chloro-3-(tetradecyloxy)phenyl]methyl]amino]phenyl]methyl]-thiazolium bromide 3-[[4-[[(methylamino)carbonyl][[4-chloro-3-(tetradecyloxy)phenyl]methyl]amino]phenyl]methyl]-5-methyl-thiazolium bromide 3-[[4-[[(methylamino)carbonyl][[4-t-butyl-3-(tetradecyloxy)phenyl]methyl]amino]phenyl]methyl]-thiazolium bromide 3-[[4-[[(methylamino)carbonyl][[4-t-butyl-3-(tetradecyloxy)phenyl]methyl]amino]phenyl]methyl]-5-methyl-thiazolium bromide 3-[[4-[[(methylamino)carbonyl][[4-methoxy-3-(tetradecyloxy)phenyl]methyl]amino]phenyl]methyl]-thiazolium bromide 3-[[4-[[(methylamino)carbonyl][[4-methoxy-3-(tetradecyloxy)phenyl]methyl]amino]phenyl]methyl]-5-methyl-thiazolium bromide 3-[[3-[[(methylamino)carbonyl][[4-(tetradecyloxy)-phenyl]methyl]amino]phenyl]methyl]thiazolium bromide 3-[[3-[[(methylamino)carbonyl][[4-(tetradecyloxy)-phenyl]methyl]amino]phenyl]methyl]-5-methyl-thiazolium bromide 3-[[3-[[(methylamino)carbonyl][[3-(tetradecyloxy)-phenyl]methyl]amino]phenyl]methyl]thiazolium bromide 3-[[3-[[(methylamino)carbonyl][[3-t-butyl-4-(tetradecyloxy)phenyl]methyl]amino]phenyl]methyl]-5-methyl-thiazolium bromide 3-[[3-[[(methylamino)carbonyl][[3-methoxy-4-(tetradecyloxy)phenyl]methyl]amino]phenyl]methyl]-thiazolium bromide 3-[[3-[[(methylamino)carbonyl][[3-methoxy-4-(tetradecyloxy)phenyl]methyl]amino]phenyl]methyl]-5-methyl-thiazolium bromide 3-[[3-[[(methylamino)carbonyl][[4-chloro-3-(tetradecyloxy)phenyl]methyl]amino]phenyl]methyl]-thiazolium bromide 3-[[3-[[(methylamino)carbonyl][[4-chloro-3-(tetradecyloxy)phenyl]methyl]amino]phenyl]methyl]-5-methyl-thiazolium bromide 3-[[3-[[(methylamino)carbonyl][[4-t-butyl-3-(tetradecyloxy)phenyl]methyl]amino]phenyl]methyl]-thiazolium bromide 3-[[3-[[(methylamino)carbonyl][[4-t-butyl-3-(tetradecyloxy)phenyl]methyl]amino]phenyl]methyl]-5-methyl-thiazolium bromide 3-[[3-[[(methylamino)carbonyl][[4-methoxy-3-(tetradecyloxy)phenyl]methyl]amino]phenyl]methyl]-thiazolium bromide 3-[[3-[[(methylamino)carbonyl][[4-methoxy-3-(tetradecyloxy)phenyl]methyl]amino]phenyl]methyl]-5-methyl-thiazolium bromide

EXAMPLE 64

1-[[3-[Acetyl[[4-(tetradecyloxy)phenyl]methyl]amino]phenyl]methyl]-3,4-dimethylpyridinium bromide A mixture of 1.6 g of N-[3-(bromomethyl)phenyl]-N-[[4-(tetradecyloxy)phenyl]methyl]acetamide and 1.29 g of 3,4-lutidine in 25 ml of acetonitrile is refluxed under argon for 5 hours. The solvent is evaporated and the residue stirred with ether. The solid is collected by centrifugation, washed several times with ether and vacuum dried to give the desired product as a solid, m.p. 100°–103° C.

EXAMPLE 65

1-[[4-[Acetyl[[4-(tetradecyloxy)phenyl]methyl]amino]phenyl]methyl]-3,4-dimethylpyridinium bromide A mixture of 1.5 g of N-[4-(bromomethyl)phenyl]-N-[[4-(tetradecyloxy)phenyl]methyl]acetamide and 908.82 mg of 3,4-lutidine in 25 ml of acetonitrile is refluxed for 5 hours. The solvent is evaporated, the residue stirred with ether and the solid collected by centrifugation. The solid is washed with ether and vacuum dried to give 1.3 g of the desired product as a gummy solid, m.p. 124°–127° C.

EXAMPLE 66

3,5-Dimethyl-1-[[3-[[[4-(tetradecyloxy)phenyl]acetyl]amino]phenyl]methyl]pyridinium bromide A mixture of 1.5 g of N-[3-(bromomethyl)phenyl]-4-(tetradecyloxy)benzeneacetamide and 933.5 mg of 3,5-lutidine is refluxed in 25 ml of acetonitrile for 4 hours under argon. The solvent is evaporated and the residue stirred with ether and collected by centrifugation. The solid is washed several times with ether and vacuum dried to give 1.6 g of the desired product as a white powder, m.p. 122°–125° C.

EXAMPLE 67

3,4-Dimethyl-1-[[3-[[[4-(tetradecyloxy)phenyl]acetyl]amino]phenyl]methyl]pyridinium bromide A mixture of 1.5 g of N-[3-(bromomethyl)phenyl]-4-(tetradecyloxy)benzeneacetamide and 933.5 mg of 3,4-lutidine in 25 ml of acetonitrile is refluxed under argon for 4 hours. The solvent is evaporated and the residue mixed with ether. The solid is collected via centrifugation, washed with ether several times and vacuum dried to give 1.5 g of the desired product as a gray-white powder, m.p. 125°–128° C.

EXAMPLE 68

2-[[3-[[[4-(Tetradecyloxy)phenyl]acetyl]amino]phenyl]methyl]imidazo[1,5-a]pyridinium bromide A mixture of 1.5 g of N-[3-(bromomethyl)phenyl]-4-(tetradecyloxy)benzeneacetamide and 1.03 g of imidazo[1,2-a]pyridine in 25 ml of acetonitrile is refluxed under argon for 3.5 hours. The solvent is evaporated and the residue stirred with ether and collected by centrifugation. The solid is washed several times with ether and vacuum dried to give 1.5 g of the desired product as a white powder, m.p 133°–135° C.

According to the methods outlined hereinabove in Flowsheet A and described in detail in Examples 66–68, the compounds of this invention listed hereinbelow in List 7 can be prepared. These methods are applicable to the preparation of the compounds of this invention by one skilled in the art.

List 7

2-[[2-[[[-4-(tetradecyloxy)phenyl]acetyl]amino]phenyl]methyl]imidazo[1,5-a]pyridinium bromide 2-[[2-[[[-3-(tetradecyloxy)phenyl]acetyl]amino]phenyl]methyl]imidazo[1,5-a]pyridinium bromide 2-[[2-[[[-2-(tetradecyloxy)phenyl]acetyl]amino]phenyl]methyl]imidazo[1,5-a]pyridinium bromide 2-[[2-[[[3-chloro-4-(hexadecyloxy)phenyl]acetyl]amino]phenyl]methyl]imidazo[1,5-a]pyridinium bromide 2-[[2-[[[3-acetyl-4-(tetradecyloxy)phenyl]acetyl]amino]phenyl]methyl]imidazo[1,5-a]pyridinium bromide 2-[[2-[[[3-acetyl-2-(tetradecyloxy)phenyl]acetyl]amino]phenyl]methyl]imidazo[1,5-a]pyridinium bromide 2-[[2-[[[3-t-butyl-2-(tetradecyloxy)phenyl]acetyl]amino]phenyl]methyl]imidazo[1,5-a]pyridinium bromide 2-[[2-[[[3-methoxy-4-(tetradecyloxy)phenyl]acetyl]amino]phenyl]methyl]imidazo[1,5-a]pyridinium bromide 2-[[2-[[[2-chloro-4-(tetradecyloxy)phenyl]acetyl]amino]phenyl]methyl]imidazo[1,5-a]pyridinium bromide 2-[[2-[[[4-chloro-3-(tetradecyloxy)phenyl]acetyl]amino]phenyl]methyl]imidazo[1,5-a]pyridinium bromide 2-[[2-[[[4-t-butyl-2-(tetradecyloxy)phenyl]acetyl]amino]phenyl]methyl]imidazo[1,5-a]pyridinium bromide 2-[[2-[[[4-methoxy-3-(tetradecyloxy)phenyl]acetyl]amino]phenyl]methyl]imidazo[1,5-a]pyridinium bromide 2-[[2-[[[4-methoxy-2-(tetradecyloxy)phenyl]acetyl]amino]phenyl]methyl]imidazo[1,5-a]pyridinium bromide 2-[[2-[[[-4-(tetradecyloxy)phenyl]acetyl]amino]phenyl]methyl]imidazo[1,5-a]pyridinium bromide 2-[[2-[[[-3-(tetradecyloxy)phenyl]acetyl]amino]phenyl]methyl]imidazo[1,5-a]pyridinium bromide 2-[[2-[[[3-chloro-2-(tetradecyloxy)phenyl]acetyl]amino]phenyl]methyl]imidazo[1,5-a]pyridinium bromide 2-[[2-[[[3-fluoro-4-(tetradecyloxy)phenyl]acetyl]amino]phenyl]methyl]imidazo[1,5-a]pyridinium bromide 2-[[2-[[[3-fluoro-2-(tetradecyloxy)phenyl]acetyl]amino]phenyl]methyl]imidazo[1,5-a]pyridinium bromide 2-[[2-[[[3-acetyl-4-(tetradecyloxy)phenyl]acetyl]amino]phenyl]methyl]imidazo[1,5-a]pyridinium bromide 2-[[2-[[[3-acetyl-2-(tetradecyloxy)phenyl]acetyl]amino]phenyl]methyl]imidazo[1,5-a]pyridinium bromide 2-[[2-[[[3-t-butyl-4-(tetradecyloxy)phenyl]acetyl]amino]Phenyl]methyl]imidazo[1,5-a]pyridinium bromide 2-[[2-[[[3-t-butyl-2-(tetradecyloxy)phenyl]acetyl]amino]phenyl]methyl]imidazo[1,5-a]pyridinium bromide
2-[[2-[[[3-methoxy-4-(tetradecyloxy)phenyl]acetyl]amino]phenyl]methyl]imidazo[1,5-a]pyridinium bromide
2-[[2-[[[3-methoxy-2-(tetradecyloxy)phenyl]acetyl]amino]phenyl]methyl]imidazo[1,5-a]pyridinium bromide
2-[[2-[[[2-chloro-4-(tetradecyloxy)phenyl]acetyl]amino]phenyl]methyl]imidazo[1,5-a]pyridinium bromide
2-[[2-[[[4-t-butyl-3-(tetradecyloxy)phenyl]acetyl]amino]phenyl]methyl]imidazo[1,5-a]pyridinium bromide
2-[[2-[[[4-t-butyl-2-(tetradecyloxy)phenyl]acetyl]amino]phenyl]methyl]imidazo[1,5-a]pyridinium bromide
2-[[2-[[[4-methoxy-3-(tetradecyloxy)phenyl]acetyl]amino]phenyl]methyl]imidazo[1,5-a]pyridinium bromide
2-[[4-[[[-4-(hexadecyloxy)phenyl]acetyl]amino]phenyl]methyl]imidazo[1,5-a]pyridinium bromide
2-[[4-[[[-4-(hexadecyloxy)phenyl]acetyl]amino]phenyl]methyl]imidazo[1,5-a]pyridinium bromide
1-[[2-[[[-4-(tetradecyloxy)phenyl]acetyl]amino]phenyl]methyl]pyridinium bromide
1-[[2-[[[-3-(tetradecyloxy)phenyl]acetyl]amino]phenyl]methyl]pyridinium bromide
1-[[2-[[[-2-(tetradecyloxy)phenyl]acetyl]amino]phenyl]methyl]pyridinium bromide
1-[[2-[[[3-chloro-4-(tetradecyloxy)phenyl]acetyl]amino]phenyl]methyl]pyridinium bromide
1-[[2-[[[3-fluoro-2-(tetradecyloxy)phenyl]acetyl]amino]phenyl]methyl]pyridinium bromide
1-[[2-[[[3-acetyl-4-(tetradecyloxy)phenyl]acetyl]amino]phenyl]methyl]pyridinium bromide
1-[[2-[[[3-acetyl-2-(tetradecyloxy)phenyl]acetyl]amino]phenyl]methyl]pyridinium bromide
1-[[2-[[[3-t-butyl-4-(tetradecyloxy)phenyl]acetyl]amino]phenyl]methyl]pyridinium bromide
1-[[2-[[[3-t-butyl-2-(tetradecyloxy)phenyl]acetyl]amino]phenyl]methyl]pyridinium bromide
1-[[2-[[[3-methoxy-4-(tetradecyloxy)phenyl]acetyl]amino]phenyl]methyl]pyridinium bromide
1-[[2-[[[3-methoxy-2-(tetradecyloxy)phenyl]acetyl]amino]phenyl]methyl]pyridinium bromide
1-[[2-[[[2-chloro-4-(tetradecyloxy)phenyl]acetyl]amino]phenyl]methyl]Pyridinium bromide
1-[[2-[[[4-chloro-3-(tetradecyloxy)phenyl]acetyl]amino)phenyl]methyl]pyridinium bromide
1-[[2-[[[4-t-butyl-2-(tetradecyloxy)phenyl]acetyl]amino]phenyl]methyl]pyridinium bromide
1-[[2-[[[4-methoxy-3-(tetradecyloxy)phenyl]acetyl]amino]phenyl]methyl]pyridinium bromide
1-[[2-[[[4-methoxy-2-(tetradecyloxy)phenyl]acetyl]amino]phenyl]methyl]pyridinium bromide
1-[[1-[[[-4-(tetradecyloxy)phenyl]acetyl]amino]phenyl]methyl]pyridinium bromide
1-[[1-[[[-3 -(tetradecyloxy)phenyl]acetyl]amino]phenyl]methyl]pyridinium bromide
1-[[1-[[[3-chloro-2-(tetradecyloxy)phenyl]acetyl]amino]phenyl]methyl]pyridinium bromide
1-[[1-[[[3-fluoro-4-(tetradecyloxy)phenyl]acetyl]amino]phenyl]methyl]pyridinium bromide
1-[[1-[[[3-fluoro-2-(tetradecyloxy)phenyl]acetyl]amino]phenyl]methyl]pyridinium bromide
1-[[1-[[[3-acetyl-4-(tetradecyloxy)phenyl]acetyl]amino]phenyl]methyl]pyridinium bromide
1-[[1-[[[3-acetyl-2-(tetradecyloxy)phenyl]acetyl]amino]phenyl]methyl]pyridinium bromide
1-[[1-[[[3-t-butyl-4-(tetradecyloxy)phenyl]acetyl]amino]phenyl]methyl]pyridinium bromide
1-[[4-[[[3-fluoro-2-(hexadecyloxy)phenyl]acetyl]amino]phenyl]methyl]pyridinium bromide
1-[[4-[[[3-acetyl-4-(tetradecyloxy)phenyl]acetyl]amino]phenyl]methyl]pyridinium bromide
1-[[4-[[[3-acetyl-4-(hexadecyloxy)phenyl]acetyl]amino]phenyl]methyl]pyridinium bromide
1-[[4-[[[3-acetyl-2-(tetradecyloxy)phenyl]acetyl]amino]phenyl]methyl]pyridinium bromide
1-[[4-[[[3-acetyl-2-(hexadecyloxy)phenyl]acetyl]amino]phenyl]methyl]pyridinium bromide
1-[[4-[[[3-t-butyl-4-(tetradecyloxy)phenyl]acetyl]amino]phenyl]methyl]pyridinium bromide
1-[[4-[[[3-t-butyl-4-(hexadecyloxy)phenyl]acetyl]amino]phenyl]methyl]pyridinium bromide
1-[[4-[[[3-t-butyl-2-(tetradecyloxy)phenyl]acetyl]amino]phenyl]methyl]pyridinium bromide
1-[[4-[[[3-methoxy-4-(hexadecyloxy)phenyl]acetyl]amino]phenyl]methyl]pyridinium bromide
1-[[4-[[[3-methoxy-2-(tetradecyloxy)phenyl]acetyl]amino]phenyl]methyl]pyridinium bromide
1-[[4-[[[3-methoxy-2-(hexadecyloxy)phenyl]acetyl]amino]phenyl]methyl]pyridinium bromide
1-[[4-[[[2-chloro-4-(tetradecyloxy)phenyl]acetyl]amino]phenyl]methyl]pyridinium bromide
1-[[4-[[[2-chloro-4-(hexadecyloxy)phenyl]acetyl]amino]phenyl]methyl]pyridinium bromide
1-[[4-[[[4-chloro-3-(tetradecyloxy)phenyl]acetyl]amino]phenyl]methyl]pyridinium bromide
1-[[4-[[[4-chloro-3-(hexadecyloxy)phenyl]acetyl]amino]phenyl]methyl]pyridinium bromide
1-[[4-[[[4-chloro-2-(tetradecyloxy)phenyl]acetyl]amino]phenyl]methyl]pyridinium bromide
1-[[4-[[[4-t-butyl-3-(tetradecyloxy)phenyl]acetyl]amino]phenyl]methyl]pyridinium bromide
1-[[4-[[[4-t-butyl-3-(hexadecyloxy)phenyl]acetyl]amino]phenyl]methyl]pyridinium bromide
1-[[4-[[[4-t-butyl-2-(tetradecyloxy)phenyl]acetyl]amino]phenyl]methyl]pyridinium bromide
1-[[4-[[[4-t-butyl-2-(hexadecyloxy)phenyl]acetyl]amino]phenyl]methyl]pyridinium bromide
1-[[4-[[[4-methoxy-3-(tetradecyloxy)phenyl]acetyl]amino]phenyl]methyl]pyridinium bromide
1-[[4-[[[4-methoxy-3-(hexadecyloxy)phenyl]acetyl]amino]phenyl]methyl]pyridinium bromide
3,4-Dimethyl-1-[[2-[[[-4-(tetradecyloxy)phenyl]acetyl]amino]phenyl]methyl]pyridinium bromide
3,4-Dimethyl-1-[[2-[[[-3-(tetradecyloxy)phenyl]acetyl]amino]phenyl]methyl]pyridinium bromide
3,4-Dimethyl-1-[[2-[[[-2-(hexadecyloxy)phenyl]acetyl]amino]phenyl]methyl]pyridinium bromide
3,4-Dimethyl-1-[[2-[[[3-chloro-4-(tetradecyloxy)phenyl]acetyl]amino]phenyl]methyl]pyridinium bromide
3,4-Dimethyl-1-[[2-[[[3-fluoro-2-(tetradecyloxy)phenyl]acetyl]amino]phenyl]methyl]pyridinium bromide
3,4-Dimethyl-1-[[2-[[[3-acetyl-4-(tetradecyloxy)phenyl]acetyl]amino]phenyl]methyl]pyridinium bromide
3,4-Dimethyl-1-[[2-[[[3-acetyl-2-(tetradecyloxy)phenyl]acetyl) amino) phenyl]methyl]pyridinium bromide
3,4-Dimethyl-1-[[2-[[[3-t-butyl-4-(tetradecyloxy)phenyl]acetyl]amino]phenyl]methyl]pyridinium bromide 3,4-Dimethyl-1-[[2-[[[3-t-butyl-2-(tetradecyloxy)-phenyl]acetyl]amino]phenyl]methyl]pyridinium bromide 3,4-Dimethyl-1-[[2-[[[3-methoxy-4-(tetradecyloxy)-phenyl]acetyl)amino]phenyl]methyl)pyridinium bromide 3,4-Dimethyl-1-[[2-[[[3-methoxy-2-(tetradecyloxy)-phenyl]acetyl]amino]Phenyl]methyl]pyridinium bromide 3,4-Dimethyl-1-[[2-[[[2-chloro-4-(tetradecyloxy)-phenyl]acetyl]amino]phenyl]methyl]pyridinium bromide 3,4-Dimethyl-1-[[3,4-Dimethyl-1-[[[3-acetyl-4-(tetradecyloxy)phenyl]acetyl]amino]phenyl]methyl]-pyridinium bromide 3,4-Dimethyl-1-[[3,4-Dimethyl-1-[[[3-acetyl-2-(tetradecyloxy)phenyl]acetyl]amino]Phenyl]methyl]-pyridinium bromide 3,4-Dimethyl-1-[[3,4-Dimethyl-1-[[[3-t-butyl-4-(tetradecyloxy)phenyl]acetyl]amino]phenyl]methyl]-pyridinium bromide 3,4-Dimethyl-1-[[4-[[[3-fluoro-2-(tetradecyloxy)]-phenyl]acetyl]amino]Phenyl]methyl]Pyridinium bromide 3,4-Dimethyl-1-[[4-[[[3-acetyl-4-(tetradecyloxy)phenyl]acetyl]amino]Phenyl]methyl]pyridinium bromide 3,4-Dimethyl-1-[[4-[[[3-acetyl-4-(hexadecyloxy)phenyl]acetyl]amino]Phenyl]methyl]Pyridinium bromide 3,5-Dimethyl-1-[[2-[[[-4-(tetradecyloxy)phenyl]acetyl]amino]Phenyl]methyl]Pyridinium bromide 3,5-Dimethyl-1-[[2-[[[-3-(tetradecyloxy)phenyl]acetyl]amino]Phenyl]methyl]Pyridinium bromide 3,5-Dimethyl-1-[[2-[[[-2-(dodecyloxy)phenyl]acetyl]amino]Phenyl)methyl]Pyridinium bromide 3,5-Dimethyl-1-[[2-[[[3-chloro-4-(tetradecyloxy)-phenyl]acetyl]amino]Phenyl]methyl)Pyridinium bromide 3,5-Dimethyl-1-[[2-[[[3-fluoro-2-(tetradecyloxy)phenyl]acetyl]amino]phenyl]methyl]Pyridinium bromide 3,5-Dimethyl-1-[[2-[[[3-acetyl-4-(tetradecyloxy)phenyl]acetyl]amino]phenyl]methyl]pyridinium bromide 3,5-Dimethyl-1-[[2-[[[3-acetyl-2-(tetradecyloxy)phenyl]acetyl)amino]phenyl]methyl]Pyridinium bromide 3,5-Dimethyl-1-[(2-[[[3-t-butyl-4-(tetradecyloxy)-phenyl)acetyl]amino]phenyl]methyl]Pyridinium bromide 3,5-Dimethyl-1-[[2    -[[[3-t-butyl-2-(tetradecyloxy)-phenyl]acetyl]amino]phenyl]methyl]pyridinium bromide 3,5-Dimethyl-1-[[2-[[[3-methoxy-4-(tetradecyloxy)-phenyl]acetyl]amino]phenyl]methyl]pyridinium bromide 3,5-Dimethyl-1-[[2-[[[3-methoxy-2-(tetradecyloxy)-phenyl]acetyl]amino]phenyl]methyl]pyridinium bromide 3,5-Dimethyl-1-[[2-[[[2-chloro-4-(tetradecyloxy)-phenyl]acetyl]amino]phenyl]methyl]pyridinium bromide 3,5-Dimethyl-1-[[4-[[[2-chloro-4-(tetradecyloxy)-phenyl]acetyl]amino]phenyl]methyl]pyridinium bromide 3,5-Dimethyl-1-[[4-[[[2-chloro-4-(hexadecyloxy)-phenyl]acetyl]amino]phenyl]methyl]pyridinium bromide

EXAMPLE 69

2-(Trimethylstannyl)thiazole

To 99.99 ml of n-butyl lithium in hexane, dissolved in 200 ml of ether is added dropwise with stirring over 1 hour, at −78° C., a solution of 16 g of thiazole in 100 ml of ether over 1 hour. A solution of 49.81 g of trimethyltin chloride in 100 ml of ether is added dropwise over 20 minutes followed by additional stirring for 1 hour. The reaction mixture is poured into saturated sodium bicarbonate and the organic layer separated, dried and evaporated to a residue. The residue is vacuum distilled to give 33.4 g of the desired product as a colorless liquid, B.P. 60°–65° C./0.7 mm.

EXAMPLE 70

N-[2-[4-(Tetradecyloxy)phenyl]ethyl]-N-[3-(2-thiazolylmethyl)phenyl]acetamide

A mixture of 1.3 g of N-[3-(bromomethyl)phenyl-N-[2-[4-(tetradecyloxy)phenyl]ethyl]acetamide, 787.04 mg of 2-(trimethylstannyl)thiazole and 83.77 mg of PdCl$_2$(PO$_3$)$_2$ in 30 ml of tetrahydrofuran is stirred at reflux for 14 hours. The mixture is diluted with ether and filtered through a pad of silica gel. The filtrate is washed with 1N sodium hydroxide, dried and filtered through a pad of alumina. The solvent is evaporated and the residue chromatographed on silica gel using 1:1 ethyl acetate:hexane to give 0.7 g of the desired product as an oil which crystallized to an off-white solid, m.p. 46°–50° C.

EXAMPLE 71

N-[2-[4-(Tetradecyloxy)phenyl]ethyl]-N-[3-(2-thiazolylmethyl)phenyl]acetamide monohydrochloride To a solution of 300 mg of N-[2-[4-(tetradecyloxy)-phenyl]ethyl]-N-[3-(2-thiazolylmethyl)phenyl]acetamide in 3 ml of ether is added 10 ml of ether saturated with hydrogen chloride. The resulting solid is collected by centrifugation, washed several times with ether and vacuum dried to give 200 mg of the desired product, m.p. 114°–118° C.

EXAMPLE 72

3-Methyl-2-[[3-[acetyl[2-[4-(tetradecyloxy)phenyl]ethyl]amino]phenyl]methyl]thiazolium iodide A mixture of 300 mg of N-[2-[4-(tetradecyloxy)-phenyl]ethyl]-N-[3-(2-thiazolylmethyl)phenyl]acetamide and 1.4 g of methyl iodide in 5 ml of toluene is heated at 140° C. in a closed vessel for 4.5 hours then cooled. Ether is added, the solid collected by centrifugation and then washed several times with ether. The solid is vacuum dried to give 235 mg of the desired product as a tan solid, m.p. 130°–134° C.

EXAMPLE 73

N-(3-Iodophenyl)-4-(tetradecyloxy)benzeneacetamide

To a solution of 14.29 g of m-iodoaniline and 15.52 g of pyridine in 150 ml of tetrahydrofuran is added at room temperature over 20 minutes a solution of p-tetradecyloxyphenylacetyl chloride in 150 ml of tetrahydrofuran. The mixture is stirred overnight and the solvent removed. The residue is partitioned between dilute hydrochloric acid and warm chloroform. The separated organic layer is washed with dilute hydrochloric acid, dried and evaporated to a residue which is crystallized from carbon tetrachloride:hexane to give 25.0 g of the desired product as a pink solid, m.p. 108°–110° C.

EXAMPLE 74

4-(Tetradecyloxy)-N-[3-(2-thiazolyl)phenyl]benzeneacetamide

A mixture of 10 g of N-[3-iodophenyl)-4-(tetradecyloxy)benzeneacetamide, 4.96 g of 2-(trimethylstannyl)thiazole, and 638.62 mg of dichlorobis(triphenylphosphine)palladium (II) in 100 ml of tetrahydrofuran is refluxed under argon for 6 hours. The solvent is evaporated and the residue is partitioned between chloroform and 1N sodium hydroxide. The organic layer is dried and evaporated to a yellow solid residue. The residue is purified by chromatography on silica gel using chloroform. A total of 3.5 g of starting material is recovered as well as impure product which is crystallized from hexane:carbon tetrachloride to give 1.8 g of the desired product as a tan solid, m.p. 128°–131° C.

EXAMPLE 75

3-Methyl-2-[3-[[[4-(tetradecyloxy)phenyl]acetyl]amino]phenyl]thiazolium chloride A mixture of 1.4 g of 4-(tetradecyloxy)-N-[3-(2-thiazolyl)phenyl]benzeneacetamide and 11.76 g of methyl iodide in 15 ml of acetonitrile is heated at 100° C. in a closed glass vessel for 6 hours. The solvent is evaporated and the residue dissolved in methyl alcohol and stirred with 12 g of chloride ion exchange resin, then filtered. The solvent is removed and the residue dissolved in a minimum of methylene chloride and ether added. The resulting solid is collected by centrifugation, washed several times with ether and vacuum dried to give 1.2 g of the desired product as an off white solid, m.p. 165°–168° C.

According to the methods outlined hereinabove in Flowsheet B and described in detail in Examples 73–75, the compounds of this invention listed hereinbelow in List 8 can be prepared. These methods are applicable to the preparation of the compounds of this invention by one skilled in the art.

List 8

3-Methyl-2-[2-[[[-4-(tetradecyloxy)phenyl]acetyl]amino]phenyl]thiazolium chloride
3-Methyl-2-[2-[[[-3-(tetradecyloxy)phenyl)acetyl]amino]phenyl]thiazolium chloride
3-Methyl-2-[2-[[[-2-(tetradecyloxy)phenyl]acetyl]amino]phenyl]thiazolium chloride
3-Methyl-2-[2-[[[3-chloro-4-(tetradecyloxy)phenyl]acetyl]amino]phenyl]thiazolium chloride
3-Methyl-2-[2-[[[3-chloro-2-(tetradecyloxy)phenyl]acetyl)amino]phenyl]thiazolium chloride
3-Methyl-2-[2-[[[3-fluoro-4-(tetradecyloxy)phenyl]acetyl]amino]phenyl]thiazolium chloride
3-Methyl-2-[2-[[[3-fluoro-2-(tetradecyloxy)phenyl]acetyl]amino)phenyl]thiazolium chloride
3-Methyl-2-[2-[[[3-acetyl-2-(tetradecyloxy)phenyl]acetyl]amino]Phenyl]thiazolium chloride
3-Methyl-2-[2-[[[3-t-butyl-4-(tetradecyloxy)phenyl]acetyl]amino]phenyl]thiazolium chloride
3-Methyl-2-[2-[[[3-t-butyl-2-(tetradecyloxy)phenyl]acetyl]amino]phenyl]thiazolium chloride
3-Methyl-2-[2-[[[3-methoxy-4-(tetradecyloxy)phenyl]acetyl]amino]phenyl]thiazolium chloride
3-Methyl-2-[2-[[[3-methoxy-2-(tetradecyloxy)phenyl]acetyl]amino]phenyl]thiazolium chloride
3-Methyl-2-[2-[[[2-chloro-4-(tetradecyloxy)Phenyl]acetyl]amino]phenyl]thiazolium chloride
3-Methyl-2-[2-[[[4-chloro-3-(tetradecyloxy)Phenyl]acetyl]amino]phenyl]thiazolium chloride
3-Methyl-2-[2-[[[4-t-butyl-2-(tetradecyloxy)phenyl]acetyl]amino]phenyl]thiazolium chloride
3-Methyl-2-[3-[[[3-chloro-2-(tetradecyloxy)phenyl]acetyl]amino]phenyl]thiazolium chloride
3-Methyl-2-[3-[[[3-chloro-2-(dodecyloxy)phenyl]acetyl]amino]phenyl]thiazolium chloride
3-Methyl-2-[3-[[[3-fluoro-4-(tetradecyloxy)phenyl]acetyl]amino]phenyl]thiazolium chloride
3-Methyl-2-[3-[[[4-(hexadecyloxy)phenyl]acetyl]amino]phenyl]thiazolium chloride
3-Methyl-2-[3-[[[3-fluoro-2-(tetradecyloxy)phenyl]acetyl]amino]phenyl]thiazolium chloride
3-Methyl-2-[3-[[[3-fluoro-2-(dodecyloxy)phenyl]acetyl]amino]phenyl]thiazolium chloride
3-Methyl-2-[3-[[[3-acetyl-4-(tetradecyloxy)phenyl]acetyl]amino]phenyl]thiazolium chloride
3-Methyl-2-[3-[[[3-acetyl-4-(dodecyloxy)phenyl]acetyl]amino]phenyl]thiazolium chloride
3-Methyl-2-[3-[[[3-acetyl-2-(tetradecyloxy)phenyl]acetyl]amino]phenyl]thiazolium chloride
3-Methyl-2-[3-[[[3-t-butyl-4-(dodecyloxy)phenyl]acetyl]amino]phenyl]thiazolium chloride
3-Methyl-2-[3-[[[2-chloro-4-(tetradecyloxy)phenyl]acetyl]amino]phenyl]thiazolium chloride
3-Methyl-2-[3-[[[4-chloro-3-(dodecyloxy)phenyl]acetyl]amino]phenyl]thiazolium chloride
3-Methyl-2-[3-[[[4-chloro-2-(tetradecyloxy)phenyl]acetyl]amino]phenyl]thiazolium chloride
3-Methyl-2-[3-[[[4-chloro-2-(dodecyloxy)phenyl]acetyl]amino]phenyl]thiazolium chloride
3-Methyl-2-[3-[[[4-t-butyl-3-(decyloxy)phenyl]acetyl]amino]phenyl]thiazolium chloride
3-Methyl-2-[3-[[[4-methoxy-3-(dodecyloxy)phenyl]acetyl]amino]phenyl]thiazolium chloride
3-Methyl-2-[3-[[[4-methoxy-2-(tetradecyloxy)phenyl]acetyl]amino]phenyl]thiazolium chloride
3-Methyl-2-[3-[[[4-methoxy-2-(dodecyloxy)phenyl]acetyl]amino]5-Methylthiazolium chloride
3-Methyl-2-[4-[[[-4-(tetradecyloxy)phenyl]acetyl]amino]phenyl]thiazolium chloride
3-Methyl-2-[4-[[[-3-(tetradecyloxy)phenyl]acetyl]amino]phenyl]thiazolium chloride
3-Methyl-2-[4-[[[-2-(tetradecyloxy)phenyl]acetyl]amino]phenyl]thiazolium chloride
3-Methyl-2-[4-[[[3-acetyl-4-(tetradecyloxy)phenyl]acetyl]amino]phenyl]thiazolium chloride
3-Methyl-2-[4-[[[3-acetyl-2-(tetradecyloxy)phenyl]acetyl]amino]phenyl]thiazolium chloride
3-Methyl-2-[4-[[[3-t-butyl-4-(tetradecyloxy)phenyl]acetyl]amino]phenyl]thiazolium chloride
3-Methyl-2-[4-[[[3-t-butyl-2-(tetradecyloxy)phenyl]acetyl]amino]phenyl]thiazolium chloride
3-Methyl-2-[4-[[[3-methoxy-4-(tetradecyloxy)phenyl]acetyl]amino]phenyl]thiazolium chloride
3-Methyl-2-[4-[[[3-methoxy-2-(tetradecyloxy)phenyl]acetyl]amino]phenyl]thiazolium chloride
3-Methyl-2-[4-[[[2-chloro-4-(tetradecyloxy)phenyl]acetyl]amino]phenyl]thiazolium chloride
3-Methyl-2-[4-[[[4-chloro-3-(tetradecyloxy)phenyl]acetyl]amino]phenyl]thiazolium chloride
3-Methyl-2-[4-[[[4-chloro-2-(tetradecyloxy)phenyl]acetyl]amino]phenyl]thiazolium chloride 3-Methyl-2-[4-[[[4-t-butyl-3-(tetradecyloxy)phenyl]acetyl]amino]phenyl]thiazolium chloride
3-Methyl-2-[4-[[[4-t-butyl-2-(tetradecyloxy)phenyl]acetyl]amino]phenyl]thiazolium chloride
3-Methyl-2-[4-[[[4-methoxy-3-(tetradecyloxy)phenyl]acetyl]amino]phenyl]thiazolium chloride
3-Methyl-2-[4-[[[4-methoxy-2-(tetradecyloxy)phenyl]acetyl]amino]phenyl]thiazolium chloride
3-ethyl-2-[2-[[[-4-(tetradecyloxy)phenyl]acetyl]amino]phenyl]thiazolium chloride
3-ethyl-2-[2-[[[-3-(tetradecyloxy)phenyl]acetyl]amino]phenyl]thiazolium chloride
3-ethyl-2-[2-[[[-2-(tetradecyloxy)phenyl]acetyl]amino]phenyl]thiazolium chloride
3-ethyl-2-[2-[[[3-chloro-4-(tetradecyloxy)phenyl]acetyl]amino]phenyl]thiazolium chloride
3-ethyl-2-[2-[[[3-chloro-2-(tetradecyloxy)phenyl]acetyl]amino]phenyl]thiazolium chloride
3-ethyl-2-[2-[[[3-fluoro-4-(tetradecyloxy)phenyl]acetyl]amino]phenyl]thiazolium chloride
3-ethyl-2-[2-[[[3-fluoro-2-(tetradecyloxy)phenyl]acetyl]amino]phenyl]thiazolium chloride
3-ethyl-2-[2-[[[3-acetyl-4-(tetradecyloxy)phenyl]acetyl]amino]phenyl]thiazolium chloride
3-ethyl-2-[2-[[[3-acetyl-2-(tetradecyloxy)phenyl]acetyl]amino]phenyl]thiazolium chloride
3-ethyl-2-[2-[[[3-t-butyl-4-(tetradecyloxy)phenyl]acetyl]amino]phenyl]thiazolium chloride
3-ethyl-2-[3-[[[-2-(tetradecyloxy)phenyl]acetyl]amino]phenyl]thiazolium chloride
3-ethyl-2-[3-[[[3-chloro-4-(octyloxy)phenyl]acetyl]amino]phenyl]thiazolium chloride
3-ethyl-2-[3-[[[3-chloro-2-(tetradecyloxy)Phenyl]acetyl]amino]phenyl]thiazolium chloride
3-ethyl-2-[3-[[[3-fluoro-4-(tetradecyloxy)phenyl]acetyl]amino]phenyl]thiazolium chloride
3-ethyl-2-[3-[[[3-fluoro-2-(tetradecyloxy)phenyl]acetyl]amino]phenyl]thiazolium chloride
3-ethyl-2-[3-[[[3-acetyl-4-(tetradecyloxy)phenyl]acetyl]amino]phenyl]thiazolium chloride
3-ethyl-2-[3-[[[3-acetyl-2-(tetradecyloxy)phenyl]acetyl]amino]phenyl]thiazolium chloride
3-ethyl-2-[3-[[[3-t-butyl-4-(decyloxy)phenyl]acetyl]amino]phenyl]thiazolium chloride
3-ethyl-2-[3-[[[3-t-butyl-2-(tetradecyloxy)phenyl]acetyl]amino]phenyl]thiazolium chloride
3-ethyl-2-[3-[[[3-methoxy-2-(tetradecyloxy)phenyl]acetyl]amino]phenyl]thiazolium chloride
3-ethyl-2-[3-[[[2-chloro-4-(tetradecyloxy)phenyl]acetyl]amino]phenyl]thiazolium chloride
3-ethyl-2-[3-[[[4-chloro-3-(tetradecyloxy)phenyl]acetyl]amino]phenyl]thiazolium chloride
3-ethyl-2-[3-[[[4-chloro-2-(tetradecyloxy)phenyl]acetyl]amino]phenyl]thiazolium chloride
3-ethyl-2-[4-[[[-2-(tetradecyloxy)phenyl]acetyl]amino]phenyl]thiazolium chloride
3-ethyl-2-[4-[[[3-chloro-4-(tetradecyloxy)phenyl]acetyl]amino]phenyl]thiazolium chloride
3-ethyl-2-[4-[[[3-chloro-2-(tetradecyloxy)phenyl]acetyl]amino]phenyl]thiazolium chloride
3-ethyl-2-[4-[[[3-methoxy-2-(tetradecyloxy)phenyl]acetyl]amino]phenyl]thiazolium chloride
3-ethyl-2-[4-[[[2-chloro-4-(tetradecyloxy)phenyl]acetyl]amino]phenyl]thiazolium chloride
3-ethyl-2-[4-[[[4-chloro-3-(dodecyloxy)phenyl]acetyl]amino]phenyl]thiazolium chloride
3-ethyl-2-[4-[[[4-chloro-2-(tetradecyloxy)phenyl]acetyl]amino]phenyl]thiazolium chloride
3-ethyl-2-[4-[[[4-t-butyl-2-(tetradecyloxy)phenyl]acetyl]amino]phenyl]thiazolium chloride

EXAMPLE 76 p-Nitrophenyltetradecyl ether

A mixture of 75 g of p-nitrophenol, 149.5 g of 1-bromotetradecane, 26.96 g of sodium hydroxide, 2.18 g of methyltricaprylylammonium chloride in 400 ml of toluene and 400 ml of water is refluxed for 65 hours. The organic layer is separated, washed with 1N sodium hydroxide followed by 1N hydrochloric acid. The organic layer is dried and evaporated to a residue which is crystallized from petroleum ether to give the desired product as a white solid, m.p. 57°-60° C.

EXAMPLE 77 p-(Tetradecyloxy)aniline

A mixture of 30 g of p-nitrophenyltetradecylether, 2 g of 10% palladium-on-carbon in 150 ml of ethyl alcohol and 20 ml of ethyl acetate is shaken under pressurized hydrogen for 18 hours. The mixture is filtered and the filtrate evaporated. The residue is crystallized from hexanes to give 25.7 g of the desired product as a white solid, m.p. 65°-68° C.

EXAMPLE 78

3-(2-Bromomethyl)benzoyl chloride

To a mixture of 14.5 g of 3-(bromomethyl)benzoic acid and 11.41 g of oxalyl chloride in 100 ml of methylene chloride is added 5 drops of N,N-dimethylformamide followed by stirring at room temperature for 5 hours. The solvent is evaporated and the residue dissolved in ether:hexanes then filtered through diatomaceous earth. The filtrate is evaporated to give 15.4 g of the desired compound as a yellow liquid.

EXAMPLE 79

3-(Bromomethyl)-N-[4-(tetradecyloxy)phenyl]benzamide

To a mixture of 20.15 g of p-(tetradecyloxy)aniline and 20.87 g of pyridine in 150 ml of tetrahydrofuran cooled to 0° C. is added a solution of 15.4 g of 3-(2-bromomethyl)benzoyl chloride in 150 ml of tetrahydrofuran over 10 minutes. The mixture is stirred for 20 minutes at 0° C. and 20 minutes at room temperature. The mixture is diluted with chloroform and washed with 1N hydrochloric acid. The organic layer is dried and evaporated to a residue which is dissolved in hot acetone and 25 g of lithium bromide. The mixture is heated on a steam bath until all the solid dissolves. The solvent is evaporated and the residue partitioned between water and chloroform. The organic layer is separated, dried and filtered through a pad of silica gel. The solvent is removed and the residue crystallized from carbon tetrachloride:hexane to give 18.5 g of the desired product as a white solid, m.p. 140°-142° C.

EXAMPLE 80

5-Methyl-3-[[3-[[[4-(tetradecyloxy)phenyl]amino]carbonyl]phenyl]methyl]thiazolium bromide A mixture of 5.5 g of 3-(bromomethyl)-N-[4-(tetradecyloxy)phenyl]benzamide and 3.26 g of 5-methylthiazole in 60 ml of acetonitrile is refluxed under argon for 3 hours. The mixture is poured into 60 ml of acetonitrile and cooled to room temperature. The solid is collected, washed with ether and crystallized from acetonitrile to give 4.7 g of the desired product as a white solid, m.p. 123°-125° C.

According to the methods outlined hereinabove in Flowsheet H and described in detail in Examples 76–80, the compounds of this invention listed hereinbelow in List 9 can be prepared. These methods are applicable to the preparation of the compounds of this invention by one skilled in the art.

List 9

3-[[2-[[[-4-(tetradecyloxy)phenyl]amino]carbonyl]phenyl]methyl]thiazolium bromide
3-[[2-[[[3-methoxy-4-(tetradecyloxy)phenyl]amino)carbonyl]phenyl]methyl)thiazolium bromide
3-[[2-[[[3-methoxy-2-(tetradecyloxy)phenyl]amino]carbonyl]phenyl]methyl]thiazolium bromide
3-[[2-[[[2-chloro-4-(tetradecyloxy)phenyl]amino]carbonyl]phenyl]methyl]thiazolium bromide
3-[[2-[[[4-chloro-3-(tetradecyloxy)phenyl]amino]carbonyl]phenyl]methyl]thiazolium bromide
3-[[2-[[[4-t-butyl-2-(tetradecyloxy)phenyl]amino]carbonyl]phenyl]methyl]thiazolium bromide
3-[[2-[[[4-methoxy-3-(tetradecyloxy)phenyl]amino]carbonyl]phenyl]methyl]thiazolium bromide
3-([2-[[[4-methoxy-2-(tetradecyloxy)phenyl]amino)carbonyl]phenyl]methyl]thiazolium bromide
3-[[3-[[[-4-(tetradecyloxy)phenyl]amino]carbonyl]phenyl]methyl]thiazolium bromide
3-[[3-[[[-3-(tetradecyloxy)phenyl]amino]carbonyl]phenyl]methyl]thiazolium bromide
3-[[3-[[[3-chloro-2-(tetradecyloxy)phenyl]amino]carbonyl]phenyl]methyl]thiazolium bromide
3-[[3-[[[3-fluoro-4-(tetradecyloxy)phenyl]amino]carbonyl]phenyl]methyl]thiazolium bromide
3-[[3-[[[3-fluoro-2-(tetradecyloxy)phenyl]amino]carbonyl]phenyl]methyl]thiazolium bromide
3-[[3-[[[3-methoxy-4-(tetradecyloxy)phenyl]amino]carbonyl]phenyl]methyl]thiazolium bromide
3-[[3-[[[3-methoxy-2-(tetradecyloxy)phenyl]amino]carbonyl]phenyl]methyl]thiazolium bromide
3-[[3-[[[2-chloro-4-(tetradecyloxy)phenyl]amino]carbonyl]phenyl]methyl]thiazolium bromide
3-[[4-[[[-3-(hexadecyloxy)phenyl]amino]carbonyl]phenyl]methyl]thiazolium bromide
3-[[4-[[[-2-(tetradecyloxy)phenyl]amino]carbonyl]phenyl]methyl]thiazolium bromide
3-[[4-[[[-2-(hexadecyloxy)phenyl]amino]carbonyl]phenyl]methyl]thiazolium bromide
3-[[4-[[[3-chloro-4-(tetradecyloxy)phenyl]amino]carbonyl]phenyl]methyl]thiazolium bromide
3-[[4-[[[3-chloro-4-(hexadecyloxy)phenyl]amino]carbonyl]phenyl]methyl]thiazolium bromide
3-[[4-[[[3-chloro-2-(tetradecyloxy)phenyl]amino]carbonyl]phenyl]methyl]thiazolium bromide
3-[[4-[[[3-acetyl-2-(tetradecyloxy)phenyl]amino]carbonyl]phenyl]methyl]thiazolium bromide
3-[[4-[[[3-acetyl-2-(hexadecyloxy)phenyl]amino]carbonyl]phenyl]methyl]thiazolium bromide
3-[[4-[[[3-t-butyl-4-(tetradecyloxy)phenyl]amino]carbonyl]phenyl]methyl]thiazolium bromide
3-[[4-[[[3-t-butyl-4-(hexadecyloxy)phenyl]amino]carbonyl]phenyl]methyl]thiazolium bromide
3-[[4-[[[3-t-butyl-2-(tetradecyloxy)phenyl]amino]carbonyl]phenyl]methyl]thiazolium bromide
3-[[4-[[[3-methoxy-4-(hexadecyloxy)phenyl]amino]carbonyl]phenyl]methyl]thiazolium bromide
3-[[4-[[[3-methoxy-2-(tetradecyloxy)phenyl]amino]carbonyl]phenyl]methyl]thiazolium bromide
3-[[4-[[[3-methoxy-2-(hexadecyloxy)phenyl]amino]carbonyl]phenyl]methyl]thiazolium bromide
3-[[4-[[[2-chloro-4-(tetradecyloxy)phenyl]amino]carbonyl]phenyl]methyl]thiazolium bromide
5-Methyl-3-[[2-[[[-4-(tetradecyloxy)phenyl]amino]carbonyl]phenyl]methyl]thiazolium bromide
5-Methyl-3-[[2-[[[-3-(tetradecyloxy)phenyl]amino]carbonyl]phenyl]methyl]thiazolium bromide
5-Methyl-3-[[2-[[[-2-(tetradecyloxy)phenyl]amino]carbonyl]phenyl]methyl]thiazolium bromide
5-Methyl-3-[[2-[[[3-chloro-4-(tetradecyloxy)phenyl]amino]carbonyl]phenyl]methyl]thiazolium bromide
5-Methyl-3-[[2-[[[3-chloro-2-(tetradecyloxy)phenyl]amino]carbonyl]phenyl]methyl]thiazolium bromide
5-Methyl-3-[[2-[[[3-fluoro-4-(tetradecyloxy)phenyl]amino]carbonyl]phenyl]methyl]thiazolium bromide
5-Methyl-3-[[2-[[[3-fluoro-2-(tetradecyloxy)phenyl]amino]carbonyl]phenyl]methyl]thiazolium bromide
5-Methyl-3-[[2-[[[3-acetyl-2-(tetradecyloxy)phenyl]amino]carbonyl]phenyl]methyl]thiazolium bromide
5-Methyl-3-[[2-[[[3-t-butyl-4-(tetradecyloxy)phenyl]amino]carbonyl]phenyl]methyl]thiazolium bromide
5-Methyl-3-[[2-[[[3-t-butyl-2-(tetradecyloxy)phenyl]amino]carbonyl]phenyl]methyl]thiazolium bromide
5-Methyl-3-[[2-[[[3-methoxy-4-(tetradecyloxy)phenyl]amino]carbonyl]phenyl]methyl]thiazolium bromide
5-Methyl-3-[[2-[[[3-methoxy-2-(tetradecyloxy)phenyl]amino]carbonyl]phenyl]methyl]thiazolium bromide
5-Methyl-3-[[2-[[[2-chloro-4-(tetradecyloxy)phenyl]amino)carbonyl)phenyl)methyl]thiazolium bromide
5-Methyl-3-[[2-[[[4-chloro-3-(tetradecyloxy)phenyl]amino]carbonyl]phenyl]methyl]thiazolium bromide
5-Methyl-3-[[2-[[[4-t-butyl-2-(tetradecyloxy)phenyl]amino]carbonyl]phenyl]methyl]thiazolium bromide
5-Methyl-3-[[3-[[[3-chloro-2-(tetradecyloxy)phenyl]amino]carbonyl]phenyl]methyl]thiazolium bromide
5-Methyl-3-[[3-[[[3-chloro-2-(dodecyloxy)phenyl]amino]carbonyl]phenyl]methyl]thiazolium bromide
5-Methyl-3-[[3-[[[3-fluoro-4-(tetradecyloxy)phenyl]amino]carbonyl]phenyl]methyl]thiazolium bromide
5-Methyl-3-[[3-[[[3-fluoro-4-(dodecyloxy)phenyl]amino]carbonyl]phenyl]methyl]thiazolium bromide
5-Methyl-3-[[3-[[[3-fluoro-2-(tetradecyloxy)phenyl]amino]carbonyl]phenyl]methyl]thiazolium bromide
5-Methyl-3-[[3-[[[3-fluoro-2-(dodecyloxy)phenyl]amino]carbonyl]phenyl]methyl]thiazolium bromide
5-Methyl-3-[[3-[[[3-acetyl-4-(tetradecyloxy)phenyl]amino]carbonyl]phenyl]methyl]thiazolium bromide
5-Methyl-3-[[3-[[[3-acetyl-4-(dodecyloxy)phenyl]amino]carbonyl]phenyl]methyl]thiazolium bromide
5-Methyl-3-[[3-[[[3-acetyl-2-(tetradecyloxy)phenyl]amino]carbonyl]phenyl]methyl]thiazolium bromide
5-Methyl-3-[[3-[[[3-t-butyl-4-(dodecyloxy)phenyl]amino]carbonyl]phenyl]methyl]thiazolium bromide
5-Methyl-3-[[3-[[[2-chloro-4-(tetradecyloxy)phenyl]amino]carbonyl]phenyl]methyl]thiazolium bromide
5-Methyl-3-[[3-[[[4-chloro-3-(dodecyloxy)phenyl]amino]carbonyl]phenyl]methyl]thiazolium bromide
5-Methyl-3-[[3-[[[4-chloro-2-(tetradecyloxy)phenyl]amino]carbonyl]phenyl]methyl]thiazolium bromide
5-Methyl-3-[[3-[[[4-chloro-2-(dodecyloxy)phenyl]amino]carbonyl]phenyl]methyl]thiazolium bromide
5-Methyl-3-[[3-[[[4-t-butyl-3-(decyloxy)phenyl]amino]carbonyl]phenyl]methyl]thiazolium bromide
5-Methyl-3-[[3-[[[4-methoxy-3-(hexadecyloxy)phenyl]amino]carbonyl]phenyl]methyl]thiazolium bromide
5-Methyl-3-[[3-[[[4-methoxy-2-(tetradecyloxy)phenyl]amino]carbonyl)phenyl]methyl]thiazolium bromide 5-Methyl-3-[[3-[[[4-methoxy-2-(dodecyloxy)phenyl]amino]carbonyl]phenyl]methyl]thiazolium bromide
5-Methyl-3-[[4-[[[-4-(tetradecyloxy)phenyl]amino]carbonyl]phenyl]methyl]thiazolium bromide
5-Methyl-3-[[4-[[[-3-(tetradecyloxy)phenyl]amino)carbonyl]methyl)thiazolium bromide
5-Methyl-3-[[4-[[[-2-(tetradecyloxy)phenyl]amino]carbonyl]phenyl]methyl]thiazolium bromide
5-Methyl-3-[[4-[[[3-acetyl-4-(tetradecyloxy)phenyl]amino]carbonyl]phenyl]methyl]thiazolium bromide
5-Methyl -3-[[4-[[[3-acetyl -2-(tetradecyloxy)phenyl]amino]carbonyl]phenyl]methyl]thiazolium bromide
5-Methyl-3-[[4-[[[3-t-butyl-4-(decyloxy)phenyl]amino]carbonyl]phenyl]methyl]thiazolium bromide
5-Methyl-3-[[4-[[[3-t-butyl-2-(tetradecyloxy)phenyl]amino]carbonyl]phenyl]methyl]thiazolium bromide
5-Methyl-3-[[4-[[[3-methoxy-4-(tetradecyloxy)phenyl]amino]carbonyl]phenyl]methyl]thiazolium bromide
5-Methyl-3-[[4-[[[3-methoxy-2-(tetradecyloxy)phenyl]amino]carbonyl]phenyl]methyl]thiazolium bromide
5-Methyl-3-[[4-[[[2-chloro-4-(tetradecyloxy)phenyl]amino]carbonyl]phenyl]methyl]thiazolium bromide
5-Methyl-3-[[4-[[[4-chloro-3-(tetradecyloxy)phenyl]amino]carbonyl]phenyl]methyl]thiazolium bromide;
5-Methyl-3-[[4-[[[4-chloro-2-(tetradecyloxy)phenyl]amino]carbonyl]phenyl]methyl]thiazolium bromide
5-Methyl-3-[[4-[[[4-t-butyl-3-(tetradecyloxy)phenyl]amino]carbonyl]phenyl]methyl]thiazolium bromide
5-Methyl-3-[[4-[[[4-t-butyl-2-(tetradecyloxy)phenyl]amino]carbonyl]phenyl)methyl]thiazolium bromide
5-Methyl-3-[[4-[[[4-methoxy-3-(tetradecyloxy)phenyl]amino]carbonyl]phenyl]methyl]thiazolium bromide
5-Methyl-3-[[4-[[[4-methoxy-2-(tetradecyloxy)phenyl]amino]carbonyl]phenyl]methyl]thiazolium bromide
2-Methyl-3-[[2-[[[-4-(tetradecyloxy)phenyl]amino]carbonyl]phenyl]methyl]thiazolium bromide
2-Methyl-3-[[2-[[[2-chloro-4-(tetradecyloxy)phenyl]amino]carbonyl]phenyl]methyl]thiazolium bromide
2-Methyl-3-[[2-[[[4-chloro-3-(tetradecyloxy)phenyl]amino]carbonyl]phenyl]methyl]thiazolium bromide
2-Methyl-3-[[2-[[[4-chloro-2-(tetradecyloxy)phenyl]amino]carbonyl]phenyl]methyl]thiazolium bromide
2-Methyl-3-[[2-([[4-t-butyl-3-(tetradecyloxy)phenyl]amino]carbonyl)phenyl)methyl]thiazolium bromide
2-Methyl-3-[[2-[[[4-methoxy-2-(tetradecyloxy)phenyl]amino]carbonyl]phenyl]methyl]thiazolium bromide
2-Methyl-3-[[3-[[[-4-(tetradecyloxy)phenyl]amino]carbonyl)phenyl]methyl]thiazolium bromide
2-Methyl-3-[[3-[[[-3-(tetradecyloxy)phenyl]amino)carbonyl)phenyl]methyl)thiazolium bromide
2-Methyl-3-[[3-[[[-2-(tetradecyloxy)phenyl]amino]carbonyl]phenyl]methyl]thiazolium bromide
2-Methyl-3-[[3-[[[3-chloro-4-(tetradecyloxy)phenyl]amino]carbonyl]phenyl]methyl]thiazolium bromide
2-Methyl-3-[[3-[[[3-chloro-2-(tetradecyloxy)phenyl]amino]carbonyl]phenyl]methyl]thiazolium bromide
2-Methyl-3-[[3-[[[3-fluoro-4-(tetradecyloxy)phenyl]amino]carbonyl]phenyl]methyl]thiazolium bromide
2-Methyl-3-[[3-[[[3-fluoro-2-(tetradecyloxy)phenyl]amino]carbonyl]phenyl]methyl]thiazolium bromide
2-Methyl-3-[[3-[[[2-chloro-4-(tetradecyloxy)phenyl]amino]carbonyl]phenyl]methyl]thiazolium bromide
2-Methyl-3-[[3-[[[4-t-butyl-3-(tetradecyloxy)phenyl]amino]carbonyl]phenyl]methyl]thiazolium bromide
2-Methyl-3-[[4-[[[3-fluoro-2-(tetradecyloxy)phenyl]amino]carbonyl]phenyl]methyl]thiazolium bromide
2-Methyl-3-[[4-[[[3-acetyl-4-(tetradecyloxy)phenyl]amino]carbonyl]phenyl]methyl]thiazolium bromide
2-Methyl-3-[[4-[[[3-acetyl-2-(tetradecyloxy)phenyl]amino]carbonyl]phenyl)methyl]thiazolium bromide
2-Methyl-3-[[4-[[[3-methoxy-4-(tetradecyloxy)phenyl]amino]carbonyl]phenyl]methyl]thiazolium bromide
2-Methyl-3-[[4-[[[4-methoxy-3-(tetradecyloxy)phenyl]amino)carbonyl]phenyl]methyl]thiazolium bromide
2-Methyl-3-[[4-[[[4-methoxy-2-(tetradecyloxy)phenyl]amino]carbonyl]phenyl]methyl]thiazolium bromide
4-Methyl-3-[[2-[[[-4-(tetradecyloxy)phenyl]amino]carbonyl]phenyl]methyl]thiazolium bromide
4-Methyl-3-[[2-[[[-3-(tetradecyloxy)phenyl]amino]carbonyl]phenyl]methyl]thiazolium bromide
4-Methyl-3-[[2-[[[-2-(tetradecyloxy)phenyl]amino]carbonyl]phenyl)methyl]thiazolium bromide
4-Methyl-3-[[2-[[[3-chloro-4-(tetradecyloxy)phenyl]amino]carbonyl]phenyl]methyl]thiazolium bromide
4-Methyl-3-[[2-[[[3-chloro-2-(tetradecyloxy)phenyl]amino]carbonyl]phenyl]methyl]thiazolium bromide
4-Methyl-3-[[2-[[[3-fluoro-4-(tetradecyloxy)phenyl]amino)carbonyl]phenyl]methyl)thiazolium bromide
4-Methyl-3-[[2-[[[3-fluoro-2-(tetradecyloxy)phenyl]amino]carbonyl]phenyl]methyl]thiazolium bromide
4-Methyl-3-[[2-[[[3-acetyl-4-(tetradecyloxy)phenyl]amino]carbonyl]phenyl]methyl]thiazolium bromide
4-Methyl-3-[[2-[[[3-acetyl-2-(tetradecyloxy)phenyl]amino]carbonyl]phenyl]methyl]thiazolium bromide
4-Methyl-3-[[2-[[[3-t-butyl-4-(tetradecyloxy)phenyl]amino]carbonyl]phenyl]methyl]thiazolium bromide
4-Methyl-3-[[3-[[[-2-(tetradecyloxy)phenyl]amino]carbonyl]phenyl]methyl]thiazolium bromide
4-Methyl -3-[[3-[[[3-chloro-4-(octyloxy)phenyl]amino]carbonyl]phenyl]methyl]thiazolium bromide
4-Methyl-3-[[3-[[[3-chloro-2-(tetradecyloxy)phenyl]amino]carbonyl]phenyl]methyl]thiazolium bromide
4-Methyl-3-[[3-[[[3-fluoro-4-(tetradecyloxy)phenyl]amino]carbonyl]phenyl]methyl]thiazolium bromide
4-Methyl-3-[[3-[[[3-fluoro-2-(tetradecyloxy)phenyl]amino]carbonyl]phenyl]methyl]thiazolium bromide
4-Methyl-3-[[3-[[[3-acetyl-4-(tetradecyloxy)phenyl]amino]carbonyl]phenyl]methyl]thiazolium bromide
4-Methyl-3-[[3-[[[3-acetyl-2-(tetradecyloxy)phenyl]amino]carbonyl]phenyl]methyl]thiazolium bromide
4-Methyl-3-[[3-[[[3-t-butyl-4-(decyloxy)phenyl]amino]carbonyl]phenyl]methyl]thiazolium bromide
4-Methyl-3-[[3-[[[3-t-butyl-2-(tetradecyloxy)phenyl]amino]carbonyl]phenyl]methyl]thiazolium bromide
4-Methyl-3-[[3-[[[3-methoxy-2-(tetradecyloxy)phenyl]amino]carbonyl]phenyl]methyl]thiazolium bromide
4-Methyl-3-[[3-[[[2-chloro-4-(tetradecyloxy)phenyl]amino]carbonyl]phenyl]methyl]thiazolium bromide
4-Methyl-3-[[3-[[[4-chloro-3-(tetradecyloxy)phenyl]amino]carbonyl]phenyl]methyl]thiazolium bromide
4-Methyl-3-[[3-[[[4-chloro-2-(tetradecyloxy)phenyl]amino]carbonyl]phenyl]methyl]thiazolium bromide
4-Methyl-3-[[4-[[[-2-(tetradecyloxy)phenyl]amino]carbonyl]phenyl]methyl]thiazolium bromide
4-Methyl-3-[[4-[[[3-chloro-4-(tetradecyloxy)phenyl]amino)carbonyl)phenyl]methyl)thiazolium bromide
4-Methyl-3-[[4-[[[3-chloro-2-(tetradecyloxy)phenyl]amino]carbonyl]phenyl]methyl]thiazolium bromide
4-Methyl-3-[[4-[[[3-methoxy-2-(tetradecyloxy)phenyl]amino]carbonyl]phenyl]methyl]thiazolium bromide
4-Methyl-3-[[4-[[[2-chloro-4-(tetradecyloxy)phenyl)amino]carbonyl]phenyl]methyl]thiazolium bromide
4-Methyl-3-[[4-[[[4-chloro-3-(dodecyloxy)phenyl]amino) carbonyl) phenyl]methyl]thiazolium bromide
4-Methyl-3-[[4-[[[4-chloro-2-(tetradecyloxy)phenyl]amino]carbonyl]phenyl]methyl]thiazolium bromide 4-Methyl-3-[[4-[[[4-t-butyl-2-(tetradecyloxy)phenyl]amino]carbonyl)phenyl]methyl]thiazolium bromide

EXAMPLE 81

N-[3-(Hydroxymethyl)phenyl]-4-(tetradecyloxy)benzeneacetamide

To a solution of 15.5 g of m-aminobenzyl alcohol and 36.21 g of pyridine in 250 ml of tetrahydrofuran, cooled to 0° C. is added over 40 minutes a solution of 42 g of p-tetradecyloxyphenylacetyl chloride in 250 ml of tetrahydrofuran. The mixture is stirred overnight at room temperature and the solvent is evaporated. The residue is partitioned between water and chloroform with some heating to afford a complete solution. The hot chloroform solution is washed with warm water and warm dilute hydrochloric acid. The organic layer is dried and evaporated to a residue which is crystallized from carbon tetrachloride to give 40 g of the desired product as a white solid.

EXAMPLE 82

N-[3-(Bromomethyl)phenyl]-4-tetradecyloxy)benzeneacetamide

A mixture of 20 g of N-[3-(hydroxymethyl)phenyl]-4-(tetradecyloxy)benzeneacetamide, 160 ml of 30% HBr in acetic acid and 60 ml of chloroform is refluxed for 2 hours. The mixture is poured into water and extracted with chloroform. The organic layer is washed with water, saturated with sodium bicarbonate, dried and filtered through a short pad of silica gel. The solvent is evaporated and the residue crystallized from carbon tetrachloride:hexane to give 18 g of the desired product as a white solid.

EXAMPLE 83

4-(Tetradecyloxy)-N-[3-(2-thiazolylmethyl)phenyl]benzeneacetamide

A mixture of 6 g of N-[3-(bromomethyl)phenyl]-4-tetradecyloxy)benzeneacetamide, 3.83 g of 2-(trimethylstannyl)thiazole and 407.63 mg of dichlorobis(triphenylphosphine)palladium in 100 ml of tetrahydrofuran is refluxed under argon for 14 hours. The mixture is filtered through a pad of silica gel followed by ether washing. The organic layer is washed with 1N sodium hydroxide, dried and evaporated to a residue which is chromatographed on silica gel eluting with 2:1 hexane:ethyl acetate to give 1.4 g of the desired product as an off-white powder.

EXAMPLE 84

4-(Tetradecyloxy)-N-[3-(2-thiazolylmethyl)phenyl]benzeneacetamide monohydrochloride To a tetrahydrofuran:ether solution of 4-(tetradecyloxy)-N-[3-(2-thiazolylmethyl)phenyl]benzeneacetamide is added ether saturated with hydrogen chloride. The resulting solid is collected by centrifugation and dried in vacuum to give 0.18 g of the desired product as a tan solid, m.p. 155°–158° C.

EXAMPLE 85

3-Methyl-2-[[3-[[[4-(tetradecyloxy)phenyl]acetyl]amino]phenyl]methyl]thiazolium bromide A mixture of 500 mg of 4-(tetradecyloxy)-N-[3-(2-thiazolylmethyl)phenyl]benzeneacetamide and 6.13 g of methyl iodide in 12 ml of acetonitrile is heated in a pressure vessel under argon for 2 hours. The solvent is removed and the residue dissolved in a minimum of chloroform followed by dilution with ether. The resulting solid is collected by centrifugation, washed with ether and vacuum dried to give 0.6 g of the desired compound as a tan solid, m.p. 192°–195° C.

EXAMPLE 86

N-[4-(Hydroxymethyl)phenyl]-4-(tetradecyloxy)benzamide

To a mixture of 9.75 g of p-aminobenzyl alcohol and 19.27 g of pyridine in 230 ml of methylene chloride cooled to 0° C. is added over 35 minutes a solution of 21.5 g of 4-tetradecyloxybenzoyl chloride in 230 ml of methylene chloride. The mixture is stirred at room temperature for 2 hours and diluted with chloroform. The mixture is heated to dissolve insolubles, washed with hot water and hot dilute hydrochloric acid then dried. The mixture is filtered hot and the solvent evaporated to a residue which is crystallized from tetrahydrofuran:hexane to give 18.1 g of the desired product as a yellow powder, m.p. 140°–145° C.

EXAMPLE 87

4-[[[4-(Tetradecyloxy)phenyl]methyl]amino]benzenemethanol

To a suspension of 13 g of N-[4-(hydroxymethyl)phenyl]-4-(tetradecyloxy)benzamide in 250 ml of tetrahydrofuran is added dropwise with stirring under argon 59.14 ml of 1 molar lithium aluminum hydride in tetrahydrofuran. The mixture is stirred at room temperature for 0.5 hours and refluxed for 5 hours. Ethylacetate is added dropwise followed by water. The mixture is filtered and the cake washed with ether. The filtrate is evaporated to a residue which is purified by chromatography on silica gel with 2:1 chloroform:hexane to give the desired product.

EXAMPLE 88

4-[[[4-(Tetradecyloxy)phenyl]methyl]amino]benzenemethanol

A mixture of 20 g of 7.73 g of p-aminobenzyl alcohol and 3.95 g of sodium cyanoborohydride in 200 ml of ethyl alcohol is refluxed for 7 hours. The mixture is poured into water and extracted with warm chloroform. The organic layer is washed with saturated sodium bicarbonate, dried and evaporated to a residue which is crystallized from methyl alcohol followed by purification on silica gel using 3:1 hexane:ethyl acetate to give 9.0 g of the desired product as a yellow solid, m.p. 85°–87° C.

EXAMPLE 89

N-[4-(Hydroxymethyl)phenyl]-N-[[4-tetradecyloxy)phenyl]methyl]acetamide

To a 0° C. solution of 8.3 g of 4-[[[4-(tetradecyloxy)phenyl]methyl]amino]benzenemethanol in 70 ml of methylene chloride containing 6.17 g of pyridine is added 5.36 g of acetyl chloride in 10 ml of methylene chloride followed by stirring at room temperature for 1.5 hours. The mixture is poured into water and extracted with chloroform. The organic layer is separated and washed with dilute hydrochloric acid and saturated sodium bicarbonate. The organic layer is dried and evaporated to a residue which is dissolved in 80 ml of ethyl alcohol, 1.3 ml of water and 1.09 g of sodium hydroxide. The mixture is stirred for 40 minutes, poured into water and extracted with ether. The organic layer is dried and evaporated to a residue which is crystallized from carbon tetrachloride:petroleum ether to give 7.1 g of the desired product as a white solid, m.p. 76°-79° C.

EXAMPLE 90

N-[4-(Bromomethyl)phenyl]-N-[[4-(tetradecyloxy)phenyl]methyl]acetamide

To a solution of 6.9 g of N-[4-(hydroxymethyl)phenyl]-N-[[4-tetradecyloxy)phenyl]methyl]acetamide in 100 ml of tetrahydrofuran is added 2.25 g of methanesulfonyl chloride and 1.79 g of triethylamine followed by stirring for 3.5 hours. Also added is 12.81 g of lithium bromide followed by stirring for 18 hours. The mixture is poured into water and extracted with ether. The organic layer is dried and evaporated to a residue which is crystallized from petroleum ether to give 6.8 g of the desired product as a white solid, m.p. 46°-49° C.

EXAMPLE 91

3-[[4-acetyl[[4-(tetradecyloxy)phenyl]methyl]amino]phenyl]methyl]-5-methyl thiazolium bromide A mixture of 3.5 g of N-[4-(bromomethyl)phenyl]-N-[[4-(tetradecyloxy)phenyl]methyl]acetamide and 1.96 g of 5-methylthiazole in 50 ml of acetonitrile is refluxed under argon for 4.5 hours. The solvent is evaporated and the residue mixed with ether. The solid is collected by centrifugation, washed with ether several times and dried under vacuum to give 2.8 g of the desired product as a white powder, m.p. 95°-98° C.

According to the methods outlined hereinabove in Flowsheet C and described in detail in Examples 29-32, 64, 65, 86-91, the compounds of this invention listed hereinbelow in List 10 can be prepared. These methods are applicable to the preparation of the compounds of this invention by one skilled in the art.

List 10

3-[[4-[Acetyl[[4-(tetradecyloxy)phenyl]methyl]amino]phenyl]methyl]thiazolium bromide
3-[[4-[Acetyl[[4-(tetradecyloxy)phenyl]methyl]amino]phenyl]methyl]-5-methyl-thiazolium bromide
3-[[4-[Acetyl[[4-(dodecyloxy)phenyl]methyl]amino]phenyl]methyl]thiazolium bromide
3-[[4-[Acetyl[[4-(hexadecyloxy)phenyl]methyl]amino]phenyl]methyl]-5-methyl-thiazolium bromide
3-[[4-[Acetyl[[3-(tetradecyloxy)phenyl]methyl]amino]phenyl]methyl]thiazolium bromide
3-[[4-[Acetyl[[3-(tetradecyloxy)phenyl]methyl]amino]phenyl]methyl]-5-methyl-thiazolium bromide
3-[[4-[Acetyl[[3-(dodecyloxy)phenyl]methyl]amino]phenyl]methyl]thiazolium bromide
3-[[4-[Acetyl[[3-(dodecyloxy)phenyl]methyl]amino]phenyl]methyl]-5-methyl-thiazolium bromide
3-[[4-[Acetyl[[3-chloro-4-(tetradecyloxy)phenyl]methyl]amino]phenyl]methyl]thiazolium bromide
3-[[4-[Acetyl[[3-chloro-4-(tetradecyloxy)phenyl]methyl]amino]phenyl]methyl]-5-methyl-thiazolium bromide
3-[[4-[Acetyl[[3-fluoro-4-(tetradecyloxy)phenyl]methyl]amino]phenyl]methyl]thiazolium bromide
3-[[4-[Acetyl[[3-fluoro-4-(tetradecyloxy)phenyl]methyl]amino]phenyl]methyl]-5-methyl-thiazolium bromide
3-[[4-[Acetyl[[3-t-butyl-4-(tetradecyloxy)phenyl]methyl]amino]phenyl]methyl]thiazolium bromide
3-[[4-[Acetyl[[3-t-butyl-4-(tetradecyloxy)phenyl]methyl]amino]phenyl]methyl]-5-methyl-thiazolium bromide
3-[[4-[Acetyl[[3-methoxy-4-(tetradecyloxy)phenyl]methyl]amino]phenyl]methyl]thiazolium bromide
3-[[4-[Acetyl[[3-methoxy-4-(tetradecyloxy)phenyl]methyl]amino]phenyl]methyl]-5-methyl-thiazolium bromide
3-[[4-[Acetyl[[4-chloro-3-(tetradecyloxy)phenyl]methyl]amino]phenyl]methyl]thiazolium bromide
3-[[4-[Acetyl[[4-chloro-3-(tetradecyloxy)phenyl]methyl]amino]phenyl]methyl]-5-methyl-thiazolium bromide
3-[[4-[Acetyl[[4-t-butyl-3-(tetradecyloxy)phenyl]methyl]amino]phenyl]methyl]thiazolium bromide
3-[[4-[Acetyl[[4-t-butyl-3-(tetradecyloxy)phenyl]methyl]amino]phenyl]methyl]-5-methyl-thiazolium bromide
3-[[4-[Acetyl[[4-methoxy-3-(tetradecyloxy)phenyl]methyl]amino]phenyl]methyl]thiazolium bromide
3-[[4-[Acetyl[[4-methoxy-3-(tetradecyloxy)phenyl]methyl]amino]phenyl]methyl]-5-methyl-thiazolium bromide
3-[[4-[[1-oxopropyl][[4-(tetradecyloxy)phenyl]methyl]amino]phenyl]methyl]thiazolium bromide
3-[[4-[[1-oxopropyl][[4-(tetradecyloxy)phenyl]methyl]amino]phenyl]methyl]-5-methyl-thiazolium bromide
3-[[4-[[1-oxopropyl][[4-(dodecyloxy)phenyl]methyl]amino]phenyl]methyl]thiazolium bromide
3-[[4-[[1-oxopropyl][[4-(dodecyloxy)phenyl]methyl]amino]phenyl]methyl]-5-methyl-thiazolium bromide
3-[[4-[[1-oxopropyl][[3-(tetradecyloxy)phenyl]methyl]amino]phenyl]methyl]thiazolium bromide
3-[[4-[[1-oxopropyl][[3-(tetradecyloxy)phenyl]methyl]amino]phenyl]methyl]-5-methyl-thiazolium bromide
3-[[4-[[1-oxopropyl][[3-(dodecyloxy)phenyl]methyl]amino]phenyl]methyl]thiazolium bromide
3-[[4-[[1-oxopropyl][[3-(dodecyloxy)phenyl]methyl]amino]phenyl]methyl]-5-methyl-thiazolium bromide
3-[[4-[[1-oxopropyl][[3-chloro-4-(tetradecyloxy)phenyl]methyl]amino]phenyl]methyl]thiazolium bromide
3-[[4-[[1-oxopropyl][[3-chloro-4-(tetradecyloxy)phenyl]methyl]amino]phenyl]methyl]-5-methyl-thiazolium bromide
3-[[4-[[1-oxopropyl][[3-fluoro-4-(tetradecyloxy)phenyl]methyl]amino]phenyl]methyl]thiazolium bromide
3-[[4-[[1-oxopropyl][[3-fluoro-4-(tetradecyloxy)phenyl]methyl]amino]phenyl]methyl]-5-methyl-thiazolium bromide
3-[[4-[[1-oxopropyl][[3-t-butyl-4-(tetradecyloxy)phenyl]methyl]amino]phenyl]methyl]thiazolium bromide
3-[[4-[[1-oxopropyl][[3-t-butyl-4-(tetradecyloxy)phenyl]methyl]amino]phenyl]methyl]-5-methyl-thiazolium bromide
3-[[4-[[1-oxopropyl][[3-methoxy-4-(tetradecyloxy)phenyl]methyl]amino]phenyl]methyl]thiazolium bromide
3-[[4-[[1-oxopropyl][[3-methoxy-4-(tetradecyloxy)phenyl]methyl]amino]phenyl]methyl]-5-methyl-thiazolium bromide
3-[[4-[[1-oxopropyl][[4-chloro-3-(tetradecyloxy)phenyl]methyl]amino]phenyl]methyl]thiazolium bromide 3-[[4-[[1-oxopropyl][[4-chloro-3-(tetradecyloxy)-phenyl]methyl]amino]phenyl]methyl]-5-methyl-thiazolium bromide 3-[[4-[[1-oxopropyl][[4-t-butyl-3-(tetradecyloxy)-phenyl]methyl]amino]phenyl]methyl]thiazolium bromide 3-[[4-[[1-oxopropyl][[4-t-butyl-3-(tetradecyloxy)-phenyl]methyl]amino]phenyl]methyl]-5-methyl-thiazolium bromide 3-[[4-[[1-oxopropyl][[4-methoxy-3-(tetradecyloxy)-phenyl]methyl]amino]phenyl]methyl]thiazolium bromide 3-[[4-[[1-oxopropyl][[4-methoxy-3-(tetradecyloxy)-phenyl]methyl]amino]phenyl]methyl]-5-methyl-thiazolium bromide 3-[[3-[Acetyl[[4-(tetradecyloxy)phenyl]methyl]amino]-phenyl]methyl]thiazolium bromide 3-[[3-[Acetyl[[4-(tetradecyloxy)phenyl]methyl]amino]-phenyl]methyl]-5-methyl-thiazolium bromide 3-[[3-[Acetyl[[4-(hexadecyloxy)phenyl]methyl]amino]-phenyl]methyl]thiazolium bromide 3-[[3-[Acetyl[[4-(dodecyloxy)phenyl]methyl]amino]-phenyl]methyl]-5-methyl-thiazolium bromide 3-[[3-[Acetyl[[3-(tetradecyloxy)phenyl]methyl]amino]-phenyl]methyl]thiazolium bromide 3-[[3-[Acetyl[[3-(tetradecyloxy)phenyl]methyl]amino]-phenyl]methyl]-5-methyl-thiazolium bromide 3-[[3-[Acetyl[[3-(hexadecyloxy)phenyl]methyl]amino]-phenyl]methyl]thiazolium bromide 3-[[3-[Acetyl[[3-(hexadecyloxy)phenyl]methyl]amino]-phenyl]methyl]-5-methyl-thiazolium bromide 3-[[3-[Acetyl[[3-chloro-4-(tetradecyloxy)phenyl]methyl]amino]phenyl]methyl]thiazolium bromide 3-[[3-[Acetyl[[3-chloro-4-(tetradecyloxy)phenyl]methyl]amino]phenyl]methyl]-5-methyl-thiazolium bromide 3-[[3-[Acetyl[[3-chloro-4-(hexadecyloxy)phenyl]methyl]amino]phenyl]methyl]thiazolium bromide 3-[[3-[Acetyl[[3-chloro-4-(hexadecyloxy)phenyl]methyl]amino]phenyl]methyl]-5-methyl-thiazolium bromide 3-[[3-[Acetyl[[3-fluoro-4-(tetradecyloxy)phenylmethyl]amino]phenyl]methyl]thiazolium bromide 3-[[3-[Acetyl[[3-fluoro-4-(tetradecyloxy)phenyl]methyl]amino]phenyl]methyl]-5-methyl-thiazolium bromide 3-[[3-[Acetyl[[3-t-butyl-4-(tetradecyloxy)phenyl]methyl]amino]phenyl]methyl]thiazolium bromide 3-[[3-[Acetyl[[3-t-butyl-4-(tetradecyloxy)phenyl]methyl]amino]phenyl]methyl]-5-methyl-thiazolium bromide 3-[[3-[Acetyl[[3-methoxy-4-(tetradecyloxy)phenyl]methyl]amino]phenyl]methyl]thiazolium bromide 3-[[3-[Acetyl[[3-methoxy-4-(tetradecyloxy)phenyl]methyl]amino]phenyl]methyl]-5-methyl-thiazolium bromide 3-[[3-[Acetyl[[4-chloro-3-(tetradecyloxy)phenyl]methyl]amino]phenyl]methyl]thiazolium bromide 3-[[3-[Acetyl[[4-chloro-3-(tetradecyloxy)phenyl]methyl]amino]phenyl]methyl]-5-methyl-thiazolium bromide 3-[[3-[Acetyl[[4-t-butyl-3-(tetradecyloxy)phenyl]methyl]amino]phenyl]methyl]thiazolium bromide 3-[[3-[Acetyl[[4-t-butyl-3-(tetradecyloxy)phenyl]methyl]amino]phenyl]methyl]-5-methyl-thiazolium bromide 3-[[3-[Acetyl[[4-methoxy-3-(tetradecyloxy)phenyl]methyl]amino]phenyl]methyl]thiazolium bromide 3-[[3-[Acetyl[[4-methoxy-3-(tetradecyloxy)phenyl]methyl]amino]phenyl]methyl]-5-methyl-thiazolium bromide 3-[[3-[[1-oxopropyl][[4-(tetradecyloxy)phenyl]methyl]amino]phenyl]methyl]thiazolium bromide 3-[[3-[[1-oxopropyl][[4-(tetradecyloxy)phenyl]methyl]amino]phenyl]methyl]-5-methyl-thiazolium bromide 3-[[3-[[1-oxopropyl][[3-(tetradecyloxy)phenyl]methyl]amino]phenyl]methyl]thiazolium bromide 3-[[3-[[1-oxopropyl][[3-(tetradecyloxy)phenyl]methyl]amino]phenyl]methyl]-5-methyl-thiazolium bromide 3-[[3-[[1-oxopropyl][[3-chloro-4-(tetradecyloxy)-phenyl]methyl]amino]phenyl]methyl]thiazolium bromide 3-[[3-[[1-oxopropyl][[3-chloro-4-(tetradecyloxy)-phenyl]methyl]amino]phenyl]methyl]-5-methyl-thiazolium bromide 3-[[3-[[1-oxopropyl][[3-fluoro-4-(tetradecyloxy)-phenyl]methyl]amino]phenyl]methyl]thiazolium bromide 3-[[3-[[1-oxopropyl][[3-fluoro-4-(tetradecyloxy)-phenyl]methyl]amino]phenyl]methyl]-5-methyl-thiazolium bromide 3-[[3-[[1-oxopropyl][[3-t-butyl-4-(tetradecyloxy)-phenyl]methyl]amino]phenyl]methyl]thiazolium bromide 3-[[3-[[1-oxopropyl][[3-t-butyl-4-(tetradecyloxy)-phenyl]methyl]amino]phenyl]methyl]-5-methyl-thiazolium bromide 3-[[3-[[1-oxopropyl][[3-methoxy-4-(tetradecyloxy)-phenyl]methyl]amino]phenyl]methyl]thiazolium bromide 3-[[3-[[1-oxopropyl][[3-methoxy-4-(tetradecyloxy)-phenyl]methyl]amino]phenyl]methyl]-5-methyl-thiazolium bromide 3-[[3-[[1-oxopropyl][[4-chloro-3-(tetradecyloxy)-phenyl]methyl]amino]phenyl]methyl]thiazolium bromide 3-[[3-[[1-oxopropyl][[4-chloro-3-(tetradecyloxy)phenylmethyl]amino]phenyl]methyl]-5-methyl-thiazolium bromide 3-[[3-[[1-oxopropyl][[4-t-butyl-3-(tetradecyloxy)-phenyl]methyl]amino]phenyl]methyl]thiazolium bromide 3-[[3-[[1-oxopropyl][[4-t-butyl-3-(tetradecyloxy)-phenyl]methyl]amino]phenyl]methyl]-5-methyl-thiazolium bromide 3-[[3-[[1-oxopropyl][[4-methoxy-3-(tetradecyloxy)-phenyl]methyl]amino]phenyl]methyl]thiazolium bromide 3-[[3-[[1-oxopropyl][[4-methoxy-3-(tetradecyloxy)-phenyl]methyl]amino]phenyl]methyl]-5-methyl-thiazolium bromide 3-[[2-[Acetyl[[4-(tetradecyloxy)phenyl]methyl]amino]-phenyl]methyl]-5-methyl-thiazolium bromide 3-[[2-[Acetyl[[3-(tetradecyloxy)phenyl]methyl]amino]-phenyl]methyl]-5-methyl-thiazolium bromide 3-[[2-[Acetyl[[3-chloro-4-(tetradecyloxy)phenyl]methyl]amino]phenyl]methyl]-5-methyl-thiazolium bromide 3-[[2-[Acetyl[[3-fluoro-4-(tetradecyloxy)phenyl]methyl]amino]phenyl]methyl]-5-methyl-thiazolium bromide 3-[[2-[Acetyl[[3-methoxy-4-(tetradecyloxy)phenyl]methyl]amino]phenyl]methyl]-5-methyl-thiazolium bromide 3-[[2-[Acetyl[[4-chloro-3-(tetradecyloxy)phenyl]methyl]amino]phenyl]methyl]-5-methyl-thiazolium bromide 3-[[2-[Acetyl[[4-methoxy-3-(tetradecyloxy)phenyl]methyl]amino]phenyl]methyl]-5-methyl-thiazolium bromide 3-[[4-[Acetyl[[4-(tetradecyloxy)phenyl]methyl]amino]phenyl]methyl]pyridinium bromide 3-[[4-[Acetyl[[4-(tetradecyloxy)phenyl]methyl]amino]phenyl]methyl]-3,4-dimethyl-pyridinium bromide 3-[[4-[Acetyl[[4-(dodecyloxy)phenyl]methyl]amino]phenyl]methyl]pyridinium bromide 3-[[4-[Acetyl[[4-(hexadecyloxy)phenyl]methyl]amino]phenyl]methyl]-3,4-dimethyl-pyridinium bromide 3-[[4-[Acetyl[[3-(tetradecyloxy)phenyl]methyl]amino]phenyl]methyl]pyridinium bromide 3-[[4-[Acetyl[[3-(tetradecyloxy)phenyl]methyl]amino]phenyl]methyl]-3,4-dimethyl-pyridinium bromide 3-[[4-[Acetyl[[3-(dodecyloxy)phenyl]methyl]amino]phenyl]methyl]pyridinium bromide 3-[[4-[Acetyl[[3-(dodecyloxy)phenyl]methyl]amino]phenyl]methyl]-3,4-dimethyl-pyridinium bromide 3-[[4-[Acetyl[[3-chloro-4-(tetradecyloxy)phenyl]methyl]amino]phenyl]methyl]pyridinium bromide 3-[[4-[Acetyl[[3-chloro-4-(tetradecyloxy)phenyl]methyl]amino]phenyl]methyl]-3,4-dimethyl-pyridinium bromide 3-[[4-[Acetyl[[3-fluoro-4-(tetradecyloxy)phenyl]methyl]amino]phenyl]methyl]pyridinium bromide 3-[[4-[Acetyl[[3-fluoro-4-(tetradecyloxy)phenyl]methyl]amino]phenyl]methyl]-3,4-dimethyl-pyridinium bromide 3-[[4-[Acetyl[[3-t-butyl-4-(tetradecyloxy)phenyl]methyl]amino]phenyl]methyl]pyridinium bromide 3-[[4-[Acetyl[[3-t-butyl-4-(tetradecyloxy)phenyl]methyl]amino]phenyl]methyl]-3,4-dimethyl-pyridinium bromide 3-[[4-[Acetyl[[3-methoxy-4-(tetradecyloxy)phenyl]methyl]amino]phenyl]methyl]pyridinium bromide 3-[[4-[Acetyl[[3-methoxy-4-(tetradecyloxy)phenyl]methyl]amino]phenyl]methyl]-3,4-dimethyl-pyridinium bromide 3-[[4-[Acetyl[[4-chloro-3-(tetradecyloxy)phenyl]methyl]amino]phenyl]methyl]pyridinium bromide 3-[[4-[Acetyl[[4-chloro-3-(tetradecyloxy)phenyl]methyl]amino]phenyl]methyl]-3,4-dimethyl-pyridinium bromide 3-[[4-[Acetyl[[4-t-butyl-3-(tetradecyloxy)phenyl]methyl]amino]phenyl]methyl]pyridinium bromide 3-[[4-[Acetyl[[4-t-butyl-3-(tetradecyloxy)phenyl]methyl]amino]phenyl]methyl]-3,4-dimethyl-pyridinium bromide 3-[[4-[Acetyl[[4-methoxy-3-(tetradecyloxy)phenylmethyl]amino]phenyl]methyl]pyridinium bromide 3-[[4-[Acetyl[[4-methoxy-3-(tetradecyloxy)phenyl]methyl]amino]phenyl]methyl]-3,4-dimethyl-pyridinium bromide 3-[[3-[Acetyl[[4-(tetradecyloxy)phenyl]methyl]amino]phenyl]methyl]-3,4-dimethyl-pyridinium bromide 3-[[3-[Acetyl[[4-(hexadecyloxy)phenyl]methyl]amino]phenyl]methyl]pyridinium bromide 3-[[3-[Acetyl[[4-(dodecyloxy)phenyl]methyl]amino]phenyl]methyl]-3,4-dimethyl-pyridinium bromide 3-[[3-[Acetyl[[3-(tetradecyloxy)phenyl]methyl]amino]phenyl]methyl]pyridinium bromide 3-[[3-[Acetyl[[3-(tetradecyloxy)phenyl]methyl]amino]phenyl]methyl]-3,4-dimethyl-pyridinium bromide 3-[[3-[Acetyl[[3-(hexadecyloxy)phenyl]methyl]amino]phenyl]methyl]pyridinium bromide 3-[[3-[Acetyl[[3-(hexadecyloxy)phenyl]methyl]amino]phenyl]methyl]-3,4-dimethyl-pyridinium bromide 3-[[3-[Acetyl[[3-chloro-4-(tetradecyloxy)phenyl]methyl]amino]phenyl]methyl]pyridinium bromide 3-[[3-[Acetyl[[3-chloro-4-(tetradecyloxy)phenyl]methyl]amino]phenyl]methyl]-3,4-dimethyl-pyridinium bromide 3-[[3-[Acetyl[[3-chloro-4-(hexadecyloxy)phenyl]methyl]amino]phenyl]methyl]pyridinium bromide 3-[[3-[Acetyl[[3-chloro-4-(hexadecyloxy)phenyl]methyl]amino]phenyl]methyl]-3,4-dimethyl-pyridinium bromide 3-[[3-[Acetyl[[3-fluoro-4-(tetradecyloxy)phenyl]methyl]amino]phenyl]methyl]pyridinium bromide 3-[[3-[Acetyl[[3-fluoro-4-(tetradecyloxy)phenyl]methyl]amino]phenyl]methyl]-3,4-dimethyl-pyridinium bromide 3-[[3-[Acetyl[[3-t-butyl-4-(tetradecyloxy)phenyl]methyl]amino]phenyl]methyl]pyridinium bromide 3-[[3-[Acetyl[[3-t-butyl-4-(tetradecyloxy)phenyl]methyl]amino]phenyl]methyl]-3,4-dimethyl-pyridinium bromide 3-[[3-[Acetyl[[3-methoxy-4-(tetradecyloxy)phenyl]methyl]amino]phenyl]methyl]pyridinium bromide 3-[[3-[Acetyl[[3-methoxy-4-(tetradecyloxy)phenyl]methyl]amino]phenyl]methyl]-3,4-dimethyl-pyridinium bromide 3-[[3-[Acetyl[[4-chloro-3-(tetradecyloxy)phenyl]methyl]amino]phenyl]methyl]pyridinium bromide 3-[[3-[Acetyl[[4-chloro-3-(tetradecyloxy)phenyl]methyl]amino]phenyl]methyl]-3,4-dimethyl-pyridinium bromide 3-[[3-[Acetyl[[4-t-butyl-3-(tetradecyloxy)phenyl]methyl]amino]phenyl]methyl]pyridinium bromide 3-[[3-[Acetyl[[4-t-butyl-3-(tetradecyloxy)phenyl]methyl]amino]phenyl]methyl]-3,4-dimethyl-pyridinium bromide 3-[[3-[Acetyl[[4-methoxy-3-(tetradecyloxy)phenyl]methyl]amino]phenyl]methyl]pyridinium bromide 3-[[3-[Acetyl[[4-methoxy-3-(tetradecyloxy)phenyl]methyl]amino]phenyl]methyl]-3,4-dimethyl-pyridinium bromide 3-[[3-[[1-oxopropyl][[4-(tetradecyloxy)phenyl]methyl]amino]phenyl]methyl]pyridinium bromide 3-[[3-[[1-oxopropyl][[4-(tetradecyloxy)phenyl]methyl]amino]phenyl]methyl]-3,4-dimethyl-pyridinium bromide 3-[[3-[[1-oxopropyl][[3-(tetradecyloxy)phenyl]methyl]amino]phenyl]methyl]pyridinium bromide 3-[[3-[[1-oxopropyl][[3-(tetradecyloxy)phenyl]methyl]amino]phenyl]methyl]-3,4-dimethyl-pyridinium bromide 3-[[2-[Acetyl[[4-(tetradecyloxy)phenyl]methyl]amino]-Phenyl]methyl]-3,4-dimethyl-pyridinium bromide 3-[[2-[Acetyl[[3-(tetradecyloxy)Phenyl)methyl)amino]-Phenyl)methyl]-3,4-dimethyl-pyridinium bromide 3-[[2-[Acetyl[[3-chloro-4-(tetradecyloxy)Phenyl)methyl]amino]phenyl]methyl]-3,4-dimethyl-pyridinium bromide 3-[[2-[Acetyl[[3-fluoro-4-(tetradecyloxy)Phenyl)methyl]amino]Phenyl]methyl]-3,4-dimethyl-pyridinium bromide 3-[[2-[Acetyl[[3-methoxy-4-(tetradecyloxy)phenyl]methyl]amino]phenyl]methyl]-3,4-dimethyl-pyridinium bromide 3-[[2-[Acetyl[[4-chloro-3-(tetradecyloxy)Phenyl]methyl]amino]Phenyl]methyl]-3,4-dimethyl-pyridinium bromide 3-[[2-[Acetyl[[4-methoxy-3-(tetradecyloxy)phenyl]methyl]amino]phenyl]methyl]-3,4-dimethyl-pyridinium bromide 3-[[4-[Acetyl[[4-(tetradecyloxy)Phenyl]methyl]amino]Phenyl]methyl]imidaxo[1,5-a]Pyridinium bromide 3-[[4-[Acetyl[[4-(tetradecyloxy)phenyl]methyl]amino]Phenyl]methyl]-3,5-dimethyl-pyridinium bromide 3-[[4-[Acetyl[[4-(dodecyloxy)Phenyl]methyl]amino]phenyl]methyl]imidaxo[1,5-a]pyridinium bromide 3-[[4-[Acetyl[[4-(hexadecyloxy)phenyl]methyl]amino]Phenyl)methyl]-3,5-dimethyl-pyridinium bromide 3-[[4-[Acetyl[[3-(tetradecyloxy)phenyl]methyl]amino]phenyl]methyl]imidaxo[1,5-a]pyridinium bromide 3-[[4-[Acetyl[[3-(tetradecyloxy)phenyl]methyl]amino]phenyl]methyl]-3,5-dimethyl-pyridinium bromide 3-[[4-[Acetyl[[3-(dodecyloxy)phenyl]methyl]amino]phenyl]methyl]imidaxo[1,5-a]pyridinium bromide 3-[[4-[Acetyl[[3-(dodecyloxy)phenyl]methyl]amino]phenyl]methyl]-3,5-dimethyl-pyridinium bromide 3-[[4-[Acetyl[[3-chloro-4-(tetradecyloxy)phenyl]methyl]amino]phenyl]methyl]imidaxo[1,5-a]pyridinium bromide 3-[[4-[Acetyl[[3-chloro-4-(tetradecyloxy)phenyl]methyl]amino]phenyl]methyl]-3,5-dimethyl-pyridinium bromide 3-[[4-[Acetyl[[3-fluoro-4-(tetradecyloxy)phenyl]methyl]amino]phenyl]methyl]imidaxo[1,5-a]pyridinium bromide 3-[[4-[Acetyl[[3-fluoro-4-(tetradecyloxy)phenyl]methyl]amino]phenyl]methyl]-3,5-dimethyl-pyridinium bromide 3-[[4-[Acetyl[[3-t-butyl-4-(tetradecyloxy)phenyl]methyl]amino]phenyl]methyl]imidaxo[1,5-a]pyridinium bromide 3-[[4-[Acetyl[[3-t-butyl-4-(tetradecyloxy)phenyl]methyl]amino]phenyl]methyl]-3,5-dimethyl-pyridinium bromide 3-[[4-[Acetyl[[3-methoxy-4-(tetradecyloxy)phenyl]methyl]amino]phenyl]methyl]imidaxo[1,5-a]pyridinium bromide 3-[[4-[Acetyl[[3-methoxy-4-(tetradecyloxy)phenyl]methyl]amino]phenyl]methyl]-3,5-dimethyl-pyridinium bromide 3-[[4-[Acetyl[[4-chloro-3-(tetradecyloxy)phenyl]methyl]amino]phenyl]methyl]imidaxo[1,5-a]pyridinium bromide 3-[[4-[Acetyl[[4-chloro-3-(tetradecyloxy)phenyl]methyl]amino]phenyl]methyl]-3,5-dimethyl-pyridinium bromide 3-[[4-[Acetyl[[4-t-butyl-3-(tetradecyloxy)phenyl]methyl]amino]phenyl]methyl]imidaxo[1,5-a]pyridinium bromide 3-[[4-[Acetyl[[4-t-butyl-3-(tetradecyloxy)phenyl]methyl]amino]phenyl]methyl]-3,5-dimethyl-pyridinium bromide 3-[[4-[Acetyl[[4-methoxy-3-(tetradecyloxy)phenyl]methyl]amino]phenyl]methyl]imidaxo[1,5-a]pyridinium bromide 3-[[4-[Acetyl[[4-methoxy-3-(tetradecyloxy)phenyl]methyl]amino]phenyl]methyl]-3,5-dimethyl-pyridinium bromide 3-[[3-[Acetyl[[4-(tetradecyloxy)phenyl]methyl]amino]phenyl]methyl]-3,5-dimethyl-pyridinium bromide 3-[[3-[Acetyl[[4-(hexadecyloxy)phenyl]methyl]amino]phenyl]methyl]imidaxo[1,5-a]pyridinium bromide 3-[[3-[Acetyl[[4-(dodecyloxy)phenyl]methyl]amino]phenyl]methyl]-3,5-dimethyl-pyridinium bromide 3-[[3-[Acetyl[[3-(tetradecyloxy)phenyl]methyl]amino]phenyl]methyl]imidaxo[1,5-a]pyridinium bromide 3-[[3-[Acetyl[[3-(tetradecyloxy)phenyl]methyl]amino]phenyl]methyl]-3,5-dimethyl-pyridinium bromide 3-[[3-[Acetyl[[3-(hexadecyloxy)phenyl]methyl]amino]phenyl]methyl]imidaxo[1,5-a]pyridinium bromide 3-[[3-[Acetyl[[3-(hexadecyloxy)phenyl]methyl]amino]phenyl]methyl]-3,5-dimethyl-pyridinium bromide 3-[[3-[Acetyl[[3-chloro-4-(tetradecyloxy)phenyl]methyl]amino]phenyl]methyl]imidaxo[1,5-a]pyridinium bromide 3-[[3-[Acetyl[[3-chloro-4-(tetradecyloxy)phenyl]methyl]amino]phenyl]methyl]-3,5-dimethyl-pyridinium bromide 3-[[3-[Acetyl[[3-chloro-4-(hexadecyloxy)phenyl]methyl]amino]phenyl]methyl]imidaxo[1,5-a]pyridinium bromide 3-[[3-[Acetyl[[3-chloro-4-(hexadecyloxy)phenyl]methyl]amino]phenyl]methyl]-3,5-dimethyl-pyridinium bromide 3-[[3-[Acetyl[[3-fluoro-4-(tetradecyloxy)phenyl]methyl]amino]phenyl]methyl]imidaxo[1,5-a]pyridinium bromide 3-[[3-[Acetyl[[3-fluoro-4-(tetradecyloxy)Phenyl]methyl]amino]Phenyl]methyl]-3,5-dimethyl-pyridinium bromide 3-[[3-[Acetyl[[3-t-butyl-4-(tetradecyloxy)Phenyl]methyl]amino]Phenyl]methyl]imidaxo[1,5-a]pyridinium bromide 3-[[3-[Acetyl[[3-t-butyl-4-(tetradecyloxy)Phenyl)methyl]amino]Phenyl]methyl]-3,5-dimethyl-pyridinium bromide 3-[[3-[Acetyl[[3-methoxy-4-(tetradecyloxy)phenyl]methyl]amino]Phenyl]methyl]imidaxo[1,5-a]Pyridinium bromide 3-[[3-[Acetyl[[3-methoxy-4-(tetradecyloxy)phenyl]methyl]amino]phenyl]methyl]-3,5-dimethyl-pyridinium bromide 3-[[3-[Acetyl[[4-chloro-3-(tetradecyloxy)Phenyl]methyl]amino]phenyl]methyl]imidaxo[1,5-a]pyridinium bromide 3-[[3-[Acetyl[[4-chloro-3-(tetradecyloxy)phenyl]methyl]amino]phenyl]methyl]-3,5-dimethyl-pyridinium bromide 3-[[3-[Acetyl[[4-t-butyl-3-(tetradecyloxy)phenyl]methyl]amino]phenyl]methyl]imidaxo[1,5-a]pyridinium bromide 3-[[3-[Acetyl[[4-t-butyl-3-(tetradecyloxy)phenyl]methyl]amino]phenyl]methyl]-3,5-dimethyl-pyridinium bromide 3-[[3-[Acetyl[[4-methoxy-3-(tetradecyloxy)phenyl]methyl]amino]phenyl]methyl]imidaxo[1,5-a]pyridinium bromide 3-[[3-[Acetyl[[4-methoxy-3-(tetradecyloxy)phenyl]methyl]amino]phenyl]methyl]-3,5-dimethyl-pyridinium bromide 3-[[3-[[1-oxopropyl][[4-(tetradecyloxy)phenyl]methyl]amino]phenyl]methyl]imidaxo[1,5-a]pyridinium bromide 3-[[3-[[1-oxopropyl][[4-(tetradecyloxy)phenyl]methyl]amino]phenyl]methyl]-3,5-dimethyl-pyridinium bromide 3-[[3-[[1-oxopropyl][[3-(tetradecyloxy)phenyl]methyl]amino]phenyl]methyl]imidaxo[1,5-a]pyridinium bromide 3-[[3-[[1-oxopropyl][[3-(tetradecyloxy)phenyl]methyl-]amino]phenyl]methyl]-3,5-dimethyl-pyridinium bromide 3-[[2-[Acetyl[[4-(tetradecyloxy)phenyl]methyl]amino]-phenyl]methyl]-3,5-dimethyl-pyridinium bromide 3-[[2-[Acetyl[[3-(tetradecyloxy)phenyl]methyl]amino]-phenyl]methyl]-3,5-dimethyl-pyridinium bromide 3-[[2-[Acetyl[[3-chloro-4-(tetradecyloxy)phenyl]methyl]amino]phenyl]methyl]-3,5-dimethyl-pyridinium bromide 3-[[2-[Acetyl[[3-fluoro-4-(tetradecyloxy)Phenyl]methyl]amino]phenyl]methyl]-3,5-dimethyl-pyridinium bromide 3-[[2-[Acetyl[[3-methoxy-4-(tetradecyloxy)Phenyl]methyl]amino]Phenyl]methyl]-3,5-dimethyl-pyridinium bromide 3-[[2-[Acetyl[[4-chloro-3-(tetradecyloxy)Phenyl]methyl]amino]phenyl]methyl]-3,5-dimethyl-pyridinium bromide 3-[[2-[Acetyl[[4-methoxy-3-(tetradecyloxy)phenyl]methyl]amino]phenyl]methyl]-3,5-dimethyl-pyridinium bromide

We claim:

1. A compound of the formula:

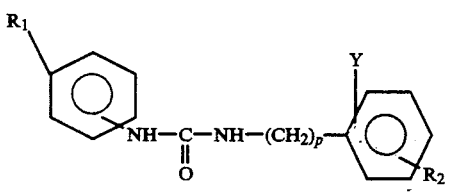

wherein
(A) p is the integer 0 or 1;
(B) $R_1$ represents one or more substituents of the aromatic ring which may be the same or different and is selected from the group consisting of:
(i) $C_1$-$C_{25}$ alkyl, $C_2$-$C_{25}$ alkenyl, $C_1$-$C_{25}$ alkoxy, $C_1$-$C_{25}$ thioalkyl, $C_2$-$C_{25}$ alkenyloxy, phenyl, phenoxy, substituted phenyl and substituted phenoxy wherein the substituents are selected from the group consisting of $C_1$-$C_{20}$ alkyl, $C_1$-$C_{20}$ alkoxy, halogen and trifluoromethyl;
(ii) hydrogen, halogen, trifluoromethyl, cyano and nitro;
(iii) —$CO_2R_4$, —$CONHR_3$, —CHO, $OCONHR_4$, and —$NHCOR_4$ wherein $R_3$ is selected from the group consisting of $C_1$-$C_4$ alkyl, $C_1$-$C_4$ alkoxy and $C_1$-$C_4$ alkylamino, and $R_4$ is selected from the group consisting of $C_1$-$C_{25}$ alkyl, $C_2$-$C_{25}$ alkenyl, phenyl and substituted phenyl wherein the substituents are selected from the group consisting of $C_1$-$C_{20}$ alkyl, $C_1$-$C_{20}$ alkoxy, halogen and trifluoromethyl;
C) the moiety $R_2$ represents one or more substituents of the aromatic ring which may be in any position and are selected from the group consisting of hydrogen, $C_1$-$C_5$ alkyl, $C_1$-$C_5$ alkoxy and halogen; and
(D) Y represents a moiety selected from those of the formulae:

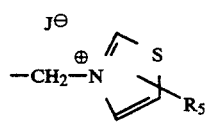

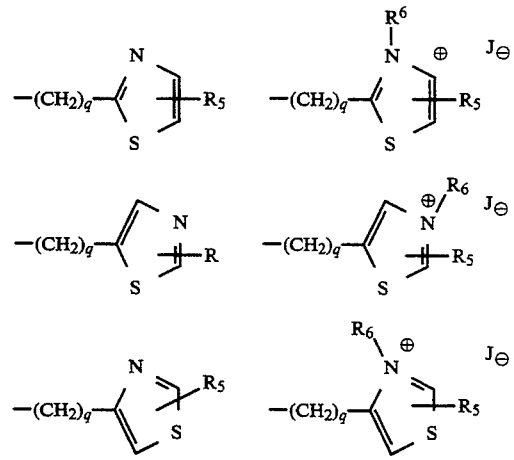

wherein the moiety $R_5$ is one or more substituents of the heterocyclic ring which may be the same or different and are selected from the group consisting of hydrogen, $C_1$-$C_6$ alkyl, $C_1$-$C_6$ acyl or $C_1$-$C_6$ alkoxy, $R_6$ is $C_1$-$C_4$ alkyl, q is 0 or 1, and $J^\ominus$ is a pharmacologically acceptable anion; and the pharmacologically acceptable salts thereof.

2. The compound according to claim 1, 5-methyl-3-[[3-[[[[4-(tetradecyloxy)phenyl]amino]carbonyl]amino]-phenyl]methyl]thiazolium bromide.

3. A pharmaceutical composition of matter in dosage unit form which comprises a compound of claim 1 in association with a pharmaceutically acceptable carrier.

4. A method for inhibiting the biological effects of Platelet Activating Factor in a mammal which comprises administering to the mammal a compound of claim 1 in an amount to inhibit Platelet Activating Factor effects.

5. A method of treating asthma in a mammal which comprises administering to the mammal an antiasthmatic amount of a compound of claim 1.

6. A method for treating anaphylactic and septic shock in a mammal which comprises administering to said mammal an effective amount of a compound of claim 1.

7. A method of treating psoriasis in a mammal which comprises administering to the mammal an effective amount of a compound of claim 1.

8. A method of treating bowel necrosis in a mammal which comprises administering to the mammal an effective amount of a compound of claim 1.

9. A method of treating adult respiratory distress syndrome in a mammal which comprises administering to the mammal an effective amount of a compound of claim 1.

10. A method of treating transplant rejection in a mammal which comprises administering to the mammal an effective amount of a compound of claim 1.

11. A method of treating thrombosis in a mammal which comprises administering to the mammal an effective amount of a compound of claim 1.

12. A method of treating stroke in a mammal which comprises administering to the mammal an effective amount of a compound of claim 1.

13. A method of treating cardiac anaphylaxis in a mammal which comprises administering to the mammal an effective amount of a compound of claim 1.

14. A method of treating cancer in a mammal which comprises administering to the mammal an effective amount of a compound of claim 1.

* * * * *